US012747243B2

(12) United States Patent
Schiltz et al.

(10) Patent No.: US 12,747,243 B2
(45) Date of Patent: Sep. 29, 2026

(54) SUBSTITUTED HETEROCYCLES FOR TREATING CANCER

(71) Applicant: Northwestern University, Evanston, IL (US)

(72) Inventors: Gary E. Schiltz, Evanston, IL (US); Karl A. Scheidt, Evanston, IL (US)

(73) Assignee: Northwestern University, Evanston, IL (US)

( * ) Notice: Subject to any disclaimer, the term of this patent is extended or adjusted under 35 U.S.C. 154(b) by 484 days.

(21) Appl. No.: 18/455,206

(22) Filed: Aug. 24, 2023

(65) Prior Publication Data

US 2024/0109903 A1 Apr. 4, 2024

Related U.S. Application Data

(60) Provisional application No. 63/400,520, filed on Aug. 24, 2022.

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
See application file for complete search history.

(56) References Cited

U.S. PATENT DOCUMENTS

| | | | |
|---|---|---|---|
| 4,229,453 | A | 10/1980 | Roth et al. |
| 5,254,687 | A | 10/1993 | Taylor et al. |
| 5,686,457 | A | 11/1997 | Traxler et al. |
| 5,869,485 | A | 2/1999 | Missbach |
| 6,051,577 | A | 4/2000 | Altmann |
| 6,066,732 | A | 5/2000 | Taylor et al. |
| 7,279,474 | B2 | 10/2007 | Capelli et al. |
| 7,358,250 | B2 | 4/2008 | Farthing et al. |
| 7,531,546 | B2 | 5/2009 | Irie et al. |
| 7,544,672 | B2 | 6/2009 | Kasibhatla et al. |
| 7,625,894 | B2 | 12/2009 | Caravatti et al. |
| 7,951,810 | B2 | 5/2011 | Critchley et al. |
| 7,951,812 | B2 | 5/2011 | Roberts et al. |
| 7,981,902 | B2 | 7/2011 | Gangjee |
| 8,093,229 | B2 | 1/2012 | Kasibhatla et al. |
| 8,183,248 | B2 | 5/2012 | Nagle et al. |
| 8,258,143 | B2 | 9/2012 | Gangjee et al. |
| 8,420,657 | B2 | 4/2013 | Gaul et al. |
| 8,501,752 | B2 | 8/2013 | Gangjee |

(Continued)

FOREIGN PATENT DOCUMENTS

| | | | |
|---|---|---|---|
| DE | 1916050 | A1 | 10/1969 |
| DE | 1916011 | A1 | 3/1970 |

(Continued)

OTHER PUBLICATIONS

Marquet et al. (Chimica Therapeutica (1971); 6 (6): 427-38). (Year: 1971).*

(Continued)

*Primary Examiner* — Brandon J Fetterolf
(74) *Attorney, Agent, or Firm* — Quarles & Brady LLP

(57) ABSTRACT

Disclosed are substituted pyrrolo[2,3-d]pyrimidine compounds. The disclosed compounds are shown to be useful in inhibiting the growth of cancer cell lines and treating cancer and cell proliferative disorders.

20 Claims, 16 Drawing Sheets

(56) References Cited

U.S. PATENT DOCUMENTS

| | | | |
|---|---|---|---|
| 8,507,672 | B2 | 8/2013 | Harrison et al. |
| 8,580,802 | B2 | 11/2013 | Salituro et al. |
| 8,633,205 | B2 | 1/2014 | Ledeboer et al. |
| 9,981,968 | B2 * | 5/2018 | Schiltz et al. |
| 2003/0018700 | A1 | 1/2003 | Giroti et al. |
| 2010/0144705 | A1 | 6/2010 | Miller |

FOREIGN PATENT DOCUMENTS

| | | | |
|---|---|---|---|
| DE | 2818676 | A1 | 11/1979 |
| HU | 9601559 | A2 | 2/1997 |
| JP | 2012116777 | A | 6/2012 |
| WO | 2005028434 | A2 | 3/2005 |
| WO | 2005105804 | A1 | 11/2005 |
| WO | 2007062399 | A2 | 5/2007 |
| WO | 2008006547 | A2 | 1/2008 |
| WO | 2010095663 | A1 | 8/2010 |
| WO | 2011145718 | A1 | 11/2011 |
| WO | 2012012712 | A2 | 1/2012 |

OTHER PUBLICATIONS

Gonda et al. Efficient Copper-Catalyzed Trifluoromethylation of Aromatic and Heteroaromatic lodides: The Beneficial Anchoring Effect of Borates Organic Letters (2014 ), 16(16), 4268-4271.

RN 1097301-32-0 of CAPLUS of STN, 1998.

Ji Y. et al., "Innate C—H trifluoromethylation of heterocycles," PNAS, 2011, 108; 14411-14415.

Gangjee et al., "Synthesis of 5,7-disubstituted-4-methyl-7H-pyrrolo[2,3-d]pyrimidin-2-amines as microtubule inhibitors", Bioorganic & Medicinal Chemistry, Mar. 1, 2013, 21 (5):1180-1189.

Gangjee et al., "Design, synthesis, and x-ray crystal structure of a potent dual inhibitor of thymidylate synthase and dihydrofolate reductase as an antitumor agent", Journal of Medicinal Chemistry, 2000, 43(21 ):3837-3851.

International Preliminary Report on Patentability for PCT/US2014/030368 dated Sep. 15, 2015.

International Search Report and Written Opinion, corresponding to PCT/US2014/030368 dated Oct. 9, 2014.

* cited by examiner

NUCC-0226674

NUCC-0226683

NUCC-0226683

NUCC-0226694

NUCC-0226694

NUCC-0226695

SUBSTITUTED HETEROCYCLES FOR TREATING CANCER

CROSS-REFERENCE TO RELATED APPLICATIONS

This application claims benefit of priority to U.S. Application Ser. No. 63/400,520, filed Aug. 24, 2022, the contents of which are incorporated by reference in its entirety.

BACKGROUND OF THE INVENTION

The field of the invention relates to substituted pyrrolo [2,3-d]pyrimidines. In particular, the field of the invention relates to substituted pyrrolo[2,3-d]pyrimidines for the treatment of cell proliferation diseases and disorders such as cancer.

While treatment options have improved in recent years, cancer remains the second leading cause of death in the United States. Many cancers lack effective treatments and have poor long-term prognoses. Additional treatment options are necessary for patients who fail to respond to current therapies and for those who develop resistance to current therapies Here, as part of an effort to discover and evaluate new small molecules that have the potential for treating human cancer, in particular hematological malignancies, we have identified a series of novel substituted pyrrolo[2,3-d]pyrimidine compounds that display potent in vitro cytotoxicity against cancer cells. These compounds present unique substitution patterns that impart on them activity against human cancer cell lines. Compound analogs have been synthesized and tested to generate robust structure-activity relationships based on multiple sites of diversification. Lead compounds possess excellent profiles as potential therapeutics based on a variety of physiochemical properties. These new compounds therefore hold promise as new potential treatments for cancer and other proliferative diseases.

BRIEF SUMMARY OF THE INVENTION

Disclosed are substituted pyrrolo[2,3-d]pyrimidines. The disclosed compounds may be used in pharmaceutical compositions and methods for treating cell proliferative disorders such as cancer.

The disclosed substituted heterocycles may include substituted 7H-pyrrolo[2,3-d]pyrimidines having a formula:

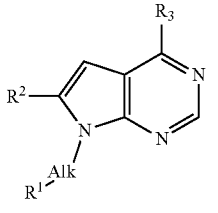

wherein

Alk is $(-CH_2-)_n$, wherein n is 1-6;

$R^1$ is selected from hydrogen, hydroxyl, hydroxyalkyl (e.g., $-C(OH)(CH_3)CH_3$ or $-CH_2-C(OH)(CH_3)CH_3$), amino, alkylamino, dialkylamino (e.g., $-N(CH_3)_2$), alkoxy, hydroxyalkoxy (e.g., $-O-CH_2-CH_2-OH$), or $R^1$ is a 3-, 4-, 5-, or 6-membered ring comprising carbon atoms and optionally comprising one or more heteroatoms selected from N, O, and S, wherein the ring is unsaturated or saturated at one or more positions and the ring optionally is substituted at one or more positions with a substituent selected from oxo, dioxo, alkoxycarbonyl (e.g., $-C(O)-O-C(CH_3)_3$), amidinyl (e.g., $-C(=NH)(NH_2)$), alkyl, alkoxy, haloalkyl, alkylcarbonyl (e.g., $-C(O)-CH_3$), aminocarbonyl (e.g., $-C(O)-NH_2$), halogen, hydroxyl, hydroxyalkyl, and aryl optionally substituted with halo;

$R^2$ is selected from hydrogen and methyl optionally substituted with halo (e.g., trifluoromethyl) and hydrogen;

$R^3$ is selected from halo (e.g., chloro), hydrogen, methyl, and hydroxyl; and with the proviso that if $R^2$ is trifluoromethyl, $R^3$ is chloro, and n is 1, then $R^1$ is not piperdin-4-yl or tert-butyl piperidine-1-carboxylate.

In the disclosed formula, $R^1$ may be selected from optionally substituted pyrrolidine (e.g., 2-pyrrolidinone), optionally substituted thiane (e.g., pentamethylene sulfone), optionally substituted azetidine (e.g., tert-butyl azetidine-1-carboxylate or azetidine-carboximidamide or 1-(2,2,2-trifluoroethyl)azetidine), optionally substituted oxane, optionally substituted piperidine (e.g., piperidine-1-carboxamide, tert-butyl piperidine-1-carboxylate, or 1-(2,2,2-trifluoroethyl)piperidine), optionally substituted morpholino, optionally substituted piperazine (e.g., tert-butyl piperazine-1-carboxylate or 1-(2,2,2-trifluoroethyl)piperazine), optionally substituted pyrazole (e.g., pyrazol-1-yl or 3,5-dimethyl-1H-pyrazol-4-yl), optionally substituted phenyl (e.g., 4-fluorophenyl or 2,4-difluorophenyl), optionally substituted cyclohexane (e.g., 4-cyclohexanol), optionally substituted pyridinyl (e.g., pyridin-3-yl, pyridin-4-yl, 3-methoxy-pyridin-4-yl, 1H-pyridin-2-one-4-yl, 4-methoxy-pyridin-3-yl).

In the disclosed formula, $R^3$ may be trifluoromethyl.

In the disclosed formula, $R^2$ may be chloro.

In the disclosed formula, n may be 1 or 2.

In some embodiments, $R^3$ is trifluoromethyl, $R^2$ is chloro, and n is 1 or 2.

Also disclosed are pharmaceutical compositions that comprise the disclosed compounds together with a carrier, diluent, or excipient. The pharmaceutical compositions may comprise an effective amount of the compounds (or salts, esters, amides, or solvates thereof) for treating and/or preventing a disease, disorder, or condition which may include cell proliferation diseases, disorders, or conditions, such as cancer.

Also disclosed are methods of treating cancer that include administering the disclosed compounds, for example, where the compounds are formulated as a pharmaceutical composition and administered to a patient having cancer or suspected of having cancer. Cancers treated by the disclosed methods may include, but are not limited to leukemia (e.g. acute myeloid leukemia, acute lymphoblastic leukemia, acute promyelocytic leukemia, and chronic myelogenous leukemia), non-small cell lung cancer, colon cancer, cancer of the central nervous system, melanoma, ovarian cancer, renal cancer, prostate cancer, and breast cancer.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
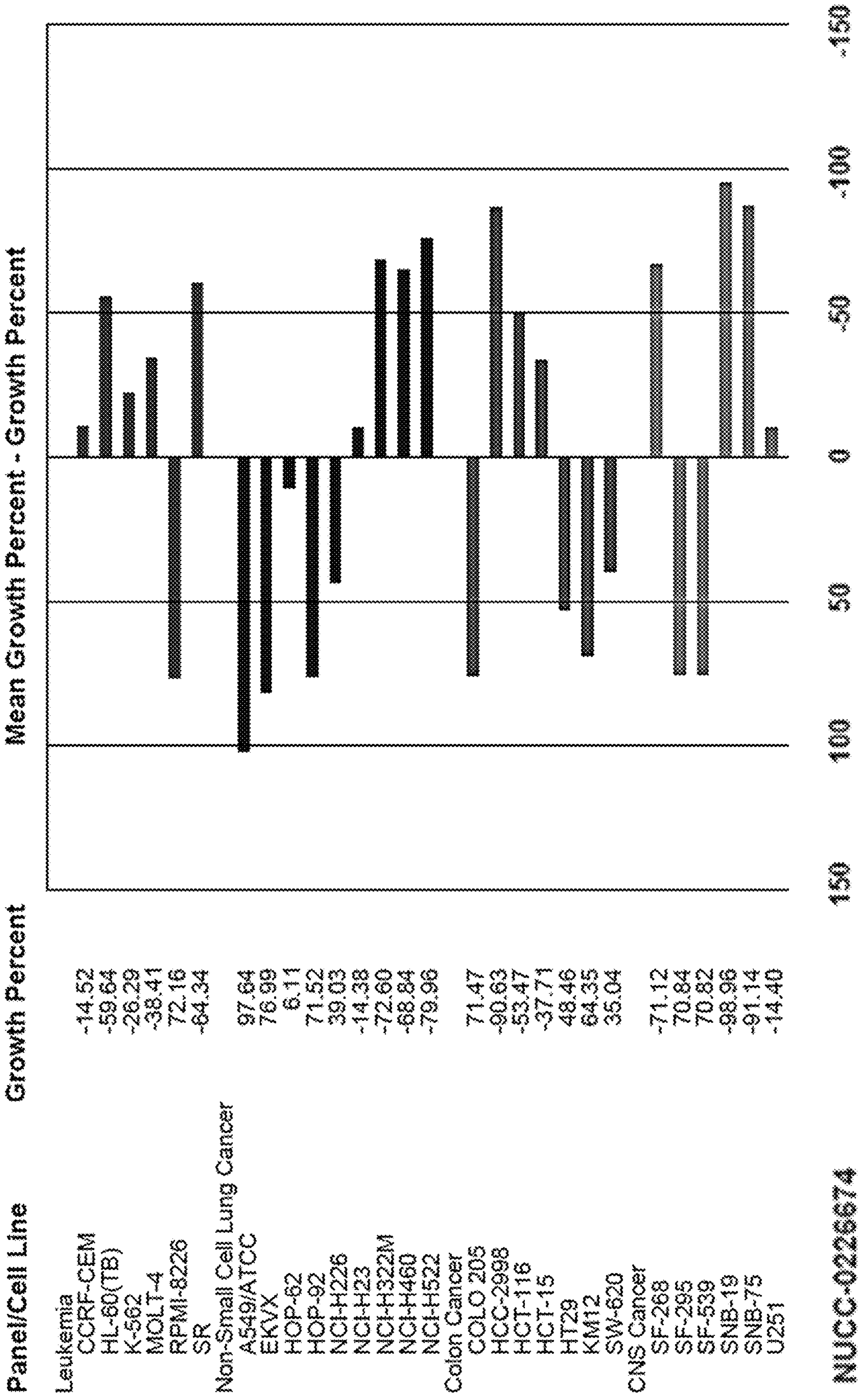
FIG. 1 shows single dose data demonstrating the effect of the compound NUCC-0226674 on various cancer cell lines. Negative growth percent indicates the amount of cancer cells in a specific cancer cell line being killed by the compound NUCC-0226674, compared to the amount of cancer cells present at the start of the treatment.
Figure 1:
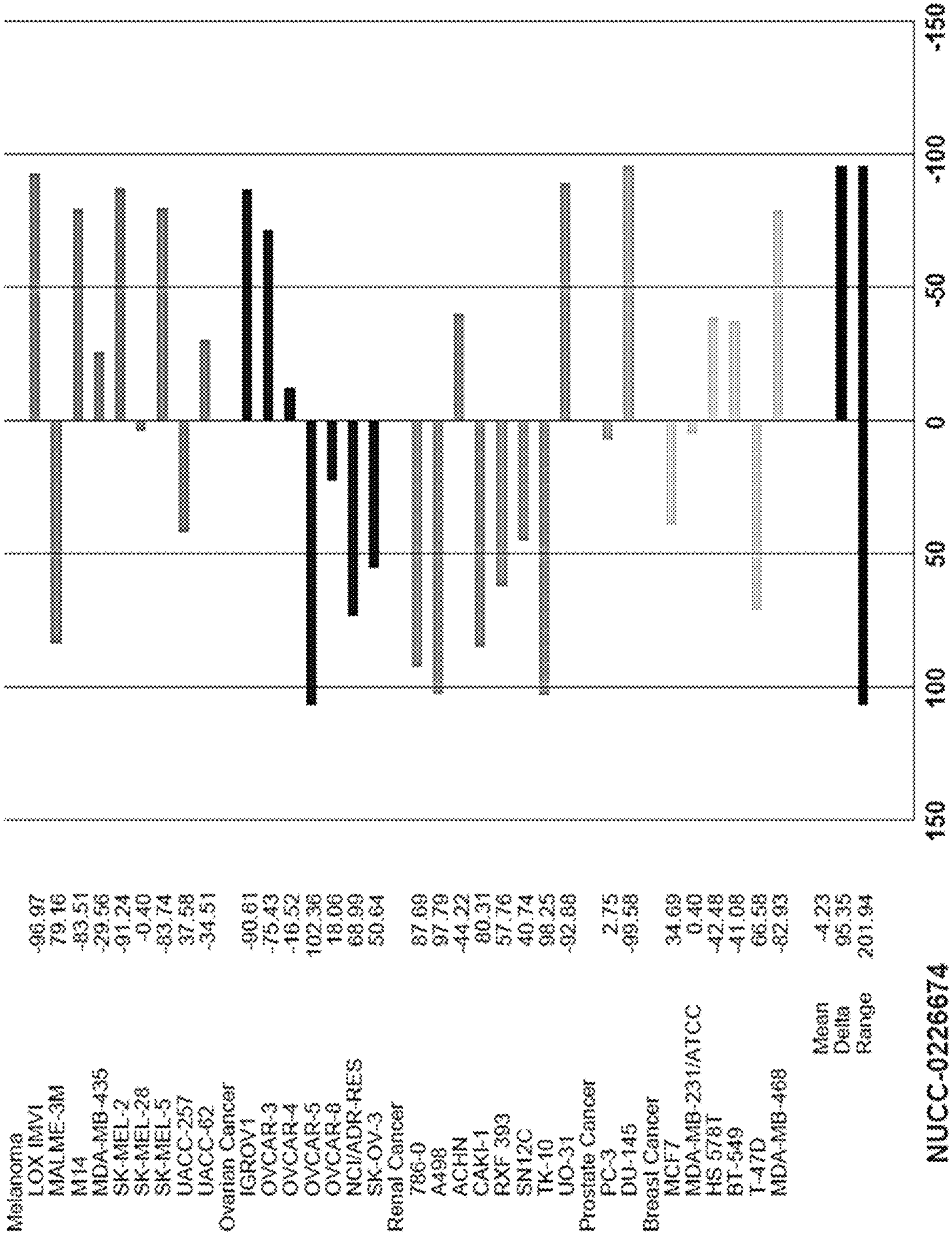

Disclosed herein are substituted pyrrolo-pyrimidine compounds that may be used for treatment of cancer and other proliferative disorders.

The present invention is described herein using several definitions, as set forth below and throughout the application.

As used in this specification and the claims, the singular forms "a," "an," and "the" include plural forms unless the context clearly dictates otherwise. For example, the term "a compound" should be interpreted to mean "one or more compounds" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a substituted heterocycle such as the presently disclosed substituted pyrrolo[2,3-d]pyrimidines. For example, a "subject in need of treatment" may include a subject having a cell proliferative disease, disorder, or condition such as cancer (e.g., cancers such as leukemia, non-small cell lung cancer, colon cancer, cancer of the central nervous system, melanoma, ovarian cancer, renal cancer, prostate cancer, and breast cancer). In some embodiments, the cancer is a leukemia such as acute myeloid leukemia (AML), acute lymphoblastic leukemia, acute promyelocytic leukemia, and chronic myelogenous leukemia. In some embodiments, the cancer is non-small cell lung cancer. In some embodiments, the cancer is colon cancer. In some embodiments, the cancer is central nervous system cancer. In some embodiments, the cancer is melanoma. In some embodiments, the cancer is ovarian cancer. In some embodiments, the cancer is renal cancer. In some embodiments, the cancer is prostate cancer. In some embodiments, the cancer is breast cancer.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

The disclosed compounds may be effective in inhibiting cell proliferation of cancer cells. For example, the disclosed compound may be effective in inhibiting cell proliferation of one or more types of cancer cells including: leukemia cells, such as MV-4-11, CCRF-CEM, HL-60(TB), K-562, MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS cancer cells: SF-268, SF-295, SF-539, SNB-19, SNB-75 and U251; melanoma cancer cells, such as LOX IMV1, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D). In some embodiments, the cells are acute myeloid leukemia cells such as MV-4-11 cells. In some embodiments, the cells are acute lymphoblastic leukemia cells such as CCRF-CEM cells and MOLT-4 cells. In some embodiments, the cells are acute promyelocytic leukemia cells such as HL-60(TB). In some embodiments, the cells are chronic myelogenous leukemia patient cells such as K-562. In some embodiments, the cells are other leukemia cells such as RPMI-8226 cells and SR cells. In some embodiments, the cells are non-small lung cancer cells, such as A549/ATCC, EKVX, HOP-62, HOP-92, NCI-H226, NCI-H23, NCI-H322M, NCI-H460 and NCI-H522 cells. In some embodiments, the cells are colon cancer cells, such as COLO 205, HCC-2998, HCT-116, HCT-15, HT29, KM12 and SW-620 cells. In some embodiments, the cells are CNS cancer cells such as SF-268, SF-295, SF-539, SNB-19, SNB-75 and U251 cells. In some embodiments, the cells are melanoma cancer cells, such as LOX IMV1, MALME-3M, M14, MDA-MB-435, SK-MEL-2, SK-MEL-28, SK-MEL-5, UACC-257 and UACC-62 cells. In some embodiments, the cells are ovarian cancer cells, such as IGR-OV1, OVCAR-3, OVCAR-4, OVCAR-5, OVCAR-8, NCI/ADR-RES and SK-OV-3 cells. In some embodiments, the cells are renal cancer cells, such as 786-0, A498, ACHN, CAKI-1, RXF 393, SN12C, TK-10 and UO-31 cells. In some embodiments, the cells are prostate cancer cells, such as DU-145 and PC-3 cells. In some embodiments, the cells are breast cancer cells, such as MCF7, MDA-MB-231/ATCC, MDA-MB-468, HS 578T, BT-549 and T-47D cells.

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an IC50 of less than about 10 μM, 5 μM, 1 μM, or 0.5 μM in the selected assay.

Compounds

Disclosed herein are substituted heterocycles. The substituted heterocycles include substituted 7H-pyrrolo[2,3-d]pyrimidines and demonstrate the ability to inhibit cell proliferation of cancer cells.

The disclosed substituted heterocycles may include substituted 7H-pyrrolo[2,3-d]pyrimidines having a formula:

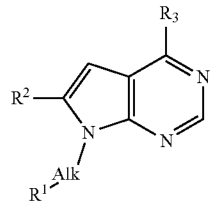

wherein

Alk is $(-CH_2-)_n$, wherein n is 1-6;

$R^1$ is selected from hydrogen, hydroxyl, hydroxyalkyl (e.g., $-C(OH)(CH_3)CH_3$ or $-CH_2-C(OH)(CH_3)CH_3$), amino, alkylamino, dialkylamino (e.g., $-N(CH_3)_2$), alkoxy, hydroxyalkoxy (e.g., $-O-CH_2-CH_2-OH$), or $R^1$ is a 3-, 4-, 5-, or 6-membered ring comprising carbon atoms and optionally comprising one or more heteroatoms selected from N, O, and S, wherein the ring is unsaturated or saturated at one or more positions and the ring optionally is substituted at one or more positions with a substituent selected from oxo, dioxo, alkoxycarbonyl (e.g., $-C(O)-O-C(CH_3)_3$), amidinyl (e.g., $-C(=NH)(NH_2)$), alkyl, alkoxy, haloalkyl, alkylcarbonyl (e.g., $-C(O)-CH_3$), aminocarbonyl (e.g., $-C(O)-NH_2$), halogen, hydroxyl, hydroxyalkyl, and aryl optionally substituted with halo;

$R^2$ is selected from hydrogen and methyl optionally substituted with halo (e.g., trifluoromethyl); and $R^3$ is selected from halo (e.g., chloro), hydrogen, methyl, and hydroxyl; with the proviso that if $R^2$ is trifluoromethyl, $R^3$ is chloro, and n is 1, then $R^1$ is not piperdin-4-yl or tert-butyl piperidine-1-carboxylate.

In some embodiments of these disclosed substituted 7H-pyrrolo[2,3-d]pyrimidines, $R^1$ is selected from optionally substituted pyrrolidine (e.g., 2-pyrrolidinone), optionally substituted thiane (e.g., pentamethylene sulfone), optionally substituted azetidine (e.g., tert-butyl azetidine-1-carboxylate or azetidine-carboximidamide or 1-(2,2,2-trifluoroethyl)azetidine), optionally substituted oxane, optionally substituted piperidine (e.g., piperidine-1-carboxamide, tert-butyl piperidine-1-carboxylate, or 1-(2,2,2-trifluoroethyl)piperidine), optionally substituted morpholino, optionally substituted piperazine (e.g., tert-butyl piperazine-1-carboxylate or 1-(2,2,2-trifluoroethyl)piperazine, optionally substituted pyrazole (e.g., pyrazol-1-yl or 3,5-dimethyl-1H-pyrazol-4-yl), optionally substituted phenyl (e.g., 4-fluorophenyl or 2,4-difluorophenyl), optionally substituted cyclohexane (e.g., 4-cyclohexanol), and optionally substituted pyridinyl (e.g., pyridin-3-yl, pyridin-4-yl, 3-methoxy-pyridin-4-yl, 1H-pyridin-2-one-4-yl, 4-methoxy-pyridin-3-yl).

In some embodiments of the disclosed compounds, $R^2$ is trifluoromethyl.

In some embodiments of the disclosed compounds, $R^3$ is chloro.

In some embodiments of the disclosed compounds, n is 1 or 2.

In some embodiments, $R^2$ is trifluoromethyl, $R^3$ is chloro, and n is 1. In other embodiments, $R^2$ is trifluoromethyl, $R^3$ is chloro, and n is 2.

In some embodiments, $R^1$ is not an optionally substituted piperidine. In some embodiments, $R^2$ is trifluoromethyl, $R^3$ is chloro, n is 1, and $R^1$ is not an optionally substituted piperidine.

In some embodiments, $R^1$ is not piperdin-4-yl. In some embodiments, $R^2$ is trifluoromethyl, $R^3$ is chloro, n is 1, and $R^1$ is not piperdin-4-yl. In some embodiments, the compound is not

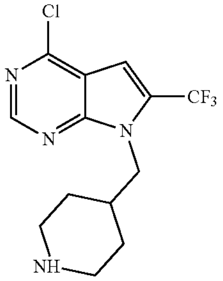 [SMILES: FC(F)(F)c1cc2c(Cl)ncnc2n1CC1CCNCC1]

(i.e., 4-chloro-7-(piperidin-4-ylmethyl)-6-(trifluoromethyl)-7H-pyrrolo[2,3-d]pyrimidine).

In some embodiments, $R^1$ is not tert-butyl piperidine-1-carboxylate. In some embodiments, $R^2$ is trifluoromethyl, $R^3$ is chloro, n is 1, and $R^1$ is not tert-butyl piperidine-1-carboxylate. In some embodiments, the compound is not

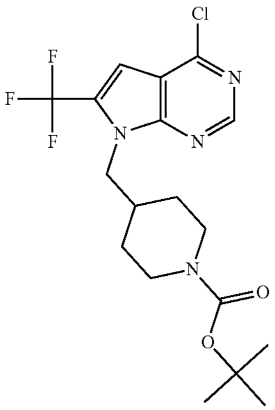 [SMILES: CC(C)(C)OC(=O)N1CCC(Cn2c(C(F)(F)F)cc3c(Cl)ncnc32)CC1]

(i.e., tert-butyl 4-((4-chloro-6-(trifluoromethyl)-7H-pyrrolo[2,3-d]pyrimidin-7-yl)methyl)piperidine-1-carboxylate).

In some embodiments of these disclosed substituted 7H-pyrrolo[2,3-d]pyrimidines, the compound is one or more of the compounds shown in Table 1.

In some embodiments, the disclosed compound has a IC50 against MV-4-11 acute myeloid leukemia cells of less than 2.0 μM (e.g., NUCC-0226439, NUCC-0226440, NUCC-0226665, NUCC-0226667, NUCC-0226669, NUCC-0226670, NUCC-0226672, NUCC-0226674, NUCC-0226677, NUCC-0226678, NUCC-0226679, NUCC-0226680, NUCC-0226681, NUCC-0226683, NUCC-0226684, NUCC-0226686, NUCC-0226689, NUCC-0226690, NUCC-0226691, NUCC-0226692, NUCC-0226694, NUCC-0226695, NUCC-0226697, NUCC-0226698, or NUCC-0226701 of Table 1).

In some embodiments, the disclosed compound has a IC50 against MV-4-11 acute myeloid leukemia cells of less than 1.0 μM (e.g., NUCC-0226439, NUCC-0226440, NUCC-0226672, NUCC-0226679, NUCC-0226680, NUCC-0226681, NUCC-0226684, NUCC-0226689, NUCC-0226690, NUCC-0226692, NUCC-0226694, NUCC-0226695, or NUCC-0226701 of Table 1).

As used herein, a wavy line "〰" may be used to designate the point of attachment for any radical group or substituent group.

As used herein, the term "alkyl" refers to a straight-chain or branched alkyl radical in all of its isomeric forms, such as a straight or branched group of 1-12, 1-10, or 1-6 carbon atoms, referred to herein as $C_1$-$C_{12}$-alkyl, $C_1$-$C_{10}$-alkyl, and $C_1$-$C_6$-alkyl, respectively.

The term "alkylene" refers to a diradical of straight-chain or branched alkyl group (e.g., a diradical of straight-chain or branched $C_1$-$C_{12}$ alkyl group). Exemplary alkylene groups include, but are not limited to $-CH_2-$, $-CH_2CH_2-$, $-CH_2CH_2CH_2-$, $-CH(CH_3)CH_2-$, $-CH_2CH(CH_3)CH_2-$, $-CH(CH_2CH_3)CH_2-$, and the like.

The terms "alkoxy" or "alkoxyl" refers to an alkyl group, as defined above, having an oxygen radical attached thereto. Representative alkoxy groups include methoxy, ethoxy, tert-butoxy and the like.

The term "halo" or "halogen" refers to a halogen atom or halogen radical (e.g., —F, —Cl, —Br, or —I).

The term "haloalkyl" refers to an alkyl group that is substituted with at least one halogen. For example, $-CH_2F$, $-CHF_2$, $-CF_3$, $-CH_2CF_3$, $-CF_2CF_3$, and the like.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. The number of carbon atoms in the cycloalkyl group can be specified using the Cx-Cy nomenclature where x and y are integers specifying the number of carbon atoms. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using "x-membered to y-membered" nomenclature where x and y are integers specifying the number of ring atoms. For example, a 3-membered to 7-membered heterocyclyl group refers to a saturated or partially unsaturated 3- to 7-membered ring structure containing one to four heteroatoms, such as nitrogen, oxygen, and sulfur. The designation indicates that the heterocyclic ring contains a total of from 3 to 7 ring atoms, inclusive of any heteroatoms that occupy a ring atom position.

The term "aryl" refers to a carbocyclic aromatic group. The term "aryl" includes monocyclic ring systems, and polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aryl ring is unsubstituted. In certain embodiments, the aryl group is a 6-10 membered ring structure. Representative aryl groups include phenyl, naphthyl, anthracenyl, 1,3-benzodioxolyl and the like.

The substituents on the aryl (e.g., phenyl) rings in the compounds of the disclosure may be at ortho-, meta-, or para-positions.

The terms "amine" and "amino" are art-recognized and refer to unsubstituted amines.

The terms "alkylamine" and "alkylamino" are art-recognized and refer to mono-substituted amines, wherein substituent may include, for example, alkyl, cycloalkyl, heterocyclyl, alkenyl, and aryl.

The terms "dialkylamine" and "dialkylamino" are art-recognized and refer to di-substituted amines, wherein substituent may include, for example, alkyl, cycloalkyl, heterocyclyl, alkenyl, and aryl.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively.

The term "carbonyl" as used herein refers to the radical —C(O)—.

The term "hydroxyl" refers to the substituent of "—OH".

The term "oxo" refers to a divalent oxygen atom

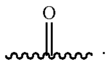

The term "dioxo" refers to two divalent oxygen atoms attached to the same atom

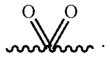

The term "hydroxyalkyl" refers to an alkyl group, as defined herein, that is substituted with one or more hydroxyl groups.

The term "hydroxyalkoxy" refers to an alkoxy group, as defined herein, that is substituted with one or more hydroxyl groups.

The term "alkoxycarbonyl" refers to a carbonyl group that is attached to an alkoxy group as defined herein.

The term "amidinyl" refers to a radical that has a structure of —C(=NH)$NH_2$.

The term "alkylcarbonyl" refers to a carbonyl group that is attached to an alkyl group as defined herein.

The term "aminocarbonyl" refers to a carbonyl group that is attached to an amino, alkylamino, or dialkylamino group, as defined herein.

The formulae of the compounds disclosed herein should be interpreted as encompassing all possible stereoisomers, enantiomers, or epimers of the compounds unless the formulae indicate a specific stereoisomer, enantiomer, or epimer. The formulae of the compounds disclosed herein should be interpreted as encompassing salts, esters, amides, or solvates thereof of the compounds.

The disclosed compounds may be formulated as anti-cancer therapeutics, including hematologic malignancies (e.g., leukemia, acute myeloid leukemia, acute lymphoblastic leukemia, acute promyelocytic leukemia, or chronic myelogenous leukemia), breast, lung, colon, central nervous system, skin, ovary, kidney, and prostate malignancies.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 μM, 0.005 μM, 0.01 μM, 0.5 μM, 0.1 μM, 1.0 μM, 10 μM, and 100 μM (e.g., 0.1 μM–1.0 μM).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer (e.g., cancers such as leukemia, non-small cell lung cancer, colon cancer, cancer of the central nervous system, melanoma, ovarian cancer, renal cancer, prostate cancer, and breast cancer). In some embodiments, the cancer is acute myeloid leukemia. In some embodiments, the cancer is a leukemia such as acute lymphoblastic leukemia, acute promyelocytic leukemia, or chronic myelogenous leukemia. In some embodiments, the cancer is non-small cell lung cancer. In some embodiments, the cancer is colon cancer. In some embodiments, the cancer is central nervous system cancer. In some embodiments, the cancer is melanoma. In some embodiments, the cancer is ovarian cancer. In some embodiments, the cancer is renal cancer. In some embodiments, the cancer is prostate cancer. In some embodiments, the cancer is breast cancer.

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Optionally, the disclosed compounds or pharmaceutical compositions comprising the disclosed compounds may be administered with additional therapeutic agents, optionally in combination, in order to treat cell proliferative diseases and disorders. In some embodiments of the disclosed methods, one or more additional therapeutic agents are administered with the disclosed compounds or with pharmaceutical compositions comprising the disclosed compounds, where the additional therapeutic agent is administered prior to, concurrently with, or after administering the disclosed compounds or the pharmaceutical compositions comprising the disclosed compounds. In some embodiments, the disclosed pharmaceutical composition are formulated to comprise the disclosed compounds and further to comprise one or more additional therapeutic agents, for example, one or more additional therapeutic agents for treating cell proliferative diseases and disorders.

ILLUSTRATIVE EMBODIMENTS

Embodiment 1. A compound, or a pharmaceutically salt thereof, the compound having a formula of

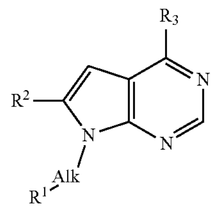

wherein:

Alk is ($-CH_2-)_n$, wherein n is 1-6 (e.g., 1, 2, 3, 4, 5, or 6);

$R^1$ is selected from hydrogen, hydroxy, hydroxyalkyl (e.g., $-C(OH)(CH_3)CH_3$ or $-CH_2-C(OH)(CH_3)CH_3$), amino, alkylamino, dialkylamino (e.g., $-N(CH_3)_2$), alkoxy, and hydroxyalkoxy (e.g., $-O-CH_2-CH_2-OH$), or $R^1$ is a 3-, 4-, 5-, or 6-membered ring comprising carbon atoms and optionally comprising one or more heteroatoms selected from N, O, and S, wherein the ring is unsaturated or saturated at one or more positions and the ring optionally is substituted at one or more positions with a substituent selected from oxo, dioxo, alkoxycarbonyl (e.g., $-C(O)-O-C(CH_3)_3$), amidinyl (e.g., $-C(=NH)(NH_2)$), alkyl, alkoxy, haloalkyl, alkylcarbonyl (e.g., $-C(O)-CH_3$), aminocarbonyl (e.g., $-C(O)-NH_2$), halogen, hydroxyl, hydroxyalkyl, and aryl optionally substituted with halo;

$R^2$ is selected from hydrogen and methyl optionally substituted with halo (e.g., trifluoromethyl);

$R^3$ is selected from halo (e.g., chloro), hydrogen, methyl, and hydroxyl; and with the proviso that if $R^2$ is trifluoromethyl, $R^3$ is chloro, and n is 1, then $R^1$ is not piperdin-4-yl or tert-butyl piperidine-1-carboxylate.

Embodiment 2. The compound of embodiment 1, wherein $R^1$ is selected from optionally substituted pyrrolidine (e.g., 2-pyrrolidinone), optionally substituted thiane (e.g., pentamethylene sulfone), optionally substituted azetidine (e.g., tert-butyl azetidine-1-carboxylate or azetidine-carboximidamide or 1-(2,2,2-trifluoroethyl) azetidine), optionally substituted oxane, optionally substituted piperidine (e.g., piperidine-1-carboxamide, tert-butyl piperidine-1-carboxylate, or 1-(2,2,2-trifluoroethyl)piperidine), optionally substituted morpholino, optionally substituted piperazine (e.g., tert-butyl piperazine-1-carboxylate or 1-(2,2,2-trifluoroethyl)piperazine, optionally substituted pyrazole (e.g., pyrazol-1-yl or 3,5-dimethyl-1H-pyrazol-4-yl), optionally substituted phenyl (e.g., 4-fluorophenyl or 2,4-difluorophenyl), optionally substituted cyclohexane (e.g., 4-cyclohexanol), and optionally substituted pyridinyl (e.g., pyridin-3-yl, pyridin-4-yl, 3-methoxy-pyridin-4-yl, 1H-pyridin-2-one-4-yl, 4-methoxy-pyridin-3-yl).

Embodiment 3. The compound of any one of embodiments 1-2, wherein $R^2$ is trifluoromethyl.

Embodiment 4. The compound of any one of embodiments 1-3, wherein $R^3$ is chloro.

Embodiment 5. The compound of any one of embodiments 1-4, wherein n is 1 or 2.

Embodiment 6. The compound of any one of embodiments 1-5, wherein $R^2$ is trifluoromethyl, $R^3$ is chloro, and n is 1.

Embodiment 7. The compound of any one of embodiments 1-5, wherein $R^2$ is trifluoromethyl, $R^3$ is chloro, and n is 2.

Embodiment 8. The compound of any one of embodiments 1-7, wherein if $R^2$ is trifluoromethyl, $R^3$ is chloro, and n is any one of 2-6 (e.g., 2, 3, 4, 5, or 6), then $R^1$ is not an optionally substituted piperidine.

Embodiment 9. The compound of any one of embodiments 1-7, wherein if $R^2$ is trifluoromethyl, $R^3$ is chloro, and n is any one of 2-6 (e.g., 2, 3, 4, 5, or 6), then $R^1$ is not piperdin-4-yl.

Embodiment 10. The compound of any one of embodiments 1-7, wherein if $R^2$ is trifluoromethyl, $R^3$ is chloro, and n is any one of 2-6 (e.g., 2, 3, 4, 5, or 6), then $R^1$ is not tert-butyl piperidine-1-carboxylate.

Embodiment 11. The compound of embodiment 1, wherein the compound is selected from

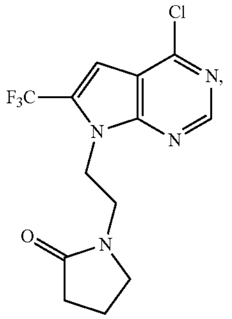
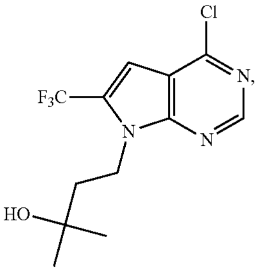
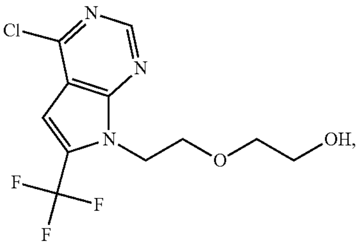
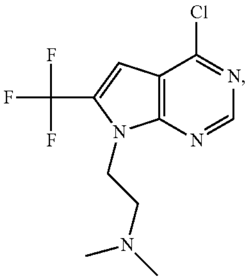
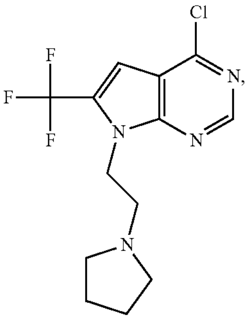

-continued

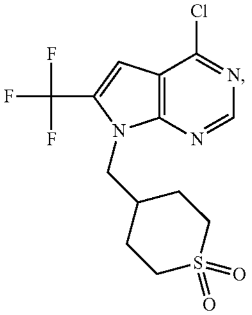
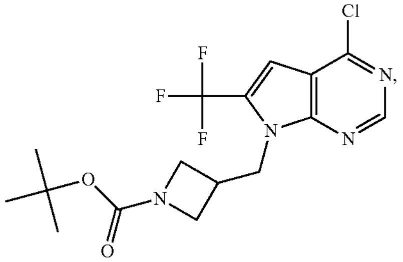
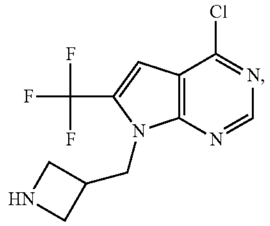
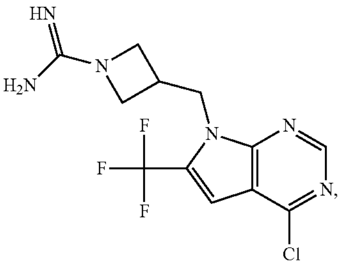
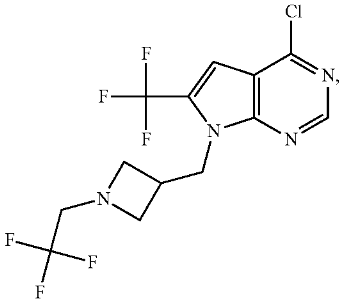
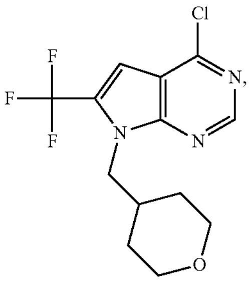
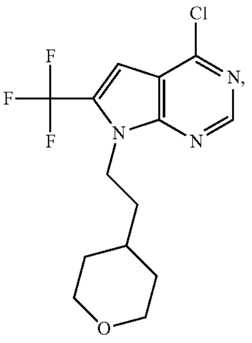

-continued
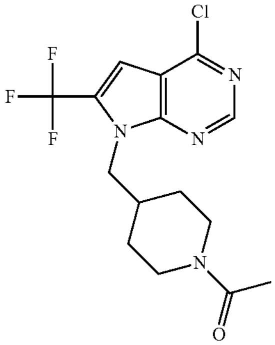
,
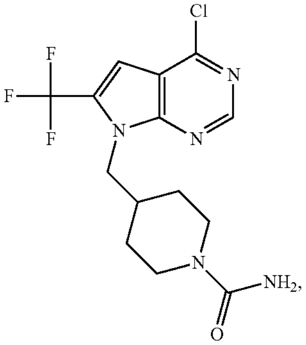
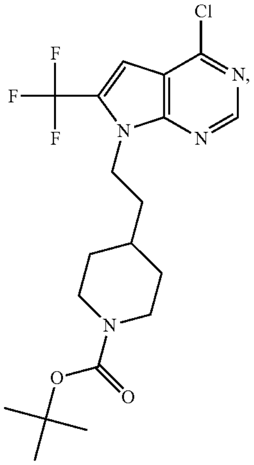
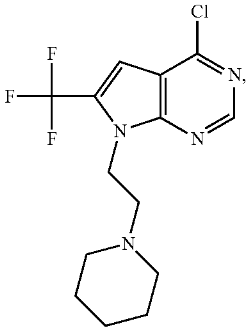
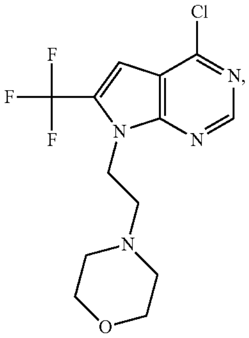
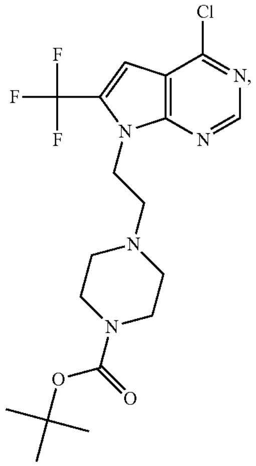
-continued
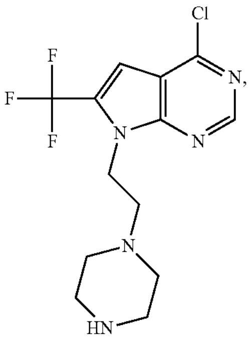
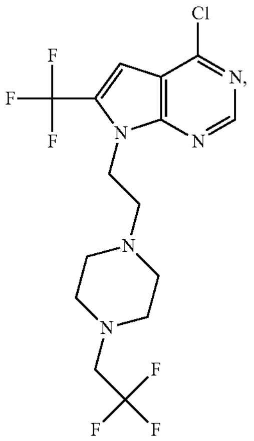
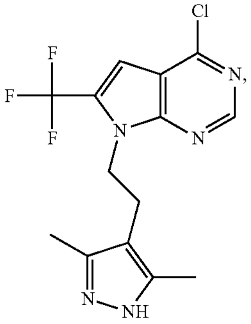
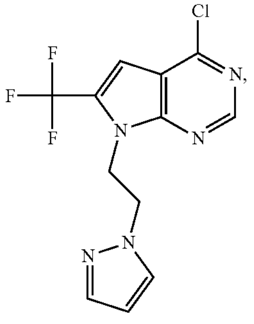
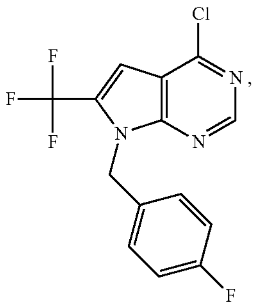
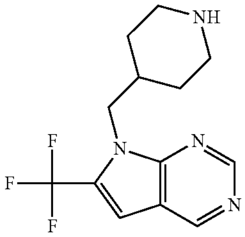
,
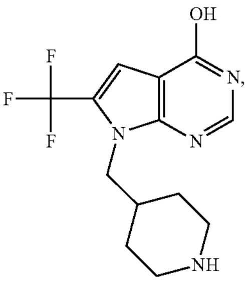
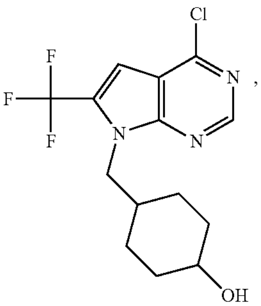
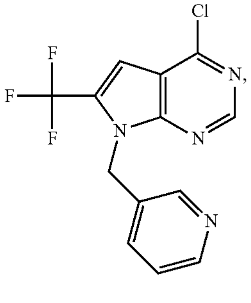
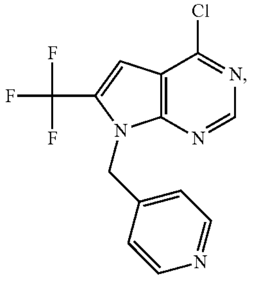

-continued
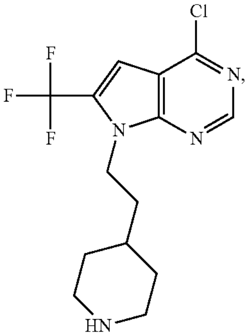
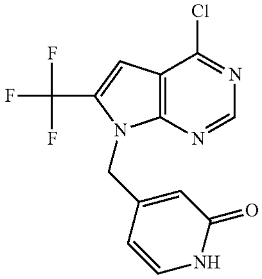
,
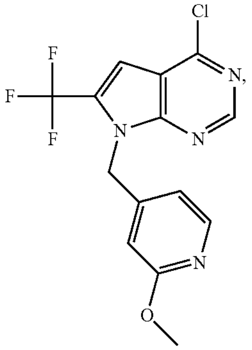
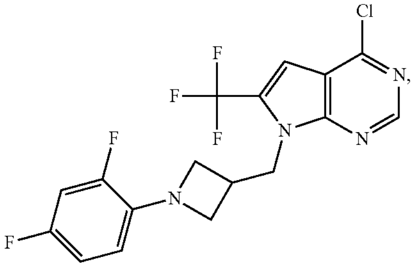
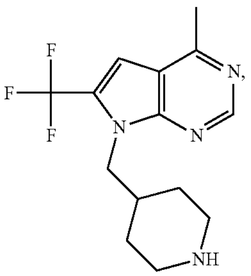
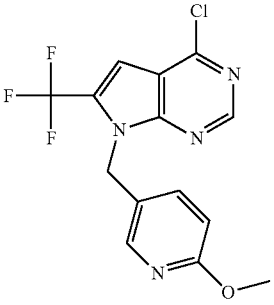
,
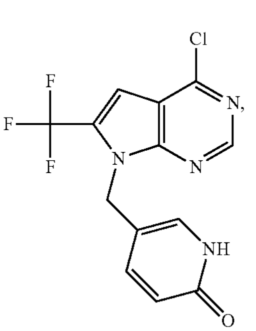
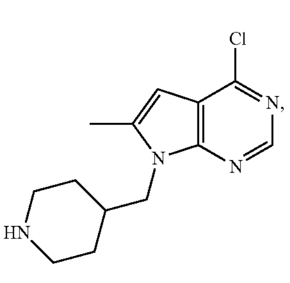
-continued
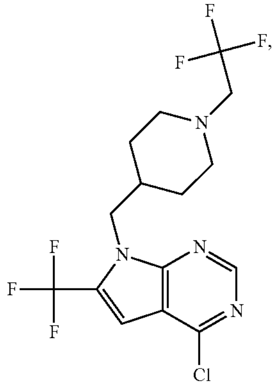
and
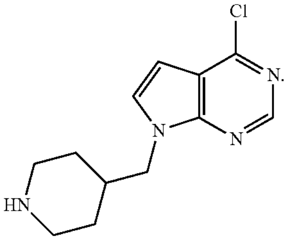
Embodiment 12. The compound of embodiments 1, wherein the compound is selected from
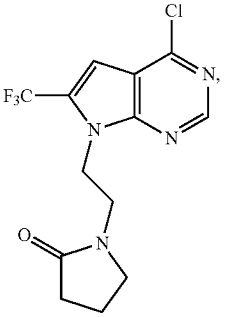
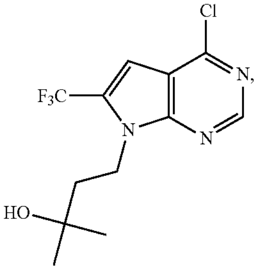
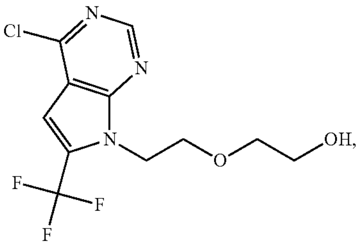
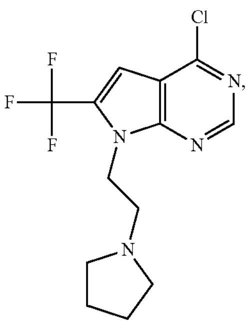

-continued
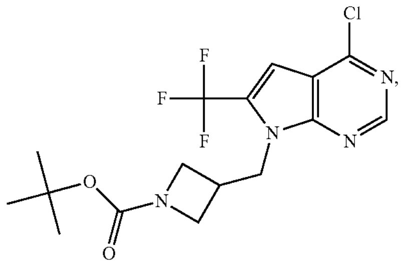
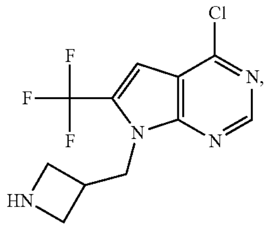
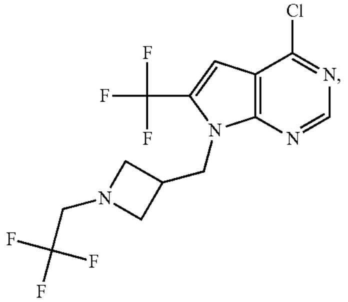
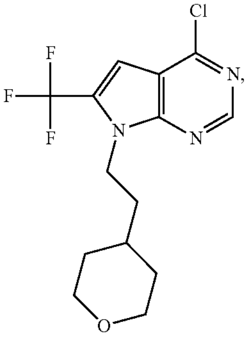
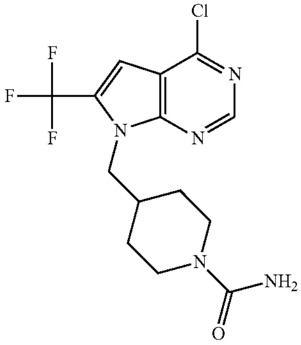
,
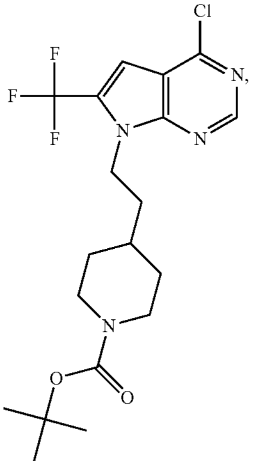
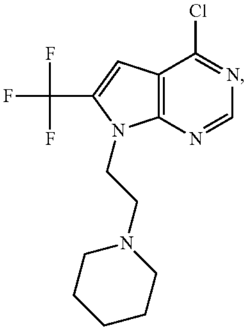
-continued
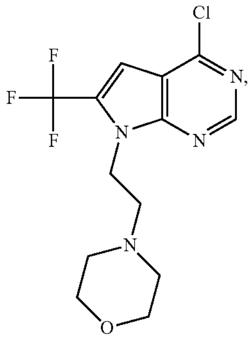
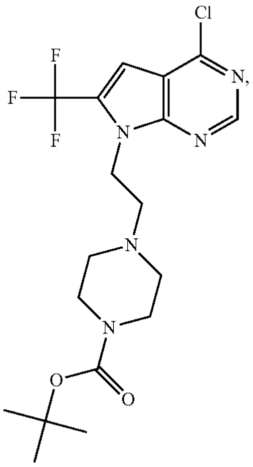
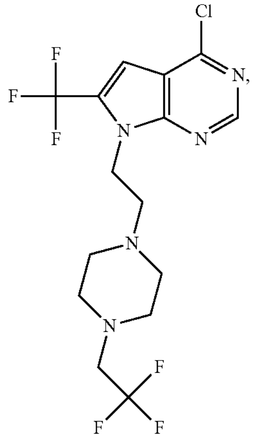
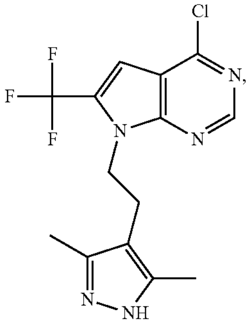
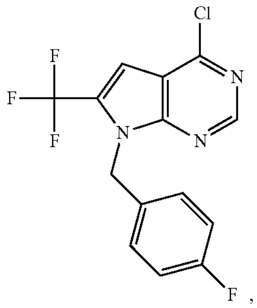
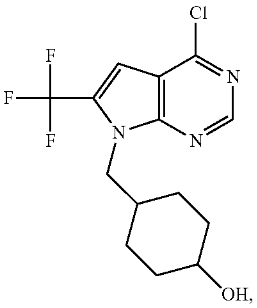
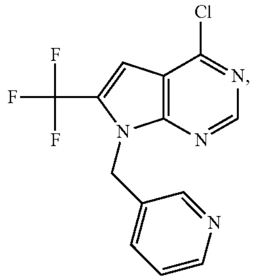
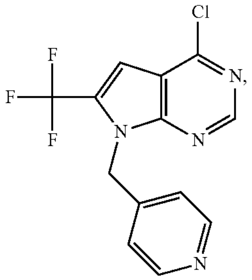

-continued
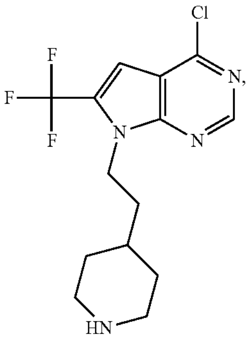
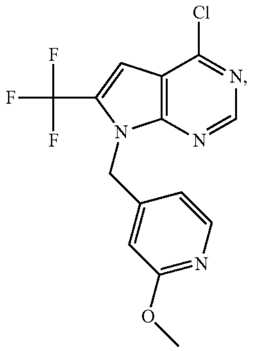
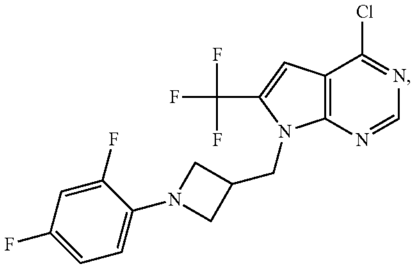
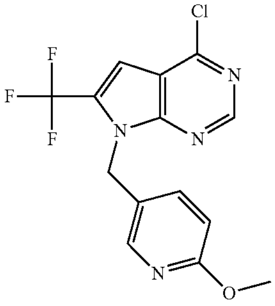
,
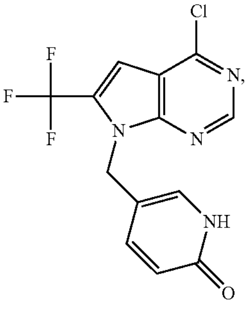
and
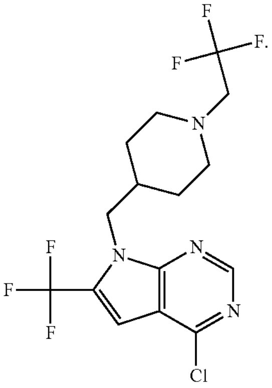 [SMILES: FC(F)(F)CN1CCC(Cn2c(C(F)(F)F)cc3c(Cl)ncnc32)CC1]
Embodiment 13. The compound of embodiment 1, wherein the compound is selected from
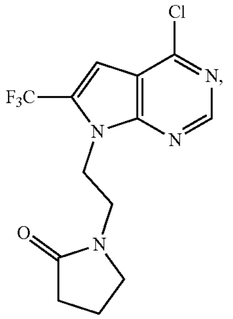
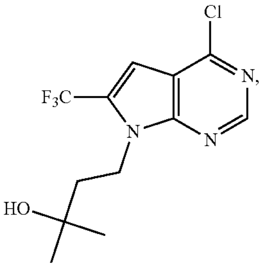
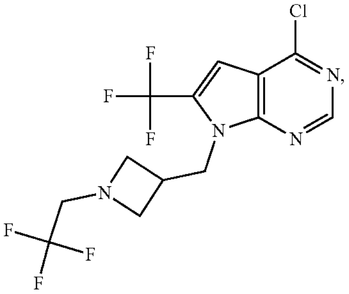
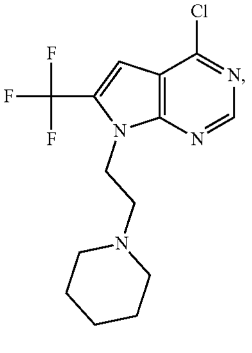
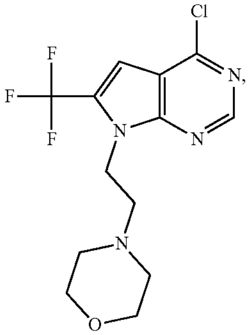
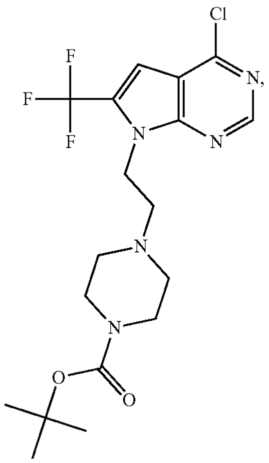
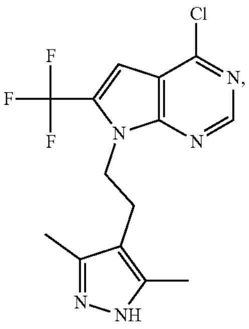

-continued

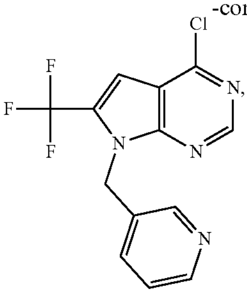

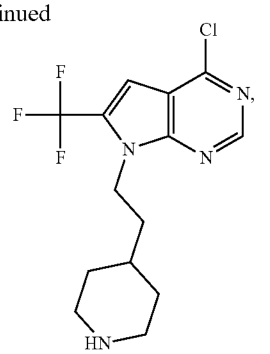

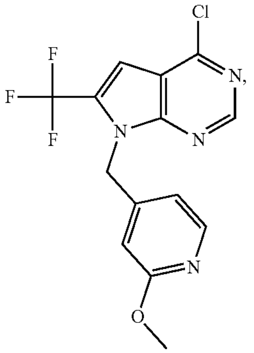

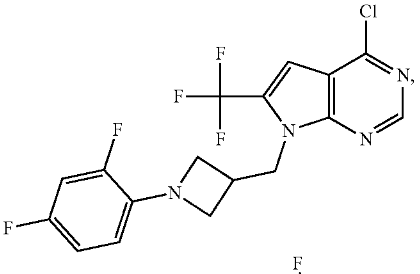

and

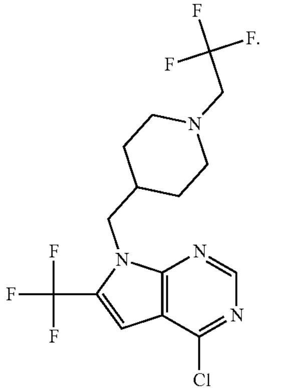

Embodiment 14. A pharmaceutical composition comprising an effective amount of compound according to any one of embodiments 1-13 or a pharmaceutically salt thereof, and a suitable pharmaceutical carrier, excipient, or diluent.

Embodiment 15. A method of treating cancer in a subject in need thereof, the method comprising administering the composition of embodiment 13 to the subject.

Embodiment 16. The method of embodiment 14, wherein the cancer is a leukemia.

Embodiment 17. The method of embodiment 14, wherein the cancer is acute myeloid leukemia.

Embodiment 18. A method of inhibiting cell proliferation, the method comprising contacting cells with the compound according to any one of embodiments 1-13.

Embodiment 19. The method of embodiment 18, wherein in the cells are leukemia cells.

Embodiment 20. The method of embodiment 18, wherein the cells are acute myeloid leukemia cells.

EXAMPLES

The following Examples are illustrative and are not intended to limit the scope of the claimed subject matter.

Example 1—Synthesis of Substituted Heterocycles for Treating Cancer

General Experimental

Scheme 1: Synthesis of Core A1-001, 002, 003, 004, 006, 011, 013, 014, 020, 022, 024, 028, 029, 032, 034 and 035.

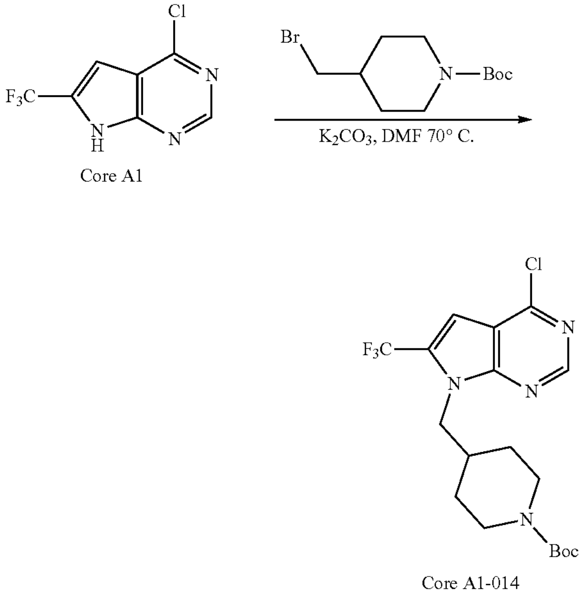

Core A1-014 may be used as an example.

Scheme 2: Synthesis of Core A1-007, 009, 014A, 016, 017, 018, and 021.

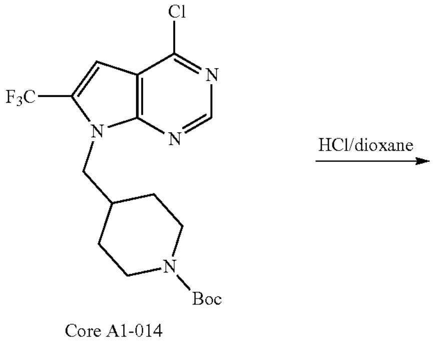

-continued
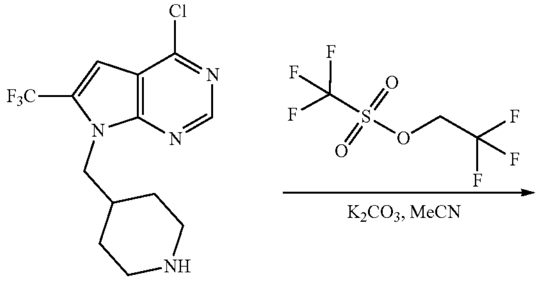
1
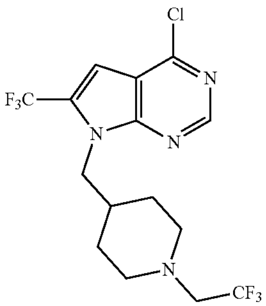
Core A1-014A
Core A1-014A may be used as an example.
Scheme 3: Synthesis of Core A1-022
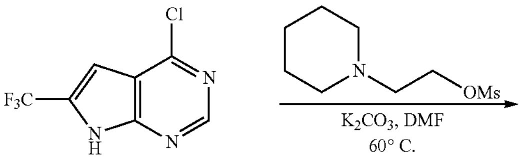
Core A1
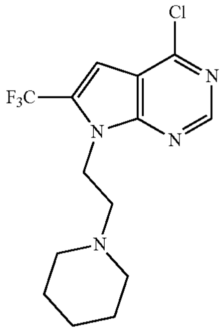
Core A1-022
Scheme 4: Synthesis of Core A1-025, Core A1-026 and Core A1-027.
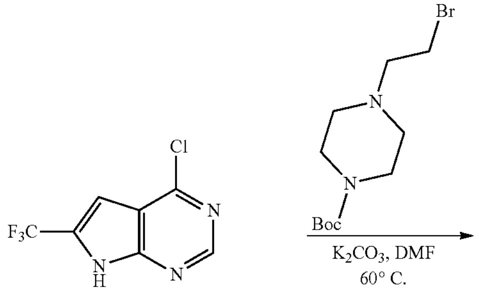
Core A1
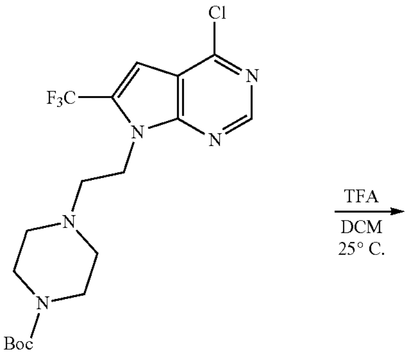
Core A1-025
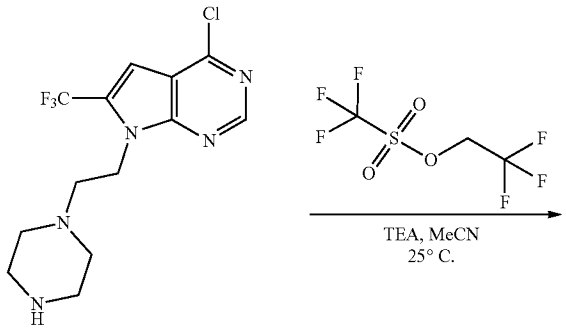
Core A1-026
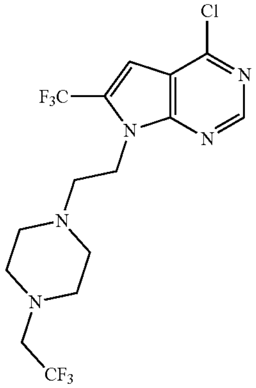
Core A1-027

Scheme 5: Synthesis of Core A1-037
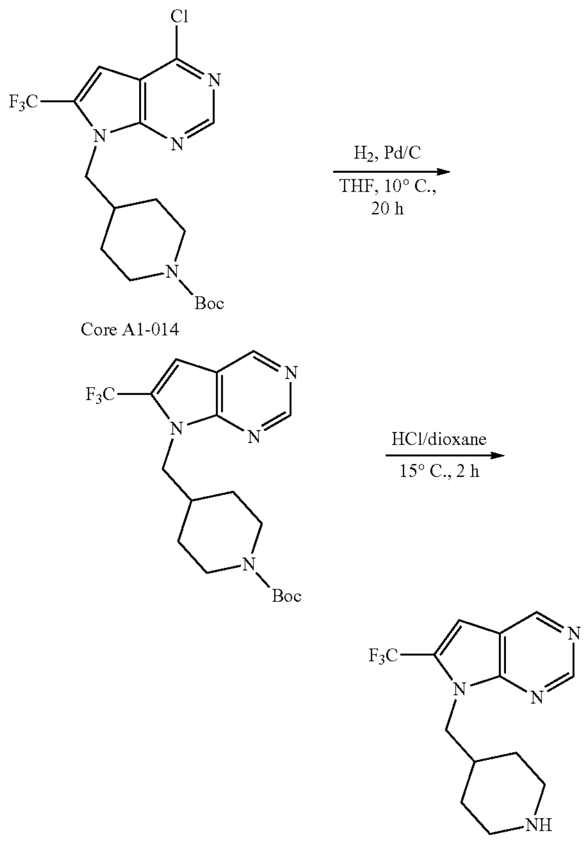
Core A1-014
Core A1-037
Scheme 6: Synthesis of Core A1-038
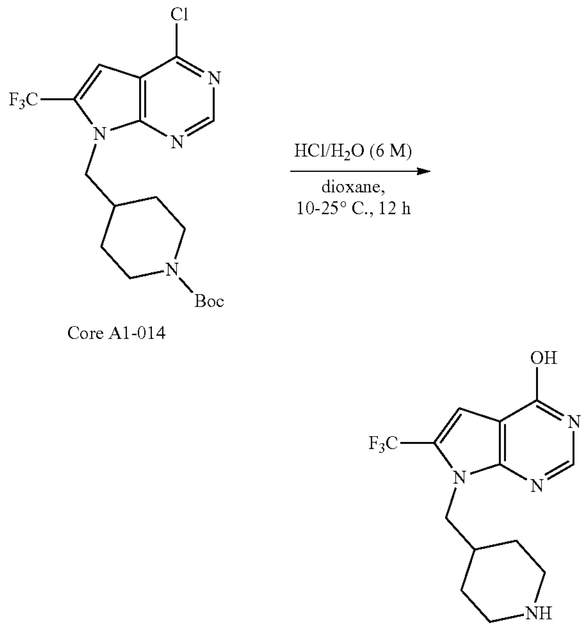
Core A1-014
Core A1-038
Scheme 7: Synthesis of Core A1-041
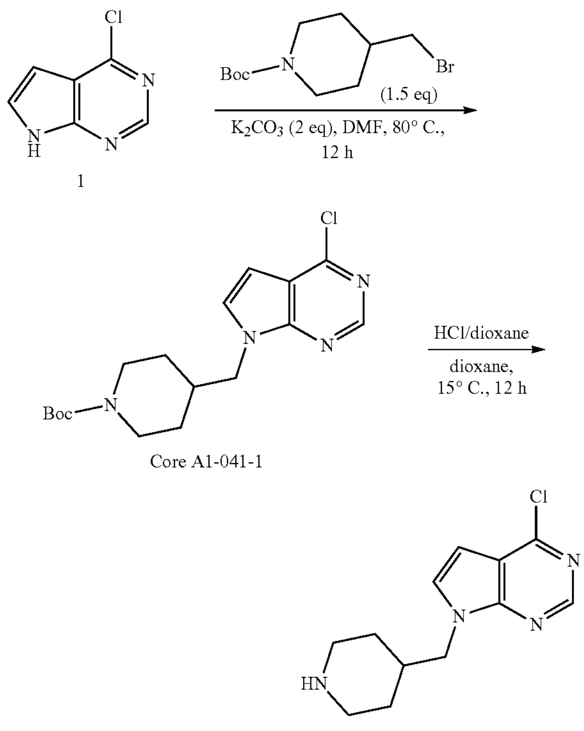
1
Core A1-041-1
Core A1-041
Scheme 8: Preparation of CoreA1-012.
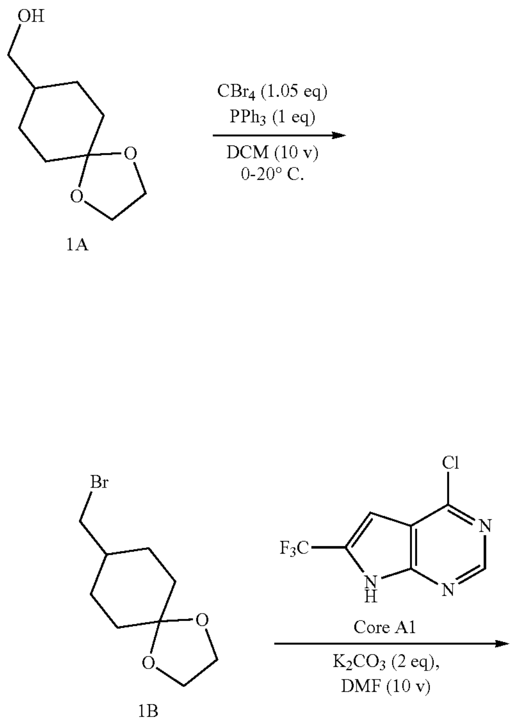
1A
1B -continued
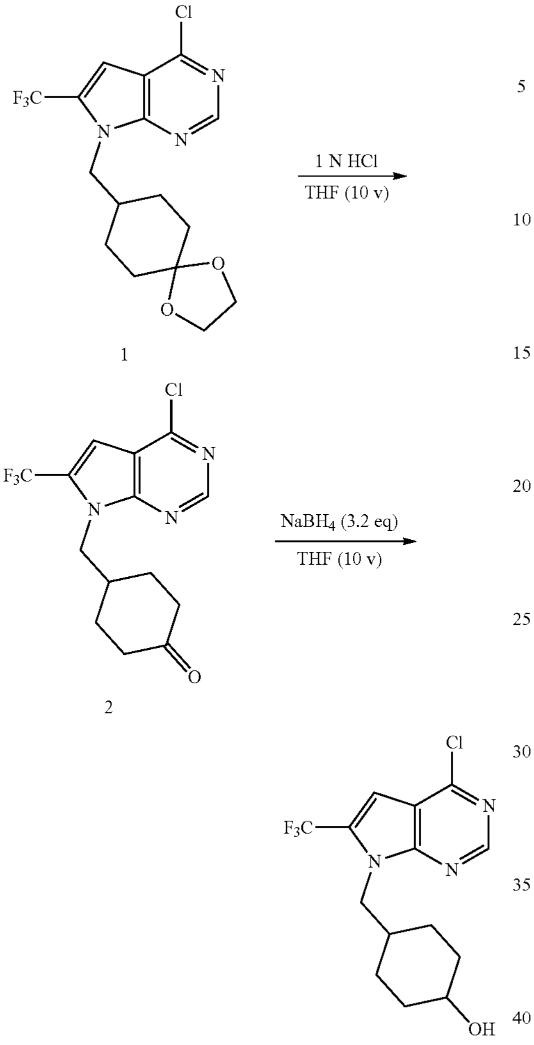
1
2
Core A1-012
Scheme 9: Preparation of CoreA1-010
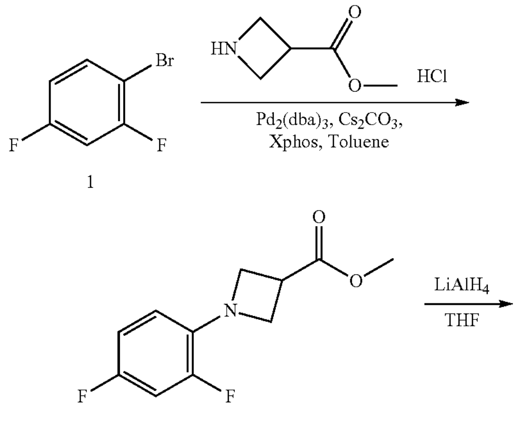
1
2
-continued
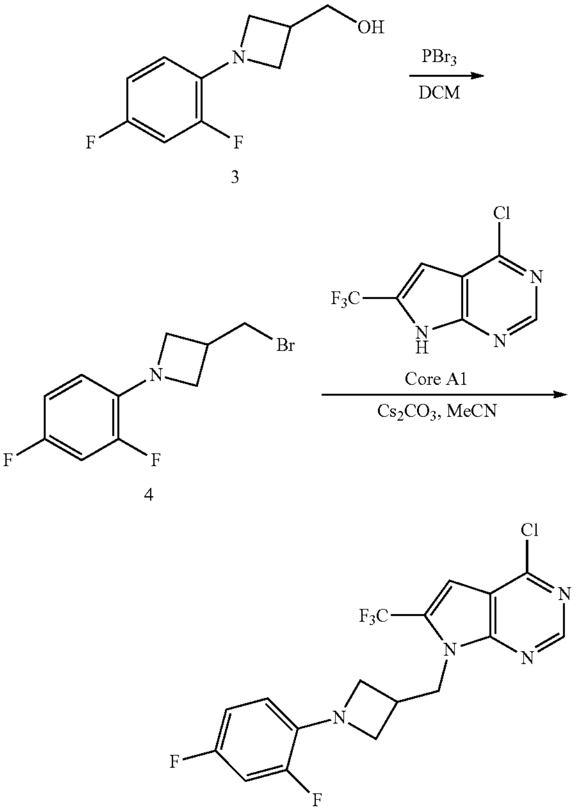
3
4
Core A1-010
Scheme 10: Preparation of CoreA1-030
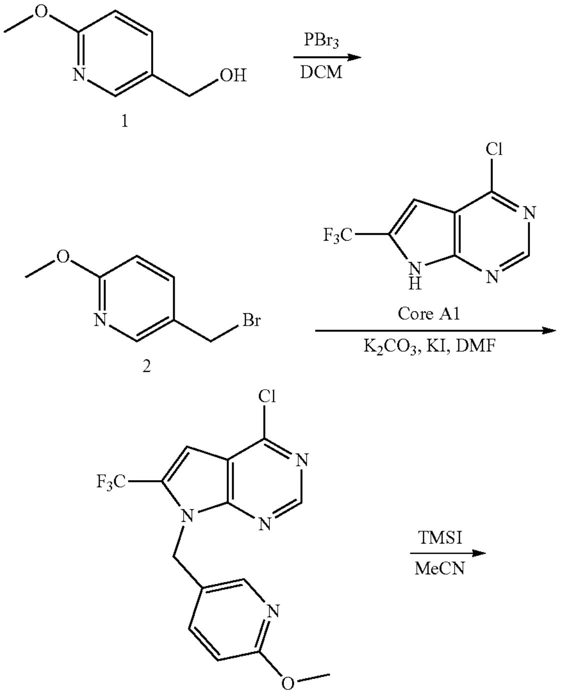
1
2
Core A1-030_3

-continued
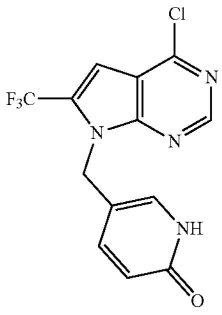
Core A1-030
Scheme 11: Preparation of CoreA1-031
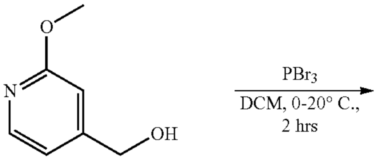
1
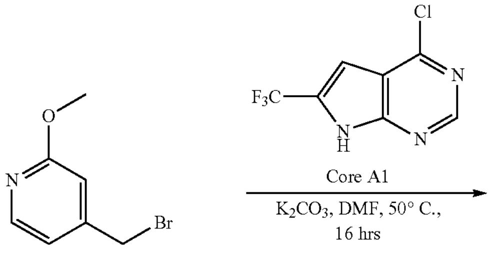
2
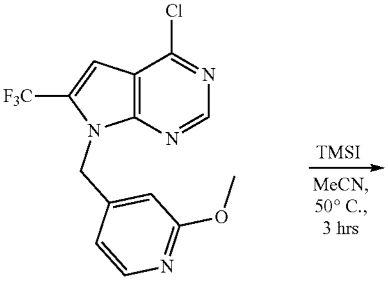
Core A1-031_3
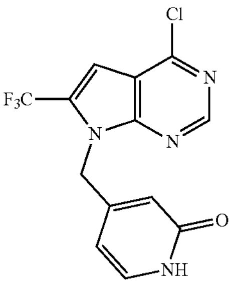
Core A1-031
Scheme 12: Preparation of CoreA1-036
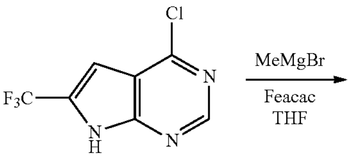
Core A1
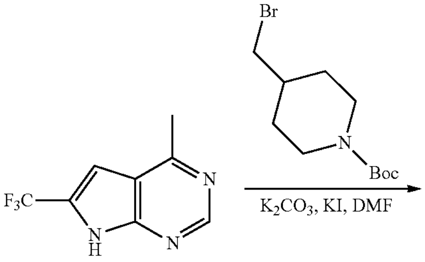
Core B
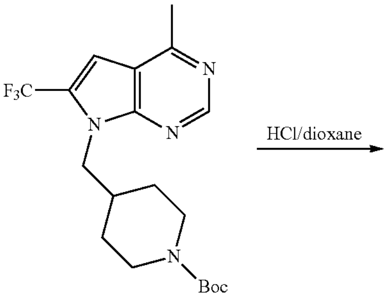
36-1
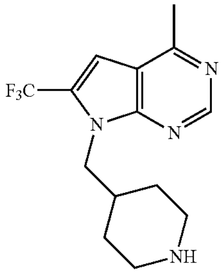
Core A1-036
Scheme 13: Preparation of CoreA1-042
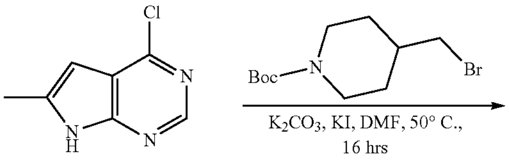
1

-continued

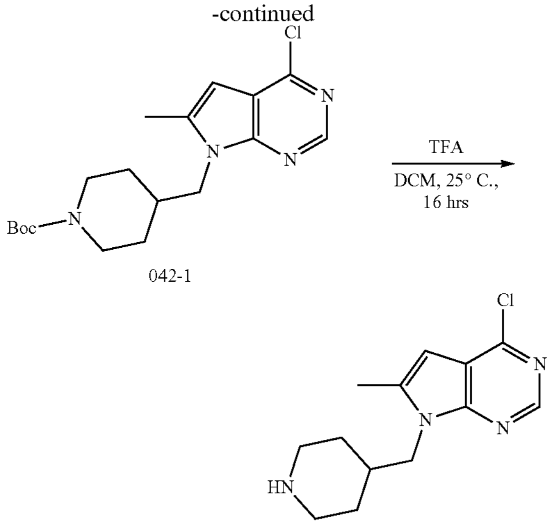

042-1

Core A1-042

Experimentals for Largest Scale Run

General Procedure for Preparation of Core A1

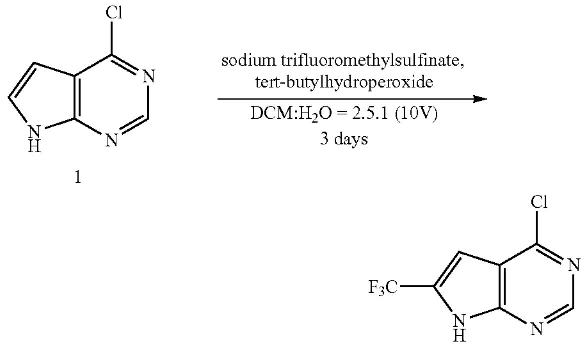

1

Core A1

To a suspension of Compound 1 (5 g, 32.56 mmol, 1 eq) in a mixture of DCM (150 mL)/H2O (60 mL) was added sodium trifluoromethylsulfinate (16.80 g, 97.64 mmol, 3 eq) at 0° C. 10 minutes later, tert-butylhydroperoxide (20.96 g, 162.79 mmol, 22.30 mL, 70% purity, eq) was added dropwise at 0° C. And then the reaction mixture was stirred at 20° C. for 72 h. After that, the mixture was quenched by addition of saturated aqueous $NaHCO_3$ (200 mL). The aqueous layer was extracted with DCM (2×100 mL). The combined organic layers were washed with saturated aqueous $NaHSO_3$ solution (100 ml) and dried over $Na_2SO_4$, filtered and concentrated to give the residue. The residue was purified by silica gel chromatography (eluted with petroleum ether:ethyl acetate=10:1) to give Core A1 (4.1 g, 34.10% yield) as white solid.

LCMS (ESI+): m/z 222.0 $(M+H)^+$, RT: 0.687 min.

LC/MS (The gradient was 5-95% B in 1.0 min, 95-100% B in 0.80 min, 100-5% B in 0.01 min, and then held at 5% B for 0.39 min (1.0 mL/min flow rate). Mobile phase A was 0.0375% CF3CO2H in water, mobile phase B was 0.018% CF3CO2H in $CH_3CN$. The column used for the chromatography was a ZORBAX Eclipse XDB-C18 2.1*30 mm, 3.5 um. Detection methods are diode array (DAD) and positive electrospray ionization (MS).)

General Procedure for Preparation of Core A1-014

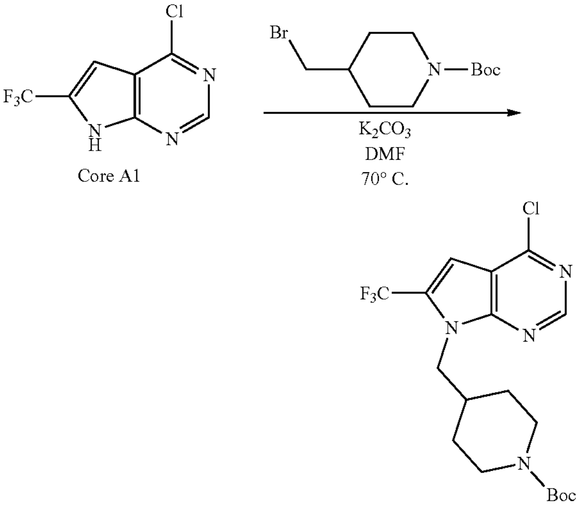

Core A1

Core A1-014

To a mixture of Core A1 (0.1 g, 451.33 umol) and tert-butyl 4-(bromomethyl) piperidine-1-carboxylate (188.33 mg, 677.00 umol) in N, N-dimethylformamide (1 mL) was added $K_2CO_3$ (124.76 mg, 902.66 umol) in one portion at 20° C. The mixture was stirred at 70° C. for 1 h. The mixture was cooled down to 20° C. After filtered, the filtration was purified by prep-HPLC to give Core A1-014 (0.021 g, 11% yield) as yellow solid.

Prep-HPLC Method

Instrument: Shimadzu LC-8A preparative HPLC
Column: Phenomenex luna C18 80*40 mm*3 um
Mobile phase: A for $H_2O$ (0.09% trifluoroacetic acid) and B for $CH_3CN$
Gradient: B from 32% to 50% in 20 min
Flow rate: 40 mL/min
Wavelength: 220&254 nm

| Time | B % |
|---|---|
| 0.0 | 15 |
| 8.0 | 45 |
| 8.1 | 45 |
| 8.2 | 100 |
| 11.2 | 100 |
| 11.3 | 15 |
| 12.5 | 15 |

$^1H$ NMR: ET44912-12-P1G (400 MHz, $CDCl_3$) δ 1.24-1.35 (m, 2H), 1.41-1.51 (m, 11H), 2.06-2.30 (m, 1H), 2.50-2.72 (m, 2H), 3.98-4.19 (m, 2H), 4.20-4.39 (m, 2H), 7.04-7.17 (m, 1H), 8.67-8.89 (m, 1H)

LCMS (ESI+): m/z 363.0 (M+H)+, RT: 3.174 min.

5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% trifluoroacetic acid in water, mobile phase B was 0.02% trifluoroacetic acid in acetonitrile. The column used for chromatography was a Luna C18 50*2.0 mm column (Sum particles). Detection methods are diode array (DAD) and evaporative light scattering (ELSD) detection as well as positive electrospray ionization. MS range was 100-1000.

General Procedure for Preparation of Core A1-014A

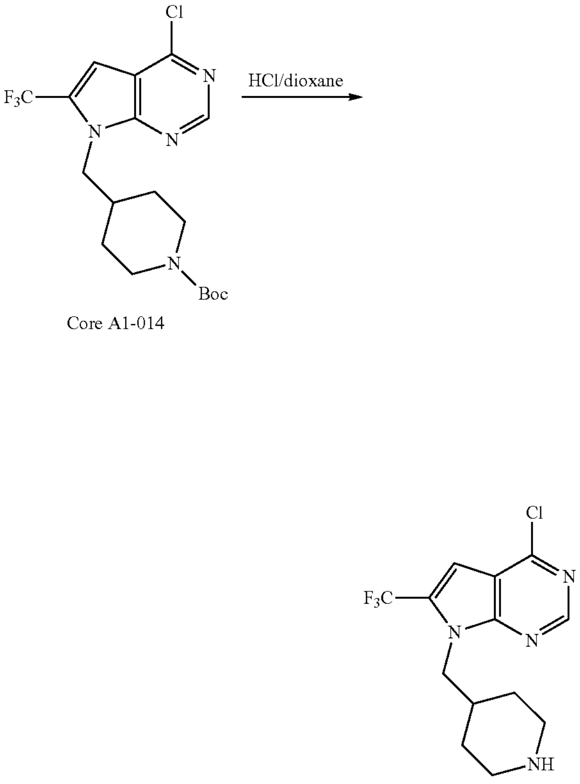

Core A1-014

1

To a mixture of Core A1-014 (1 g, 2.39 mmol) in dioxane (10 mL) was added HCl/dioxane (4 M, 10.0 mL) in one portion at 20° C. The mixture was stirred at 25° C. for 0.5 h. The mixture was concentrated under reduced pressure to give Compound 1 (0.7 g, 91% yield) as white solid, which was used directly to next step without further purification.

LCMS (ESI+): m/z 319.0 (M+H)+, RT: 0.597 min

LC/MS (The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% trifluoroacetic acid in water, mobile phase B was 0.018% trifluoroacetic acid in $CH_3CN$. The column used for the chromatography is a Chromolith Flash RP-18e 25-2 mm column. Detection methods are diode array (DAD) and evaporative light scattering (ELSD) detection as well as positive electrospray ionization (MS).)

General Procedure for Preparation of Core A1-014A

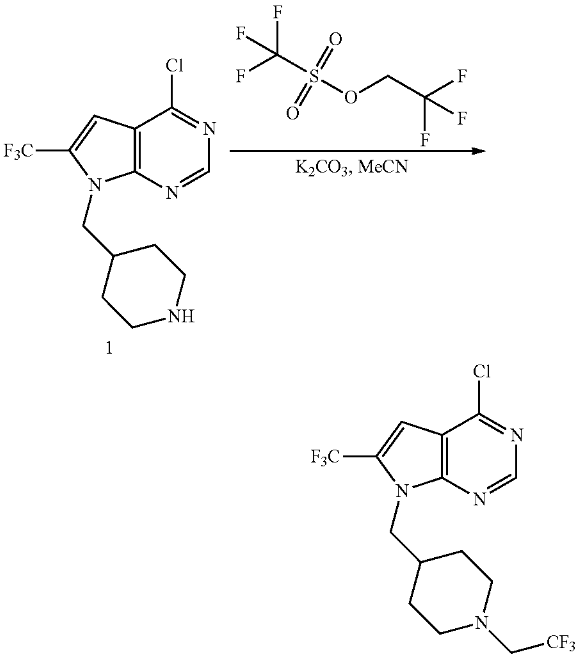

1

Core A1-014A

To a mixture of Compound 1 (0.1 g, 313.75 umol) in acetonitrile (5 mL) was added 2,2,2-trifluoroethyl trifluoromethanesulfonate (145.64 mg, 627.50 umol) and $K_2CO_3$ (130.09 mg, 941.25 umol) in one portion at 20° C. The mixture was stirred at 70° C. for 1 h. After cooled down to 25° C., the mixture was concentrated under reduced pressure directly to give a residue. The residue was purified by prep-HPLC to give Core A1-014A (28.2 mg, 22% yield) as white solid.

Prep-HPLC Method

Instrument: Gilson 281 semi-preparative HPLC system
Mobile phase: A: trifluoroacetic acid/$H_2O$=0.075% v/v; B: $CH_3CN$
Column: Phenomenex Luna 80*30 mm*3 um
Flow rate: 25 mL/min
Monitor wavelength: 220&254 nm

| Time | B % |
|---|---|
| 0.0 | 15 |
| 8.0 | 45 |
| 8.1 | 45 |
| 8.2 | 100 |
| 11.2 | 100 |
| 11.3 | 15 |
| 12.5 | 15 |

$^1H$ NMR: ET44912-31-PIF (400 MHz, $CDCl_3$) δ 1.63-1.91 (m, 4H), 2.18-2.36 (m, 1H), 2.66-2.85 (m, 2H), 3.34-3.57 (m, 4H), 4.24-4.41 (m, 2H), 7.02-7.16 (m, 1H), 8.71-8.82 (m, 1H), 12.41-13.00 (m, 1H)

LCMS (ESI+): m/z 401.0 (M+H)+, RT: 2.442 min.

5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

General Procedure for Preparation of Core A1-022

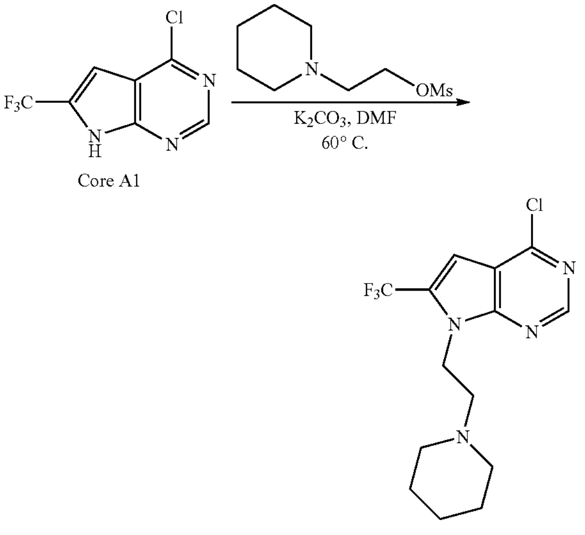

Core A1

Core A1-022

To a mixture of Core A1 (0.06 g, 271 umol) in dimethyl formamide (1.5 mL) was added $K_2CO_3$ (56.1 mg, 406 umol) and 2-(1-piperidyl) ethyl methanesulfonate (168 mg, 812 umol) at 20° C. under N2. The mixture was stirred at 60° C. for 2 h. The mixture was cooled down to 20° C. After filtered, the filtration was purified by prep-HPLC to give Core A1-022 (40 mg, 44% yield) as yellow solid Prep-HPLC Method Instrument: Gilson 281 semi-preparative HPLC system
Mobile phase: A: 10 mM $NH_4HCO_3$ in $H_2O$; B: $CH_3CN$
Column: Phenomenex C18 75*30 mm*3 um
Flow rate: 25 mL/min
Monitor wavelength: 220&254 nm

| Time | B % |
|---|---|
| 0.0 | 40 |
| 12.0 | 65 |
| 12.1 | 65 |
| 12.2 | 100 |
| 14.2 | 100 |
| 14.3 | 40 |
| 15.5 | 40 |

$^1$H N M R: ET44912-29-P1J3 (400 MHz, $CDCl_3$) δ ppm 1.44 (br d, J=4.77 Hz, 2H) 1.56 (br s, 4H) 2.52 (br s, 4H) 2.75 (br t, J=7.27 Hz, 2H) 4.53 (br t, J=7.46 Hz, 2H) 7.05 (s, 1H) 8.76 (s, 1H)

LCMS (ESI+): m/z 333.1 (M+H)+, RT: 3.477 min.

5_95 CD_6 min-220-254-ELSD: LC/MS (The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge-C18 2.1*50 mm column (Sum particles). Detection methods are diode array (DAD) and evaporative light scattering (ELSD) detection as well as positive electrospray ionization. MS range was 100-1000.

General Procedure for Preparation of Core A1-025

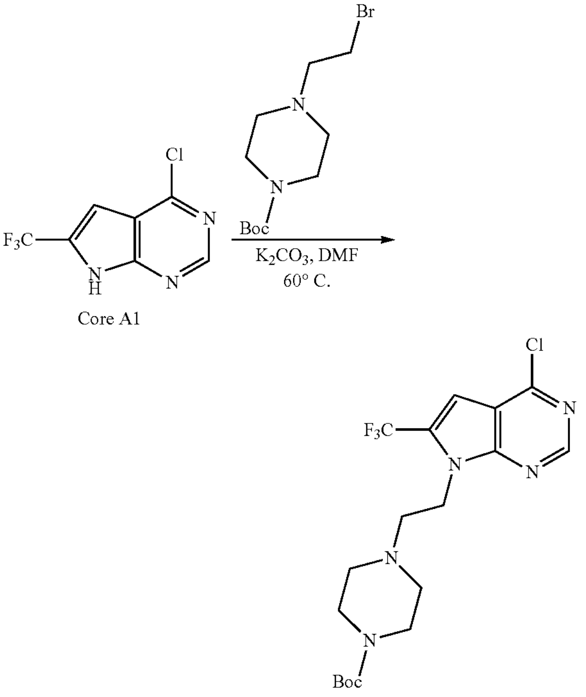

Core A1

Core A1-025

To a mixture of Core A1 (0.1 g, 451 umol) in dimethyl formamide (3 mL) was added $K_2CO_3$ (93.6 mg, 677 umol) and tert-butyl 4-(2-bromoethyl) piperazine-1-carboxylate (265 mg, 903 umol) at 20° C. under N2. The mixture was stirred at 60° C. for 2 h. The mixture was cooled down to 20° C. After filtered, the filtration was purified by prep-HPLC to give Core A1-025 (70 mg, 35% yield) as yellow solid.

Prep-HPLC Method

Instrument: Shimadzu LC-8A preparative HPLC
Column: Phenomenex C18 80*40 mm*3 um
Mobile phase: A for $H_2O$ (10 mM $NH_4HCO_3$) and B for $CH_3CN$
Gradient: B from 45% to 75% in 20 min
Flow rate: 60 mL/min
Wavelength: 220&254 nm
$^1$H NMR: ET44912-60-P1H3 (400 MHz, $CDCl_3$) δ 1.45 (s, 9H), 2.50 (br s, 4H), 2.79 (br s, 2H), 3.36 (br s, 4H), 4.52 (br s, 2H), 7.06 (s, 1H), 8.75 (s, 1H)

LCMS (ESI+): m/z 434.2 (M+H)+, RT: 3.522 min.

5_95CD_6 min-220-254-ELSD: LC/MS (The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was $H_2O$+10 mM $NH_4HCO_3$, mobile phase B was Acetonitrile. The column used for chromatography was a Xbridge-C18 2.1*50 mm column (5 um particles). Detection methods are diode array (DAD) and evaporative light scattering (ELSD) detection as well as positive electrospray ionization. MS range was 100-1000.

General Procedure for Preparation of Core A1-026

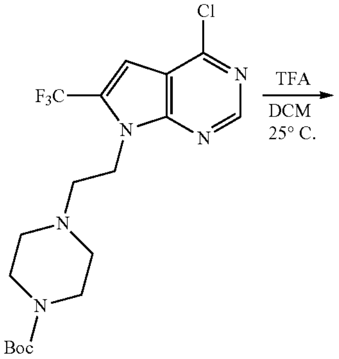

Core A1-025

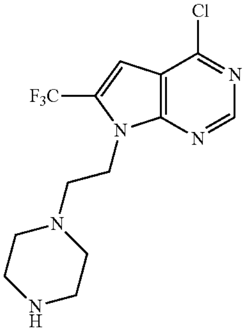

Core A1-026

Trifluoroacetic acid (2.96 g, 25.9 mmol) was added to a solution of Core A1-025 (240 mg, 553 umol) in dichloromethane (9.6 mL). The mixture was stirred at 25° C. for 2 h. After concentrated under reduced pressure, the residue was purified by prep-HPLC to give Core A1-026 (110 mg, 57% yield) as yellow solid.

Prep-HPLC Method

Instrument: Gilson 281 semi-preparative HPLC system
Mobile phase: A: $TFA/H_2O$=0.075% v/v; B: $CH_3CN$
Column: Phenomenex Luna 80*30 mm*3 um
Flow rate: 25 mL/min
Monitor wavelength: 220&254 nm

| Time | B % |
|---|---|
| 0.0 | 1 |
| 8.0 | 30 |
| 8.1 | 30 |
| 8.2 | 100 |

-continued

| Time | B % |
|---|---|
| 11.2 | 100 |
| 11.3 | 1 |
| 12.5 | 1 |

$^1$H NMR: ET44912-76-P1H (400 MHz, MeOD) δ 2.81 (br s, 4H), 2.91 (s, 2H), 3.09 (t, J=5.07 Hz, 4H), 4.60 (s, 2H), 7.27-7.31 (m, 1H), 8.77 (s, 1H)

LCMS (ESI+): m/z 334.0 (M+H)+, RT: 1.790 min.

5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

General Procedure for Preparation of Core A1-027

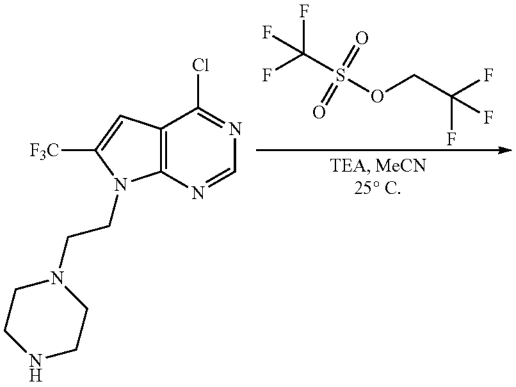

Core A1-026

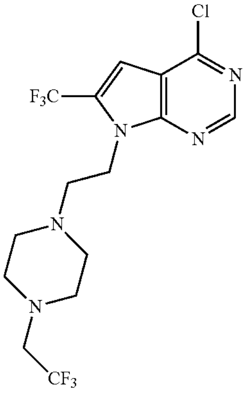

Core A1-027

A solution of Core A1-026 (100 mg, 300 umol) in $CH_3CN$ (1 mL) was added to a solution of 2,2,2-trifluoroethyl trifluoromethanesulfonate (209 mg, 899 umol) and triethylamine (303 mg, 3.00 mmol) in $CH_3CN$ (1 mL). The resulting mixture was stirred at 25° C. for 12 h. After concentrated under reduced pressure, the residue was purified by prep-HPLC to give Core A1-027 (18.7 mg, 15% yield) as white solid.

Prep-HPLC Method

Instrument: Gilson 281 semi-preparative HPLC system
Mobile phase: A: 10 mM $NH_4HCO_3$ in $H_2O$; B: $CH_3CN$
Column: Waters Xbridge BEH C18 100*30 mm*10 um
Flow rate: 25 mL/min
Monitor wavelength: 220&254 nm

| Time | B % |
|---|---|
| 0.0 | 55 |
| 8.0 | 75 |
| 8.1 | 75 |
| 8.2 | 100 |
| 10.2 | 100 |
| 10.3 | 55 |
| 11.5 | 55 |

$^1H$ NMR: ET44912-77-P1H1 (400 MHz, $CDCl_3$) δ 2.55 (br s, 8H), 2.71 (br s, 2H), 2.80-2.91 (m, 2H), 4.43 (br s, 2H), 6.99 (s, 1H), 8.68 (s, 1H))

LCMS (ESI+): m/z 416.0 (M+H)+, RT: 1.972 min.

5_95 CD_6 min-220-254-ELSD: LC/MS (The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge-C18 2.1*50 mm column (5 um particles). Detection methods are diode array (DAD) and evaporative light scattering (ELSD) detection as well as positive electrospray ionization. MS range was 100-1000.

General Procedure for Preparation of Compound 1

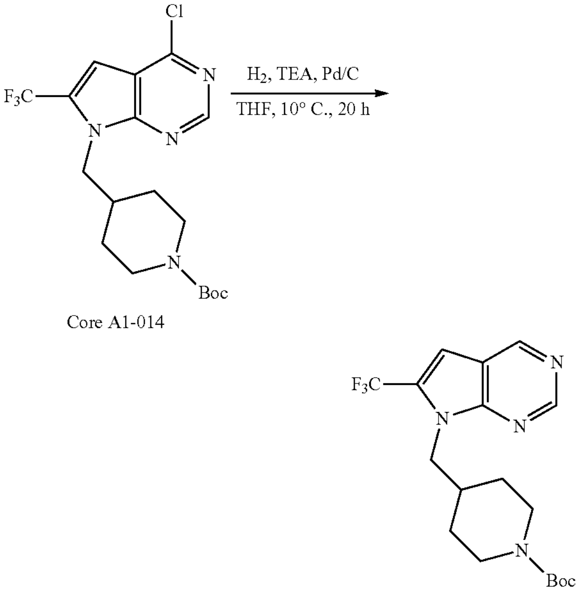

Core A1-014

1

To a mixture of Core A1-014 (0.25 g, 597 umol, 1 eq) in THF (12 mL) was added TEA (2.49 mL, 17.9 mmol, 30 eq) and Pd/C (150 mg, 10% purity) at 20° C. The mixture was stirred at 20° C. for 20 h under $H_2$ (15 psi) atmosphere. The mixture was filtered and the filtrate was concentrated to give Compound 1 (0.25 g, 90% yield) as light yellow solid.

LCMS (ESI+): m/z 385.2 (M+H)+, RT: 0.625 min

LCMS Method: LC/MS (The column used for chromatography was a Kinetex 5 μm EVO C18 100A 2.1*30 mm. Detection methods are diode array (DAD). MS mode was positive electrospray ionization. MS range was 100-1000. Mobile phase A was 0.04% trifluoroacetic acid in water, and mobile phase B was 0.02% trifluoroacetic acid in HPLC grade acetonitrile. The gradient was 5-95% B in 1.50 min 0.5% B in 0.01 min, 5-95% B (0.01-0.70 min), 95% B for 0.46 min. 95-5% B (1.61-1.50 min) with a hold at 5% B for 0.11 min. The flow rate was 1.5 mL/min.

General Procedure for Preparation of Core A1-037

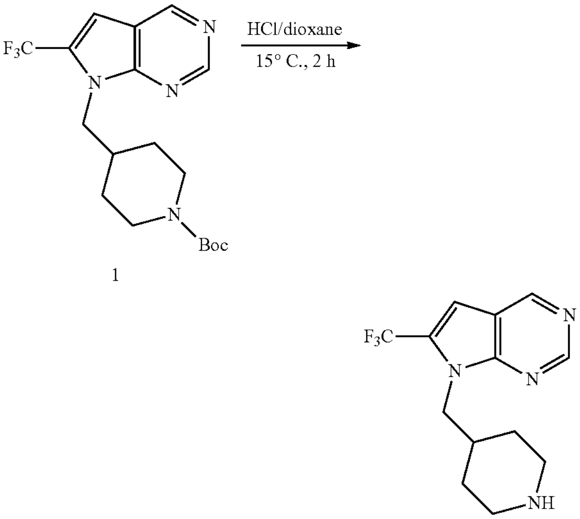

1

Core A1-037

To a mixture of Compound 1 (0.25 g, 650 umol, 1 eq) in dioxane (2 mL) was added HCl/dioxane (4 M, 5 mL, 30.7 eq). The mixture was stirred at 15° C. for 2 h. The mixture was concentrate and the residue was purified by prep-HPLC to give Core A1-037 (20 mg, 9% yield, HCl salt) as white solid.

Prep-HPLC Method

Instrument: Gilson 281 semi-preparative HPLC system
Mobile phase: A: 10 mM $NH_4HCO_3$ in $H_2O$; B: $CH_3CN$
Column: Phenomenex C18 75*30 mm*3 um
Flow rate: 25 mL/min
Monitor wavelength: 220&254 nm

| Time | B % |
|---|---|
| 0.0 | 15 |
| 8.0 | 45 |
| 8.1 | 45 |
| 8.2 | 100 |
| 10.2 | 100 |
| 10.3 | 15 |
| 11.5 | 15 |

$^1$H NMR (400 MHz, DMSO-d6) δ 1.14 (qd, J=12.04, 3.85 Hz, 2H), 1.30 (br d, J=11.25 Hz, 2H), 1.99-2.13 (m, 1H), 2.28-2.37 (m, 2H), 2.87 (br d, J=12.10 Hz, 2H), 4.22 (br d, J=7.70 Hz, 2H), 7.38 (s, 1H), 9.02 (s, 1H), 9.23 (s, 1H)

LCMS (ESI+): m/z 285.0 $(M+H)^+$, RT: 0.644 min

LCMS Method: LC/MS (The gradient was 5% B at 0.00 min and 5-90% B at 0.0-0.8 min, 90%-95% B at 0.80-1.20 min and then 95-5% B in 0.01 min, the flow rate was 1.5 ml/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) as well as positive electrospray ionization. MS range was 100-1000.

General Procedure for Preparation of Core A1-038

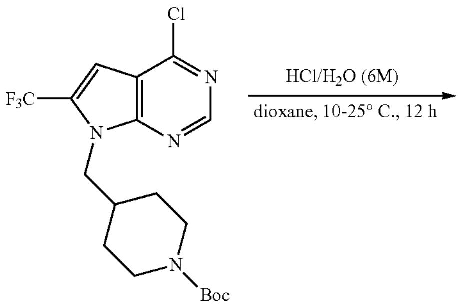

Core A1-014

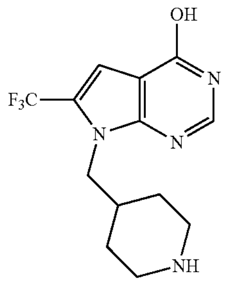

Core A1-038

To a mixture of Core A1-014 (100 mg, 239 umol, 1 eq) in dioxane (2 mL) was added $HCl/H_2O$ (6 M, 1.5 mL, 18.8 eq) at 10° C. The mixture was stirred at 25° C. for 12 h. The mixture was purified by prep-HPLC to afford Core A1-038 (69 mg, 84% yield, HCl salt) as white solid.

Prep-HPLC Method

Instrument: Shimadzu LC-8A preparative HPLC
Column: Phenomenex luna C18 80*40 mm*3 um
Mobile phase: A for $H_2O$=(0.04% HCl) and B for $CH_3CN$
Gradient: B from 3% to 27% in 20 min
Flow rate: 40 mL/min
Wavelength: 220&254 nm $^1$H NMR ET44973-51-H1 (400 MHz, DMSO-d6) δ ppm 1.40-1.64 (m, 4H) 2.10-2.24 (m, 1H) 2.78 (q, J=11.45 Hz, 2H) 3.21 (br d, J=12.47 Hz, 2H) 4.13 (br d, J=7.58 Hz, 2H) 7.17 (s, 1H) 8.12 (d, J=3.42 Hz, 1H) 8.74-9.09 (m, 2H) 12.34 (br s, 1H)

LCMS (ESI+): m/z 301.0 $(M+H)^+$, RT: 1.487 min

LCMS Method. LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

General Procedure for Preparation of Core-041-1

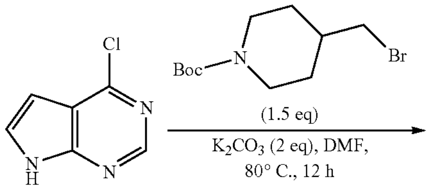

1

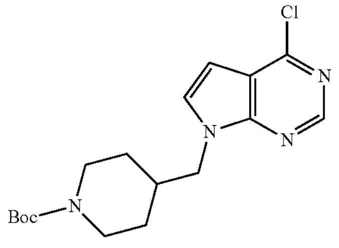

Core A1-041-1

To a mixture of Compound 1 (1.36 g, 4.88 mmol, 1.5 eq) in DMF (10 mL) was added $K_2CO_3$ (900 mg, 6.51 mmol, 2 eq). The mixture was stirred at 80° C. for 12 h. The mixture was cooled to 20° C. Then the reaction was quenched by addition of water (20 mL) and extracted with ethyl acetate (3×20 mL). The combined organic layers were washed with brine (20 mL), dried over anhydrous sodium sulfate and filtered. Then the organic mixture was concentrated and purified by flash column chromatography on silica gel (eluted with petroleum ether/ethyl acetate=100/1 to 1/100) to give Core A1-041-1 (0.8 g, 64% yield) as white solid.

$^1$H NMR ET44912-52-H1 (400 MHz, DMSO-d6) δ 1.08 (qd, J=12.26, 4.23 Hz, 2H), 1.36 (s, 9H), 1.42 (br s, 2H), 2.01-2.11 (m, 1H), 2.53-2.77 (m, 2H), 3.89 (br d, J=10.97 Hz, 2H), 4.18 (d, J=7.27 Hz, 2H), 6.65 (d, J=3.46 Hz, 1H), 7.76 (d, J=3.46 Hz, 1H), 8.62 (s, 1H)

General Procedure for Preparation of Core A1-041

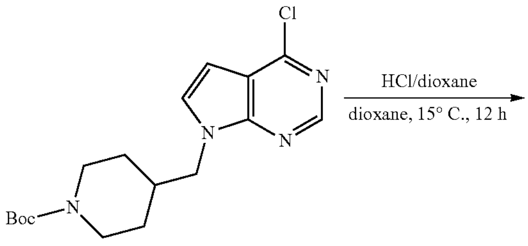

Core A1-041-1

-continued

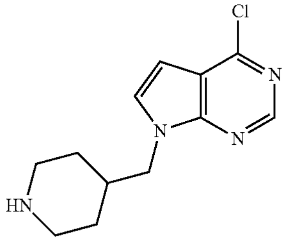

Core A1-041

To a mixture of Core A1-041-1 (0.5 g, 1.43 mmol, 1 eq) in dioxane (2 mL) was added HCl (g)/dioxane (4 M, 10.96 mL). The mixture was stirred at 15° C. for 2 h. Then the reaction mixture was filtered. The filter cake was dried under reduced pressure to afford Core A1-041 (66 mg, 16% yield, HCl salt) as white solid.

$^1$H NMR ET44912-58-H3 (400 MHz, DMSO-d6) δ ppm 1.37-1.51 (m, 2H), 1.54-1.65 (m, 2H), 2.16 (dtt, J=14.82, 7.40, 7.40, 3.53, 3.53 Hz, 1H), 2.69-2.86 (m, 2H), 3.20 (br d, J=12.59 Hz, 2H), 4.22 (d, J=7.21 Hz, 2H), 6.68 (d, J=3.55 Hz, 1H), 7.80 (d, J=3.55 Hz, 1H), 8.65 (s, 1H), 8.86 (br s, 1H), 9.01-9.18 (m, 1H)

LCMS (ESI+): m/z 251.0 (M+H)$^+$, RT: 1.64 min

LCMS Method: LC/MS (The gradient was 5% B in 0.40 min and 5-95% B at 0.40-3.00 min, hold on 95% B for 1.00 min, and then 95-5% B in 0.0 min, the flow rate was 1.0 ml/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

General Procedure for Preparation of Cpd 1B

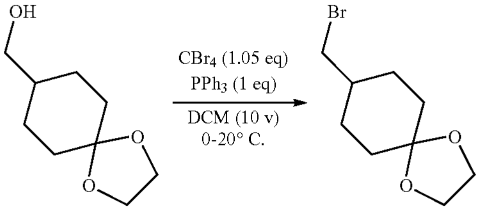

1A 1B

To a solution of Cpd 1A (3 g, 17.42 mmol) in dichloromethane (30 mL) was added carbon tetrabromide (6.07 g, 18.29 mmol) and triphenyl phosphine (4.57 g, 17.42 mmol) at 0° C. The reaction was stirred at 20° C. for 12 h. TLC showed starting material consumed and new spot was detected. The residue was diluted with $H_2O$ (50 mL) and extracted with dichloromethane (50 mL×3). The combined organic layers were washed with $H_2O$ (50 mL×2), dried over $MgSO_4$, filtered and concentrated under reduced pressure to give a residue. The reaction was purified by column chromatography ($SiO_2$, petroleum ether:ethyl acetate=92:8) to give Cpd 1B (2 g, yield 48%) as yellow oil.

Confirmation $^1$H NMR (ET45209-84-P1N1, 400 MHz, DMSO-d6) δ 1.22-1.33 (m, 2H) 1.46 (td, J=13.05, 4.10 Hz, 2H) 1.60-1.69 (m, 3H) 1.71-1.79 (m, 2H) 3.45 (d, J=6.11 Hz, 2H) 3.84 (s, 4H)

General Procedure for Preparation of Cpd 1

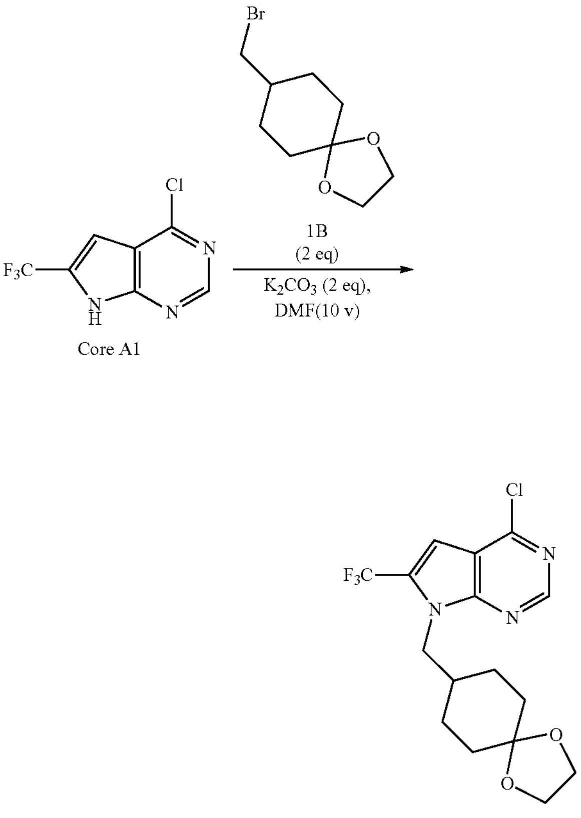

1

To a solution of Core A1 (0.2 g, 902.66 μmol) and Cpd 1B (424.46 mg, 1.81 mmol) in dimethylformamide (2 mL) was added $K_2CO_3$ (249.51 mg, 1.81 mmol) at 20° C. The reaction was stirred at 70° C. for 12 h. LCMS showed starting material consumed and desired product. The mixture was concentrated to give a residue. The reaction was purified by column chromatography ($SiO_2$, petroleum ether: ethyl acetate=80:20) to give Cpd 1 (0.228 g, yield 67%) as yellow oil.

Confirmation

LCMS (ESI+): m/z=376.1 (M+H)$^+$, RT: 0.687 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% $CF_3CO_2H$ in water, mobile phase B was 0.02% $CF_3CO_2H$ in $CH_3CN$. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

General Procedure for Preparation of Cpd 2

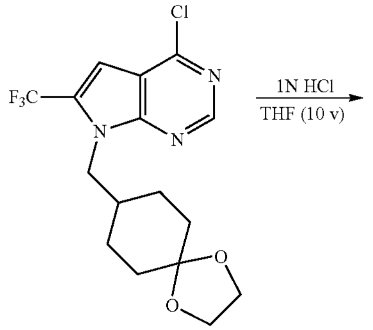

1

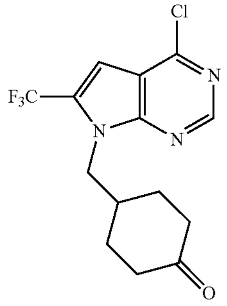

2

To a solution of Cpd 1 (100 mg, 26.61 μmol) in tetrahydrofuran (1 mL) was added HCl (1 N, 1 mL) at 20° C. The reaction was stirred at 20° C. for 12 h. LCMS showed starting material consumed and desired product was detected. The mixture was concentrated to give Cpd 2 (60 mg, yield 68%) was obtained as yellow oil which was used to next step without any purification.

Confirmation

LCMS (ESI+): m/z 332.0 $(M+H)^+$, RT: 0.771 min

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.04% $CF_3CO_2H$ in water, mobile phase B was 0.02% $CF_3CO_2H$ in $CH_3CN$. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

General Procedure for Preparation of Core A1-012

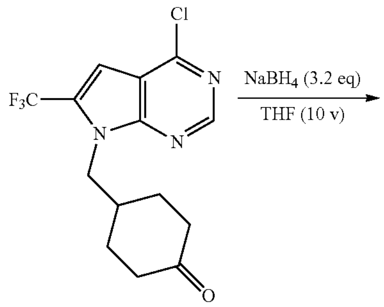

2

-continued

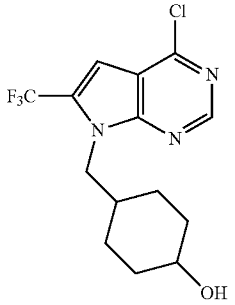

Core A1-012

To a solution of Cpd 2 (20 mg, 60.29 μmol) in tetrahydrofuran (0.2 mL) was added $NaBH_4$ (7.30 mg, 192.93 μmol) at 20° C. The reaction was stirred at 20° C. for 12 h. LCMS showed starting material consumed and desired product was detected. The mixture was concentrated to give a residue which was purified by prep-HPLC (column: Waters Xbridge BEH C18 100*30 mm*10 um; mobile phase: [water ($NH_3H_2O$+$NH_4HCO_3$)-acetonitrile]; B %: 30%-55%, 8 min) to give Core A1-012 (15 mg, yield 75%) as white solid.

$^1$H NMR (ET45209-96-p1n1, 400 MHz, ACETONITRILE-d3) δ 1.04-1.20 (m, 4H) 1.45-1.55 (m, 2H) 1.84 (br d, J=10.51 Hz, 2H) 1.96-2.05 (m, 1H) 2.66 (br s, 1H) 3.37-3.49 (m, 1H) 4.23 (d, 1=7.58 Hz, 2H) 7.19 (s, 1H) 8.72 (s, 1H).

$^{19}$F NMR (ET45209-96-p1n1, 400 MHz, ACETONITRILE-d3) δ −60.027.

LCMS (ESI+): m/z=334.1 $(M+H)^+$, RT: 2.910 min

5_95CD_6 min-220-254-ELSD: LC/MS (The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was $H_2O$+10 mM $NH_4HCO_3$, mobile phase B was Acetonitrile. The column used for chromatography was a Xbridge-C18 2.1×50 mm column (Sum particles). Detection methods are diode array (DAD) and evaporative light scattering (ELSD) detection as well as positive electrospray ionization. MS range was 100-1000.

General Procedure for Preparation of Compound 2

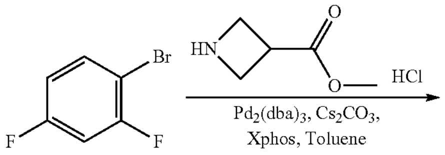

1

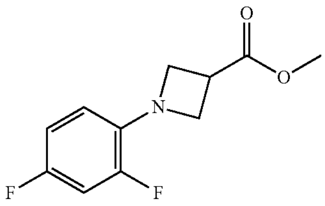

2

To a solution of Compound 1 (1.07 g, 5.54 mmol, 1.2 eq) and methyl azetidine-3-carboxylate; hydrochloride (700 mg, 4.62 mmol, 1 eq) in toluene (20 mL) were added $Pd_2(dba)_3$ (84.57 mg, 92.35 umol, 0.02 eq), $Cs_2CO_3$ (6.02 g, 18.47 mmol, 4 eq) and XPhos (132.08 mg, 277.06 umol, 0.06 eq) under N2 atmosphere. The mixture was stirred at 100° C. for 12 hrs. TLC (petroleum ether/ethyl acetate=5/1) showed the starting material was consumed and a new spot generated. The mixture was concentrated under reduced pressure. The residue was purified by column chromatography on silica gel (eluting with petroleum ether/ethyl acetate=5/1)) to give Compound 2 (570 mg, 2.26 mmol, 48.90% yield) as a yellow oil.

$^1$H NMR (400 MHz, METHANOL-d) δ 3.58 (tt, J=8.38, 6.25 Hz, 1H), 3.74 (s, 3H), 3.95-4.04 (m, 2H), 4.11 (td, J=7.91, 2.06 Hz, 2H), 6.57 (td, J=9.38, 5.50 Hz, 1H), 6.76-6.91 (m, 2H).

$^{19}$F NMR (400 MHz, METHANOL-d4) δ −125.171, −129.528.

General Procedure for Preparation of Compound 3

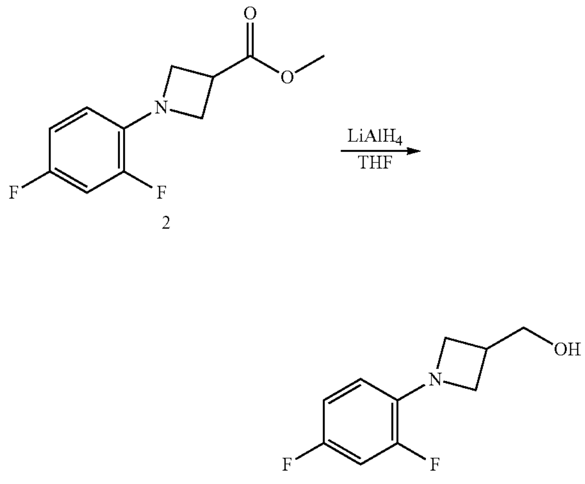

2

3

To a solution of Compound 2 (470 mg, 2.07 mmol, 1 eq) in tetrahydrofuran (10 mL) was added $LiAlH_4$ (328.18 mg, 8.65 mmol, 4.18 eq) under N2 atmosphere at 0° C. The mixture was stirred at 0° C. for 30 min and then warmed to 20° C. for 1 hr. TLC (petroleum ether/ethyl acetate=2/1) showed the starting material was consumed and a new spot generated. The mixture was quenched with water (1 mL) and aqueous NaOH (15%, 1 mL). The mixture was filtered and the filtrate was extracted with ethyl acetate (3×2 mL). The organic layer was washed with brine (2 mL) and dried over $Na_2SO_4$, filtered and concentrated under reduced pressure. The residue was purified by prep-TLC (petroleum ether/ethyl acetate=2/1) to give Compound 3 (310 mg, 1.40 mmol, 67.71% yield) as a white solid.

$^1$H NMR (400 MHz, METHANOL-d4) δ 2.79-2.92 (m, 1H), 3.63-3.71 (m, 2H), 3.77 (d, J=6.63 Hz, 2H), 3.97 (td, J=7.60, 1.69 Hz, 2H), 6.56 (td, J=9.35, 5.69 Hz, 1H), 6.75-6.88 (m, 2H).

$^{19}$F NMR (400 MHz, METHANOL-d4) δ −125.976, −129.469.

General Procedure for Preparation of Compound 4

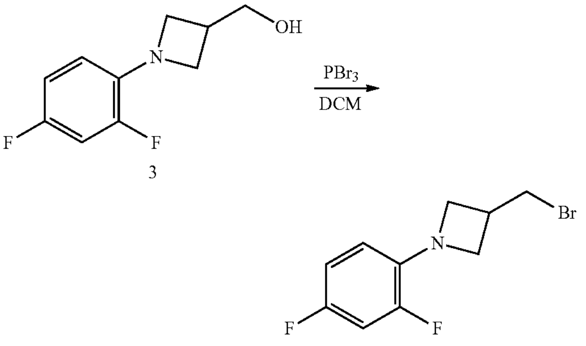

3

4

To a solution of Compound 3 (410 mg, 2.06 mmol, 1 eq) in dichloromethane (1 mL) was added PBr. (668.58 mg, 2.47 mmol, 1.2 eq) at 0° C. The mixture was stirred at 20° C. for 1 hr. TLC (petroleum ether/ethyl acetate=2/1) showed the starting material was consumed and a new spot generated. The reaction mixture was quenched by the addition of saturated aqueous $Na_2CO_3$ (2 mL) and extracted with ethyl acetate (2×4 mL). The organic layer was washed with brine (3 mL), dried over $Na_2SO_4$, filtered and the filtrate was concentrated to give the crude product, which was purified by prep-TLC (petroleum ether/ethyl acetate=2/1) to give Compound 4 (140 mg, 0.48 mmol, 23.36% yield) as a white solid.

1H NMR (400 MHz, METHANOL-d4) δ 2.29-2.39 (m, 1H), 3.28 (d, J=6.75 Hz, 2H), 3.60-3.66 (m, 2H), 3.66-3.74 (m, 2H), 6.70-6.91 (m, 3H).

$^{19}$F NMR (400 MHz, METHANOL-d4) δ −128.493, −133.095.

General Procedure for Preparation of Core A1-010

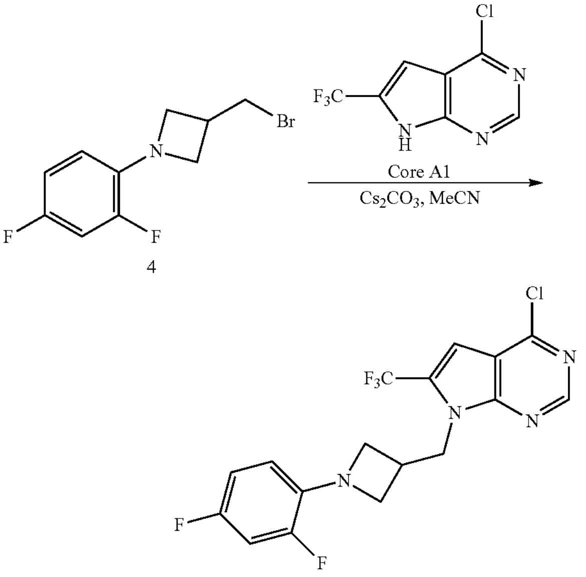

4

Core A1-010

To a solution of Compound 4 (70.97 mg, 270.80 umol, 1.2 eq) and Core A1 (50 mg, 225.67 umol, 1 eq) in acetonitrile (2 mL) was added $Cs_2CO_3$ (294.10 mg, 902.66 umol, 4 eq) and the mixtures was stirred at 80° C. for 7 hrs. TLC (petroleum ether/ethyl acetate=2/1) showed most of the starting material was consumed and a new main spot generated. The mixture was concentrated under reduced pressure. The residue was purified by prep-TLC (petroleum ether/ethyl acetate=2/1) to give Core A1-010 (13 mg, 29.05 umol, 12.87% yield) as a white solid.

LCMS method: LCMS (ESI+): m/z 403.0 $(M+H)^+$, RT: 3.184 min. LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.

$^1$H NMR (400 MHz, METHANOL-d4) δ 1.21-1.39 (m, 1H), 3.84 (s, 2H), 4.39 (s, 1H), 5.09-5.15 (m, 3H), 6.56-6.64 (m, 1H), 6.65-6.74 (m, 1H), 6.81 (ddd, J=11.69, 8.76, 2.81 Hz, 1H), 7.28 (d, J=0.88 Hz, 1H), 8.73 (s, 1H).

$^{19}$F NMR (400 MHz, METHANOL-d4) δ −128.616, −133.554.

General Procedure for Preparation of Compound 2

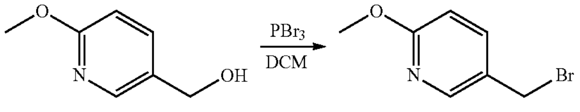

1
2

To a solution of Cpd 1 (0.2 g, 1.44 mmol, 1 eq) in dichloromethane (2 mL) was added $PBr_3$ (466.86 mg, 1.72 mmol, 1.2 eq) at 0° C. and stirred for 2 hrs at 25° C. under N2. TLC (petroleum ether/ethyl acetate=4/1) showed the starting material was consumed and a new main spot was generated. The reaction mixture was adjusted to pH=8 with saturated aqueous $NaHCO_3$. The reaction mixture was extracted with dichloromethane (3×10 mL). The organic layer was dried over $Na_2SO_4$, filtered and the filtrate was concentrated to give Cpd 2 (0.25 g, 989.86 umol, 68.87% yield) as a white oil, which was used in next step without further purification.

$^1$H NMR (400 MHz, DMSO-d6) δ 3.85 (s, 3H) 4.72 (s, 2H) 6.83 (d, J=8.63 Hz, 1H) 7.78 (dd, J=8.63, 2.50 Hz, 1H) 8.25 (d, 0.1=2.25 Hz, 1H)

General Procedure for Preparation of Core-A1-030_3

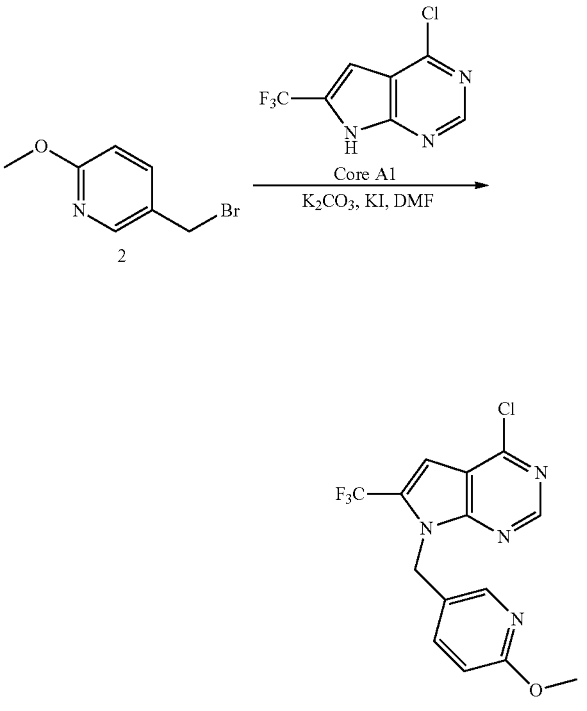

2
Core A1-030_3

To a solution of Core A1 (50 mg, 225.67 umol, 1 eq) in N, N-dimethylformamide (1 mL) were added Cpd 2 (68.39 mg, 338.50 umol, 1.5 eq), $K_2CO_3$ (62.38 mg, 451.33 umol, 2 eq) and KI (3.75 mg, 22.57 umol, 0.1 eq) at 25° C. The mixture was stirred for 12 hrs at 50° C. under N2. TLC (petroleum ether/ethyl acetate=4/1) showed the starting material was consumed and a new main spot was generated. The mixture was poured into ice water (5 mL) and extracted with ethyl acetate (2×5 mL). The organic layer was washed with brine (5 mL), dried over $Na_2SO_4$, filtered and the filtrate was concentrated to give the crude product, which was purified by prep-TLC (petroleum ether/ethyl acetate=4/1) to give Core A1-030_3 (16.8 mg, 49.02 umol, 21.72% yield) as a white solid.

LCMS method: LCMS (ESI+): m/z=343.0 $(M+H)^+$, RT: 2.864 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

$^1$H NMR (400 MHz, CHLOROFORM-A) δ 3.91 (s, 3H) 5.54 (s, 2H) 6.68 (d, J=8.53 Hz, 1H) 7.10 (s, 1H) 7.55 (dd, J=8.60, 2.45 Hz, 1H) 8.17 (d, J=2.13 Hz, 1H) 8.81 (s, 1H)

$^{19}$F NMR (400 MHz, CHLOROFORM-a) δ −59.483.

General Procedure for Preparation of Compound Core A1-030

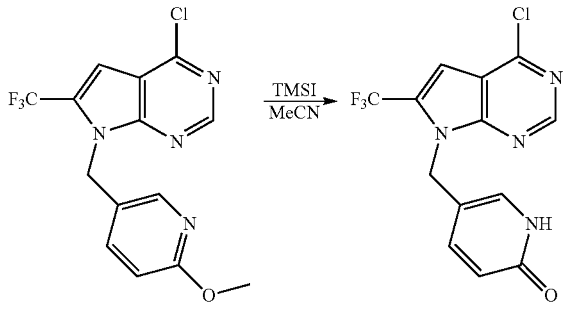

Core A1-030_3 Core A1-030

To a solution of Core A1-030_3 (60 mg, 175.08 umol, 1 eq) in acetonitrile (2 mL) was added TMSI (70.06 mg, 350.16 umol, 47.66 uL, 2 eq) at 25° C. The mixture was stirred at 50° C. for 12 hrs. LCMS showed the starting material was consumed, 68.3% product with desired MS was detected. The mixture was poured in water (5 mL) and extracted with (3×5 mL). The organic layer was dried over $Na_2SO_4$, filtered and the filtrate was concentrated to give the crude product, which was purified by prep-HPLC to give Core A1-030 (15.7 mg, 47.77 umol, 27.28% yield) as a white solid.

The method of prep-HPLC purification: Column: Phenomenex Luna 80*30 mm*3 um; mobile phase: [water (TFA)-ACN]; B %: 15%-55%, 8 min LCMS method: LCMS (ESI+): m/z=329.0 $(M+H)^+$, RT: 2.154 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

$^1H$ NMR (400 MHz, METHANOL-d4) δ 5.48 (s, 2H) 6.49 (d, J=9.51 Hz, 1H) 7.32 (s, 1H) 7.48 (s, 1H) 7.59 (dd, J=9.51, 2.63 Hz, 1H) 8.82 (s, 1H)

$^{19}F$ NMR (400 MHz, METHANOL-d4) δ −60.923, −77.694.

General Procedure for Preparation of Compound 2

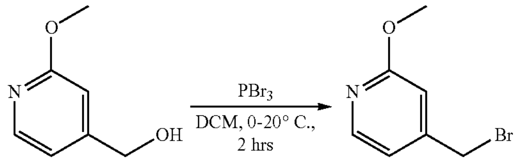

1 2

To a stirred solution of Compound 1 (0.5 g, 3.59 mmol, 1 eq) in DCM (5 mL) was added $PBr_3$ (1.17 g, 4.31 mmol, 1.2 eq) at 0° C. The reaction was stirred at 20° C. for 2 hrs. TLC (petroleum ether/ethyl acetate=3/1) showed the starting material was consumed and a new spot was generated. The reaction was quenched with $NaHCO_3$ solution (40 mL) and extracted with DCM (3×20 mL). The combined organic layers were dried over $Na_2SO_4$, filtered and concentrated under reduced pressure to give Compound 2 (0.8 g, 3.37 mmol, 93.66% yield, 85% purity) as a brown oil. The product was used to next step directly without further purification.

$^1H$ NMR (400 MHz, CHLOROFORM-d) δ 3.96 (s, 3H), 4.35 (s, 2H), 6.76 (s, 1H), 6.90 (dd, J=5.32, 1.31 Hz, 1H), 8.15 (d, J=5.25 Hz, 1H)

General Procedure for Preparation of Core A1-031_3

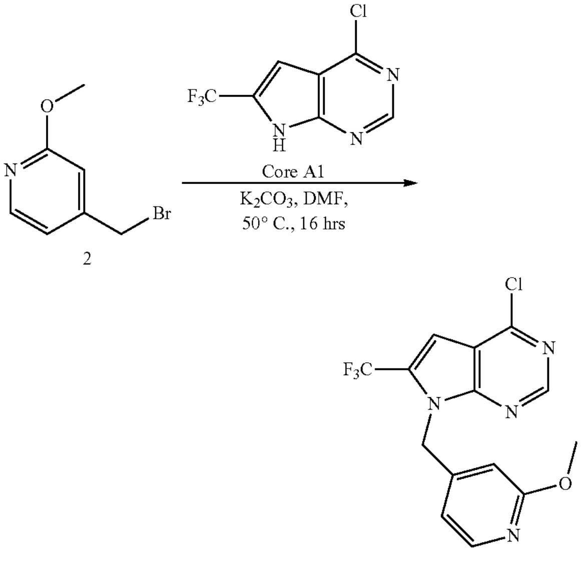

2

Core A1-031_3

To a solution of Core A1 (200 mg, 902.66 umol, 1 eq) in DMF (2 mL) were added Compound 2 (237.10 mg, 1.17 mmol, 1.3 eq) and $K_2CO_3$ (249.51 mg, 1.81 mmol, 2 eq). The mixture was stirred at 50° C. for 16 hrs. LCMS showed all starting material consumed and product with desired MS was detected. The mixture was diluted with water (10 mL) and extracted with ethyl acetate (3×10 mL). The combined organic layer was dried over $Na_2SO_4$, filtered and concentrated under reduced pressure to give a residue, which was purified by prep-HPLC (column. Phenomenex luna C18 80*40 mm*3 um; mobile phase: [water (TFA)-ACN]; B %: 47%-63%, 7 min) to give Core A1-031_3 (26 mg, 72.07 umol, 15.97% yield, 95% purity) as a brown solid.

LCMS method: LCMS (ESI+): m/z=343.0 $(M+H)^+$, RT: 2.740 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.

$^1H$ NMR (400 MHz, CHLOROFORM-d) δ 3.95 (s, 3H), 5.62 (s, 2H), 6.45 (s, 1H), 6.73 (d, J=5.50 Hz, 1H), 7.20 (s, 1H), 8.21 (d, J=5.50 Hz, 1H), 8.81 (s, 1H)

$^{19}F$ NMR (400 MHz, CHLOROFORM-d) δ −59.947, −75.764.

General Procedure for Preparation of Core A1-031

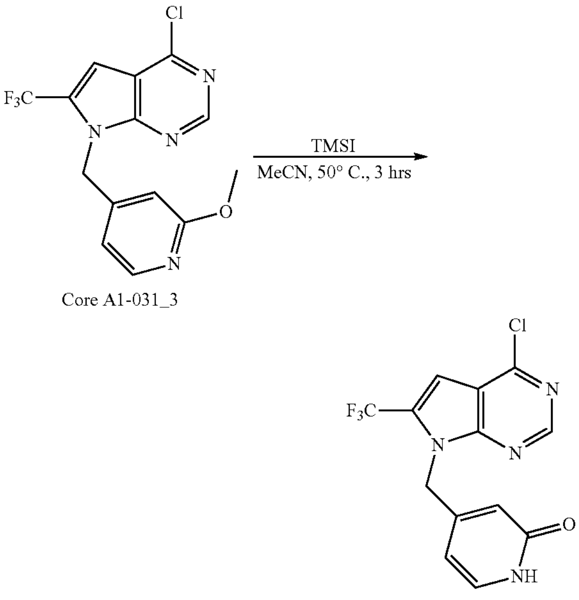

Core A1-031_3

Core A1-031

To a solution of Core A1-031_3 (90 mg, 262.62 umol, 1 eq) in MeCN (4 mL) was added TMSI (105.09 mg, 525.24 umol, 71.49 uL, 2 eq). The mixture was stirred at 50° C. for 3 hrs. LCMS showed the starting material was consumed and product with desired mass was detected. The solution was concentrated under reduced pressure to give a residue. The residue was purified by prep-HPLC (column: Phenomenex Luna 80*30 mm*3 um; mobile phase: [water (TFA)-ACN]; B %: 30%-60%, 8 min) to give Core A1-031 (43 mg, 97.13 umol, 36.99% yield, 100% purity, TFA salt) as white solid.

LCMS method: LCMS (ESI+): m/z=328.9 $(M+H)^+$, RT: 2.085 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

$^1H$ NMR (400 MHz, DMSO-d6) δ 5.49 (s, 2H), 5.69 (s, 1H), 5.96 (dd, J=6.82, 1.56 Hz, 1H), 7.34 (d, J=6.88 Hz, 1H), 7.59 (s, 1H), 8.90 (s, 1H)

$^{19}F$ NMR (400 MHz, DMSO-d6) δ −59.078, −74.793.

General Procedure for Preparation of Compound Core B

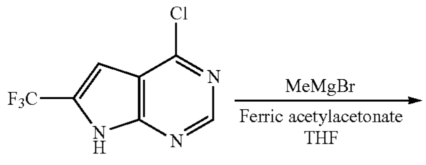

Core A1

Core B

To a solution of Core A1 (0.2 g, 902.66 umol, 1 eq) and Ferric acetylacetone (31.88 mg, 90.27 umol, 0.1 eq) in tetrahydrofuran (5 mL) was cooled to 0° C. Methylmagnesium bromide (3 M ether solution, 361.06 uL, 1.2 eq) was added dropwise and the mixture was stirred at 0° C. for 2 hrs. TLC (petroleum ether/ethyl acetate=2/1) showed the starting material was consumed and a new main spot was generated. The reaction mixture was quenched with aqueous $NH_4Cl$ (10 mL), then extracted with ethyl acetate (3×10 mL). The organic layer was dried over $Na_2SO_4$, filtered and concentrated under reduced pressure to give the crude product, which was purified by prep-TLC (petroleum ether/ethyl acetate=2/1) to give Core B (0.1 g, 447.43 umol, 49.57% yield) as yellow solid.

$^1H$ NMR (400 MHz, CHLOROFORM-d) δ ppm 2.85 (s, 3H) 7.04 (d, 0.1=1.00 Hz, 1H) 8.93 (s, 1H)

$^{19}F$ NMR (400 MHz, CHLOROFORM-d) δ −61.419.

General Procedure for Preparation of Compound 36-1

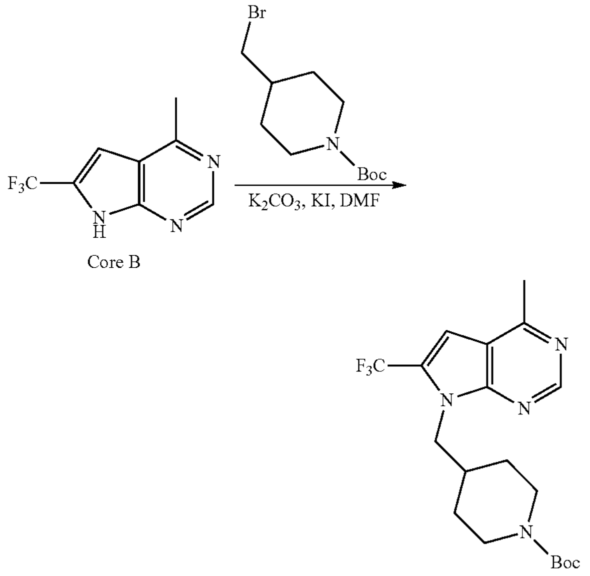

Core B 36-1

To a solution of Core B (0.1 g, 497.15 umol, 1 eq) in N, N-dimethylformamide (3 mL) was added tert-butyl 4-(bromomethyl)piperidine-1-carboxylate (207.45 mg, 745.72 umol, 1.5 eq), $K_2CO_3$ (137.42 mg, 994.29 umol, 2 eq) and KI (16.51 mg, 99.43 umol, 0.2 eq) at 25° C. The mixture was stirred at 40° C. for 3 hrs under N2. TLC (petroleum ether/ethyl acetate=3/1) showed the starting material was consumed and a new main spot was generated. The mixture was cooled to 25° C. and poured into water (10 mL), then extracted with ethyl acetate (3×10 mL). The organic layer was dried over $Na_2SO_4$, filtered and the filtrate was concentrated to give the crude product, which was purified by prep-TLC (petroleum ether/ethyl acetate=3/1) to give Cpd 36-1 (0.13 g, 309.97 umol, 62.35% yield) as a white solid.

$^1$H NMR (400 MHz, METHANOL-d) δ 1.27 (qd, J=12.51, 4.00 Hz, 2H) 1.45 (s, 11H) 2.28 (ddd, J=11.29, 7.60, 3.50 Hz, 1H) 2.58-2.74 (m, 2H) 2.78 (s, 3H) 4.06 (br d, J=13.38 Hz, 2H) 4.31 (d, J=7.50 Hz, 2H) 7.34 (s, 1H) 8.80 (s, 1H)

$^{19}$F NMR (400 MHz, METHANOL-d4) δ −60.624.

General Procedure for Preparation of Core A1-036

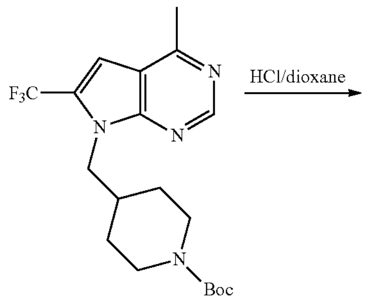

36-1

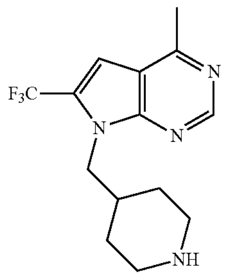

Core A1-036

To a solution of Cpd 36-1 (0.11 g, 276.09 umol, 1 eq) in dioxane (2 mL) was added HCl/dioxane (4 M, 22 mL, 318.74 eq) and stirred at 25° C. for 2 hrs. LCMS showed the starting material consumed, main product with desired MS was detected. The reaction mixture was concentrated to give the crude product, which was purified by prep-HPLC to give Core A1-036 (20.5 mg, 68.72 umol, 24.89% yield) as a white solid.

The method of prep-HPLC purification: Column: Phenomenex Luna 80*30 mm*3 um; mobile phase: [water (TFA)-ACN]; B %: 1%-25%, 8 min.

LCMS method: LCMS (ESI+): m/z=329.0 (M+H)$^+$, RT: 1.522 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% trifluoroacetic acid in water, mobile phase B was 0.02% trifluoroacetic acid in acetonitrile. The column used for chromatography was a Luna C18 50*2.0 mm column (5 um particles). Detection methods are diode array (DAD) and evaporative light scattering (ELSD) detection as well as positive electrospray ionization. MS range was 100-1000.

$^1$H NMR (400 MHz, METHANOL-d4) δ 1.55-1.67 (m, 2H) 1.79 (br d, J=14.13 Hz, 2H) 2.44 (td, 1=7.50, 3.75 Hz, 1H) 2.84 (s, 3H) 2.90-2.99 (m, 2H) 3.40 (br d, 0.1=12.88 Hz, 2H) 4.41 (d, 1=7.50 Hz, 2H) 7.49 (s, 1H) 8.88 (s, 1H)

$^{19}$F NMR (400 MHz, METHANOL-d4) δ −60.784, −77.268.

General Procedure for Preparation of Compound 042-1

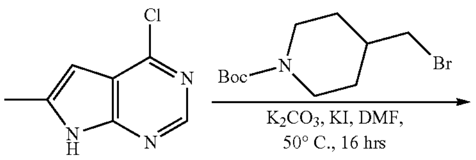

1

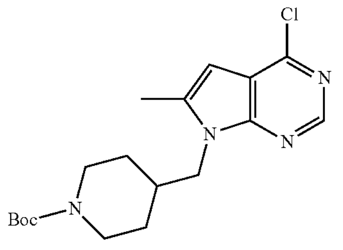

042-1

To a solution of Compound 1 (180 mg, 1.07 mmol, 1 eq) in DMF (4 mL) were added tert-butyl 4-(bromomethyl) piperidine-1-carboxylate (448.16 mg, 1.61 mmol, 1.5 eq), KI (35.66 mg, 214.80 umol, 0.2 eq) and $K_2CO_3$ (296.87 mg, 2.15 mmol, 2 eq). The mixture was stirred at 50° C. for 16 hrs. TLC (petroleum ether/ethyl acetate=2/1) showed most of starting material was consumed and a new spot was detected. The mixture was diluted with water (20 mL) and extracted with ethyl acetate (3×10 mL). The combined organic layer was dried over $Na_2SO_4$, filtered and concentrated under reduced pressure to give a residue. The residue was purified by prep-TLC (eluted with petroleum ether/ethyl acetate=2/1) to give Compound 042-1 (350 mg, 863.32 umol, 80.38% yield, 90% purity) as a colorless oil.

$^1$H NMR (400 MHz, CHLOROFORM-d) δ 1.24-1.30 (m, 2H), 1.46 (s, 9H), 1.51 (br d, J=13.13 Hz, 2H), 2.08 (dt, J=7.75, 3.88 Hz, 1H), 2.49 (s, 3H), 2.55-2.69 (m, 2H), 4.04-4.17 (m, 4H), 6.36 (s, 1H), 8.57 (s, 1H)

General Procedure for Preparation of Core A1-042

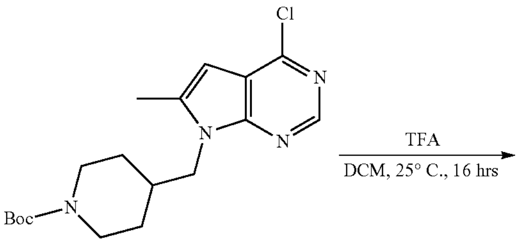

042-1

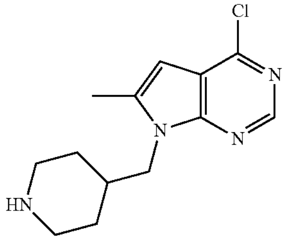

Core A1-042

To a solution of Compound 042-1 (200 mg, 548.14 umol, 1 eq) in DCM (4 mL) was added TFA (1.54 g, 13.51 mmol, 1 mL, 24.64 eq). The solution was stirred at 25° C. for 16 hrs. LCMS showed the starting material was consumed and product with desired mass was detected. The solution was concentrated under reduced pressure to give a residue. The residue was purified by prep-HPLC (column: Phenomenex Luna C18 150*30 mm*5 um; mobile phase: [water (TFA)-ACN]; B %: 1%-35%, 8 min) to give Core A1-042 (131 mg, 494.80 umol, 90.27% yield, 100% purity) as a white solid.

LCMS method: LCMS (ESI+): m/z=265.0 $(M+H)^+$, RT: 1.643 min. 5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

$^1H$ NMR (400 MHz, METHANOL-d4) δ 1.49-1.67 (m, 2H), 1.77 (br d, J=13.76 Hz, 2H), 2.29 (dtt, J=15.28, 7.63, 3.92 Hz, 1H), 2.56 (s, 3H), 2.84-3.04 (m, 2H), 3.39 (br d, J=13.01 Hz, 2H), 4.26 (d, J=7.50 Hz, 2H), 6.46 (s, 1H), 8.49 (s, 1H)

$^{19}F$ NMR (400 MHz, METHANOL-d4) δ −76.990.

Example 2—Inhibition of Cell Proliferation

Experimental procedure for measuring IC50 values of the tested compounds in MV-4-11 cells are described below, which was adapted from *Chem Biol Drug Des.* 2019 October; 94(4): 1813-1823.

Cell viability was assessed using the CellTiter-Glo 2.0 assay from Promega, which yields a signal proportional to the amount of ATP present in a cell population. Compounds were first dispensed into empty 96-well flat-bottom tissue culture-treated plates (Corning) using an Echo550. MV4-1 cells were diluted to a density of 0.1 million cells per ml, pipetted onto the compounds at a density of 1,000 cells per well for U937 and 3,000 cells per well for MV4-11, mixed, and incubated for 3 days at 37° C. with 5% C02. After incubating, 5 μl of cells from each well were added to 5 μl of CellTiter-Glo 2.0 reagent in a384-well white ProxiPlate (PerkinElmer), incubated for 20 minutes at ambient temperature, and luminescence was analyzed on an EnSpire plate reader. Graphing and regression analysis was performed in Graphpad Prism.

TABLE 1

Inhibitory activity of compounds

| Molecule Name | Structure | IC50 (uM) [Cell Type: MV-4-11] | Synonym |
|---|---|---|---|
| NUCC-0226439 | 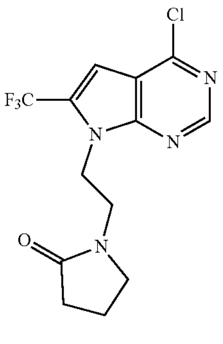 [SMILES: O=C1CCCN1CCn1c(C(F)(F)F)cc2c(Cl)ncnc21] | 0.11 | |

TABLE 1-continued
Inhibitory activity of compounds
| Molecule Name | Structure | IC50 (uM) [Cell Type: MV-4-11] | Synonym |
|---|---|---|---|
| NUCC-0226440 | 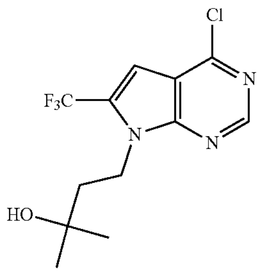 [SMILES: CC(C)(O)CCn1c(C(F)(F)F)cc2c(Cl)ncnc21] | 0.23 | |
| NUCC-0226665 | 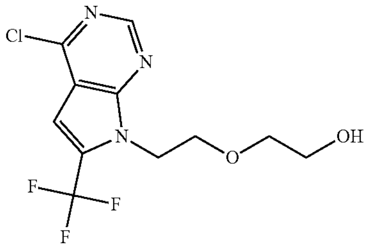 [SMILES: OCCOCCn1c(C(F)(F)F)cc2c(Cl)ncnc21] | 1.23 | Core A1-001 |
| NUCC-0226666 | 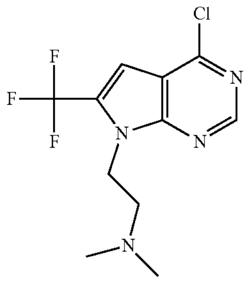 [SMILES: CN(C)CCn1c(C(F)(F)F)cc2c(Cl)ncnc21] | 2.09 | Core A1-002 |
| NUCC-0226667 | 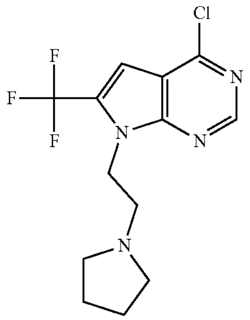 [SMILES: FC(F)(F)c1cc2c(Cl)ncnc2n1CCN1CCCC1] | 1.43 | Core A1-003 |
| NUCC-0226668 | 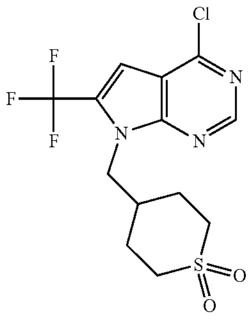 [SMILES: O=S1(=O)CCC(Cn2c(C(F)(F)F)cc3c(Cl)ncnc32)CC1] | 2.88 | Core A1-004 |

TABLE 1-continued
Inhibitory activity of compounds
| Molecule Name | Structure | IC50 (uM) [Cell Type: MV-4-11] | Synonym |
|---|---|---|---|
| NUCC-0226669 | 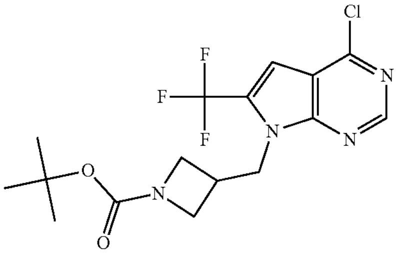 [SMILES: CC(C)(C)OC(=O)N1CC(Cn2c(C(F)(F)F)cc3c(Cl)ncnc32)C1] | 1.02 | Core A1-006 |
| NUCC-0226670 | 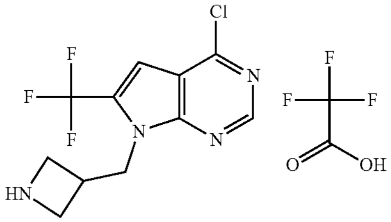 | 1.12 | Core A1-007 |
| NUCC-0226671 | 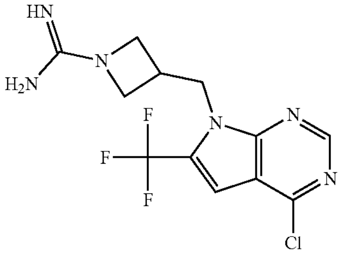 [SMILES: N=C(N)N1CC(Cn2c(C(F)(F)F)cc3c(Cl)ncnc32)C1] | >20.0 | Core A1-008 |
| NUCC-0226672 | 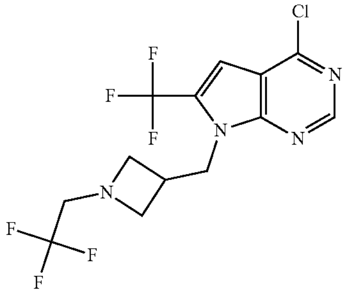 [SMILES: FC(F)(F)CN1CC(Cn2c(C(F)(F)F)cc3c(Cl)ncnc32)C1] | 0.871 | Core A1-009 |
| NUCC-0226673 | 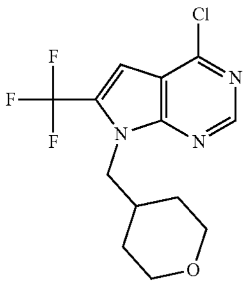 [SMILES: FC(F)(F)c1cc2c(Cl)ncnc2n1CC1CCOCC1] | 2.68 | Core A1-011 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226674 | 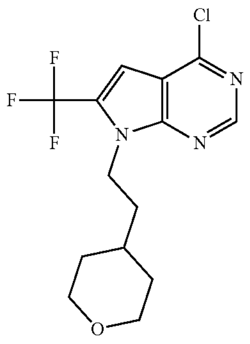 [SMILES: FC(F)(F)c1cc2c(Cl)ncnc2n1CCC1CCOCC1] | 1.29 | Core A1-013 |
| NUCC-0226675 | 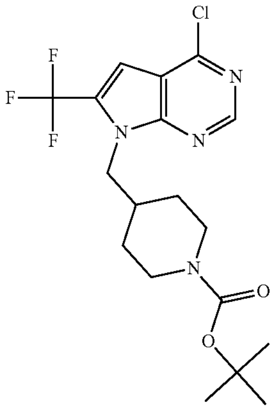 [SMILES: CC(C)(C)OC(=O)N1CCC(Cn2c(C(F)(F)F)cc3c(Cl)ncnc32)CC1] | 2.51 | Core A1-014 |
| NUCC-0226676 | 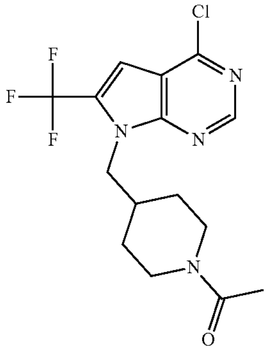 [SMILES: CC(=O)N1CCC(Cn2c(C(F)(F)F)cc3c(Cl)ncnc32)CC1] | >20.0 | Core A1-017 |
| NUCC-0226677 | 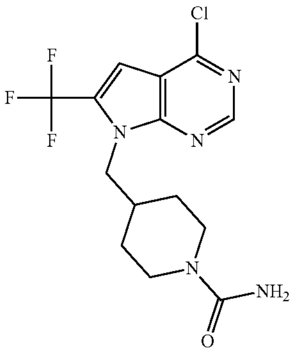 [SMILES: NC(=O)N1CCC(Cn2c(C(F)(F)F)cc3c(Cl)ncnc32)CC1] | 1.6 | Core A1-018 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226678 | 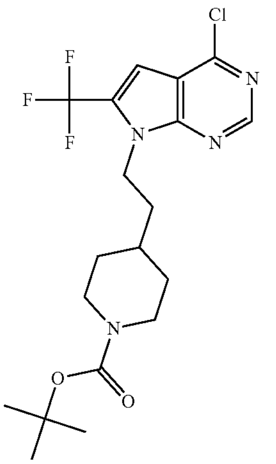 [SMILES: CC(C)(C)OC(=O)N1CCC(CCn2c(C(F)(F)F)cc3c(Cl)ncnc32)CC1] | 1.3 | Core A1-020 |
| NUCC 0226679 | 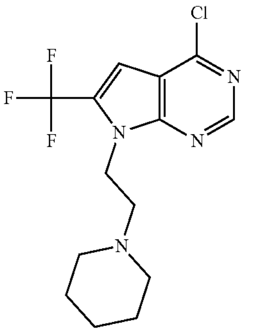 [SMILES: FC(F)(F)c1cc2c(Cl)ncnc2n1CCN1CCCCC1] | 0.675 | Core A1-022 |
| NUCC-0226680 | 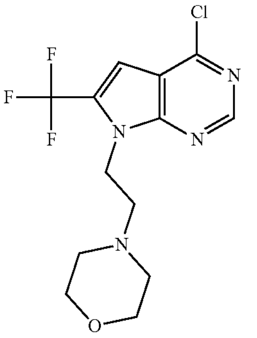 [SMILES: FC(F)(F)c1cc2c(Cl)ncnc2n1CCN1CCOCC1] | 0.679 | Core A1-024 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226681 | 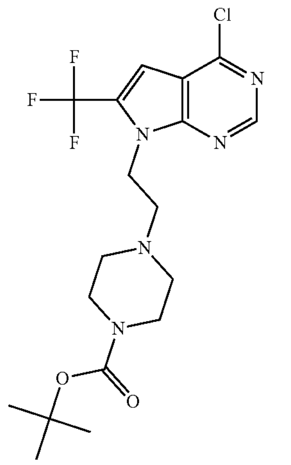 [SMILES: CC(C)(C)OC(=O)N1CCN(CCn2c(C(F)(F)F)cc3c(Cl)ncnc32)CC1] | 0.949 | Core A1-025 |
| NUCC-0226682 | 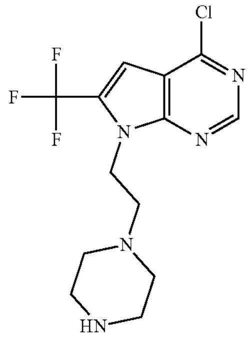 [SMILES: FC(F)(F)c1cc2c(Cl)ncnc2n1CCN1CCNCC1] | 2.24 | Core A1-026 |
| NUCC-0226683 | 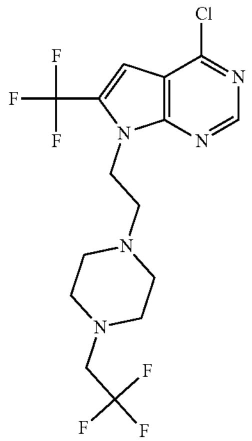 [SMILES: FC(F)(F)CN1CCN(CCn2c(C(F)(F)F)cc3c(Cl)ncnc32)CC1] | 1.83 | Core A1-027 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226684 | 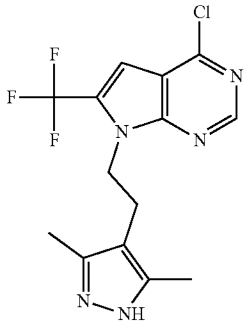 [SMILES: Cc1n[nH]c(C)c1CCn1c(C(F)(F)F)cc2c(Cl)ncnc21] | 0.94 | Core A1-028 |
| NUCC-0226685 | 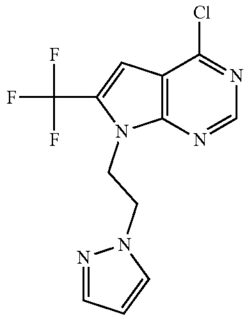 [SMILES: FC(F)(F)c1cc2c(Cl)ncnc2n1CCn1cccn1] | 3.98 | Core A1-029 |
| NUCC-0226686 | 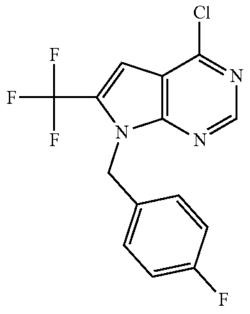 [SMILES: Fc1ccc(Cn2c(C(F)(F)F)cc3c(Cl)ncnc32)cc1] | 1.13 | Core A1 032 |
| NUCC-0226687 | 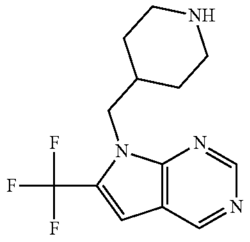 [SMILES: FC(F)(F)c1cc2cncnc2n1CC1CCNCC1] | >20.0 | Core A1-037 |
| NUCC-0226688 | 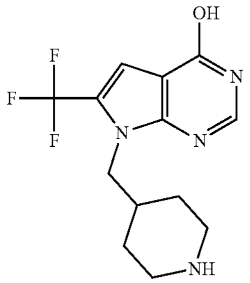 [SMILES: Oc1ncnc2c1cc(C(F)(F)F)n2CC1CCNCC1] | >20.0 | Core A1-038 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226689 | 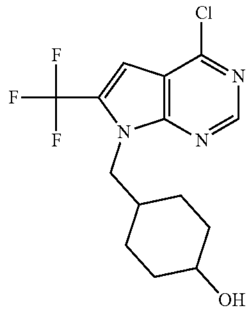 [SMILES: OC1CCC(Cn2c(C(F)(F)F)cc3c(Cl)ncnc32)CC1] | 0.689 | Core A1-012 |
| NUCC-0226690 | 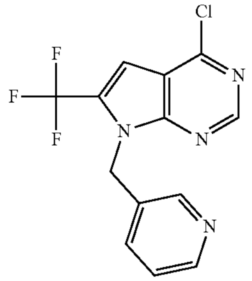 [SMILES: FC(F)(F)c1cc2c(Cl)ncnc2n1Cc1cccnc1] | 0.562 | Core A1-034 |
| NUCC-0226691 | 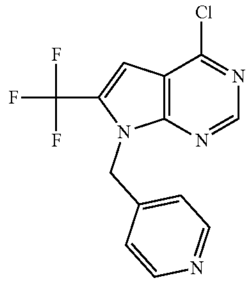 [SMILES: FC(F)(F)c1cc2c(Cl)ncnc2n1Cc1ccncc1] | 1.32 | Core A1-035 |
| NUCC-0226692 | 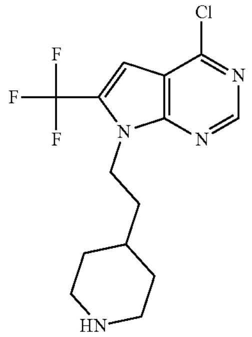 [SMILES: FC(F)(F)c1cc2c(Cl)ncnc2n1CCC1CCNCC1] | 0.773 | Core A1-021 |
| NUCC-0226693 | 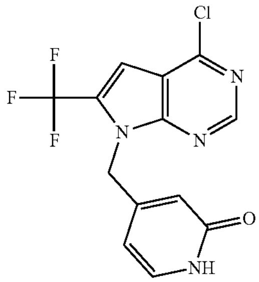 [SMILES: O=c1cc(Cn2c(C(F)(F)F)cc3c(Cl)ncnc32)cc[nH]1] | 2.01 | Core A1-031 |

TABLE 1-continued
| Inhibitory activity of compounds | | | |
|---|---|---|---|
| Molecule Name | Structure | IC50 (uM) [Cell Type: MV-4-11] | Synonym |
| NUCC-0226694 | 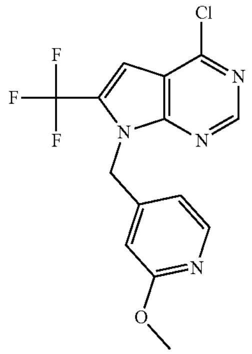 [SMILES: COc1cc(Cn2c(C(F)(F)F)cc3c(Cl)ncnc32)ccn1] | 0.999 | Core A1-031_3 |
| NUCC-0226695 | 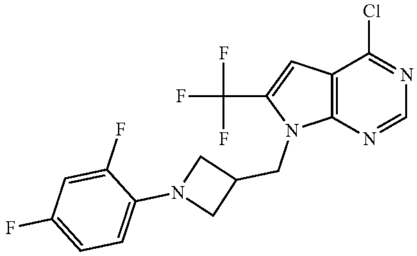 [SMILES: Fc1ccc(N2CC(Cn3c(C(F)(F)F)cc4c(Cl)ncnc43)C2)c(F)c1] | 0.739 | Core A1-010 |
| NUCC-0226696 | 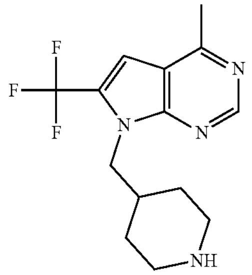 [SMILES: Cc1ncnc2c1cc(C(F)(F)F)n2CC1CCNCC1] | >20.0 | Core A1-036 |
| NUCC-0226697 | 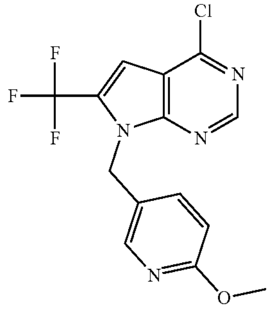 [SMILES: COc1ccc(Cn2c(C(F)(F)F)cc3c(Cl)ncnc32)cn1] | 1.08 | Core A1-030_3 |

TABLE 1-continued

| Inhibitory activity of compounds | | | |
|---|---|---|---|
| Molecule Name | Structure | IC50 (uM) [Cell Type: MV-4-11] | Synonym |
| NUCC-0226698 | 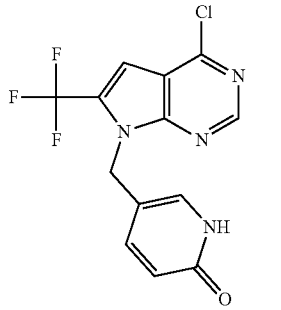 [SMILES: O=c1ccc(Cn2c(C(F)(F)F)cc3c(Cl)ncnc32)c[nH]1] | 1.26 | Core A1-030 |
| NUCC-0226699 | 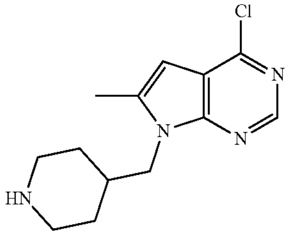 [SMILES: Cc1cc2c(Cl)ncnc2n1CC1CCNCC1] | >20.0 | Core A1-042 |
| NUCC-0226701 | 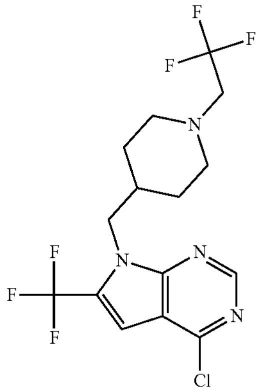 [SMILES: FC(F)(F)CN1CCC(Cn2c(C(F)(F)F)cc3c(Cl)ncnc32)CC1] | 0.919 | Core A1-014A |

Example 3—Inhibition of Cell Proliferation

Figure 2:
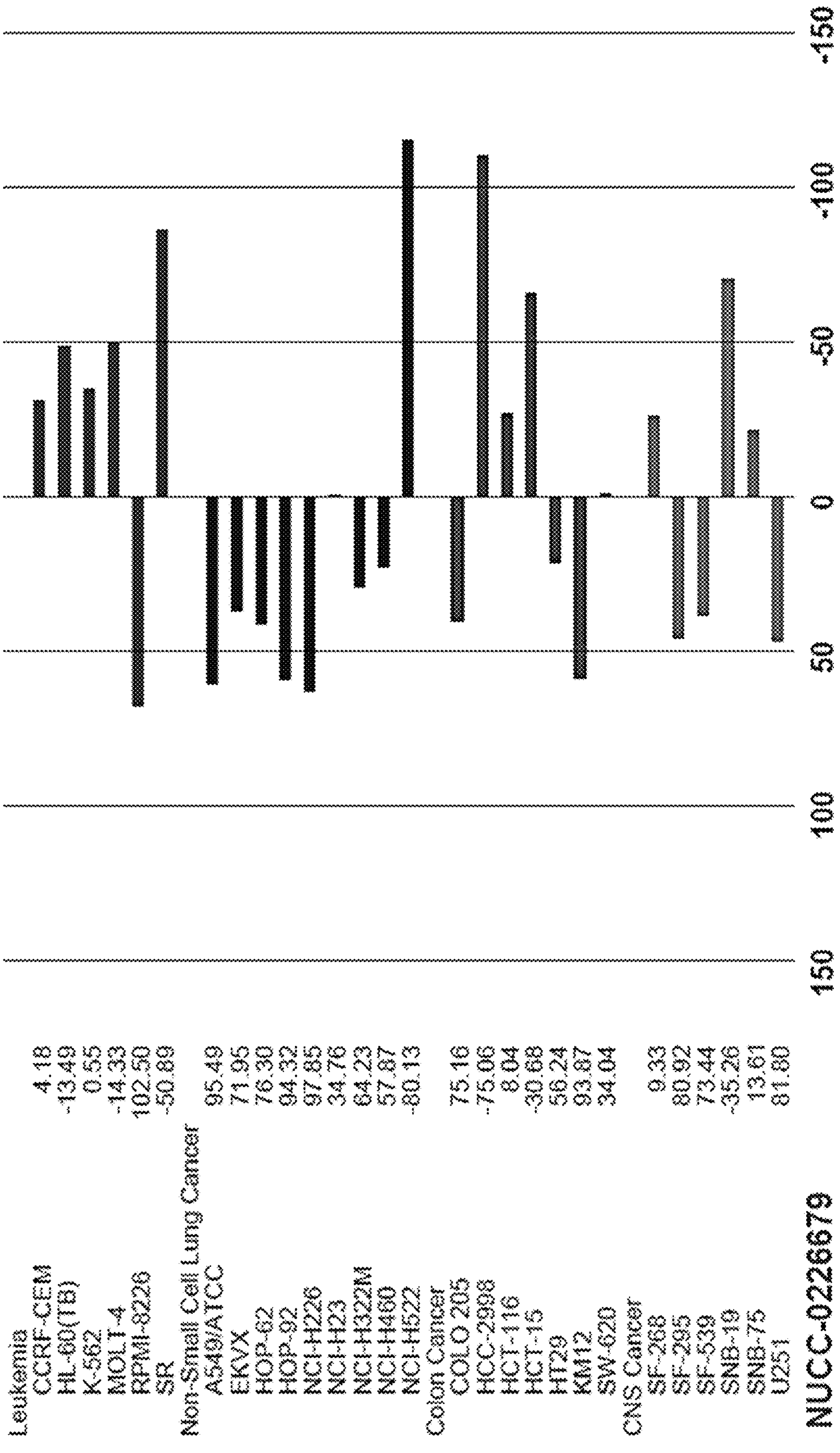
FIG. 2 shows single dose data demonstrating the effect of the compound NUCC-0226679 on various cancer cell lines. Negative growth percent indicates the amount of cancer cells in a specific cancer cell line being killed by the compound NUCC-0226679, compared to the amount of cancer cells present at the start of the treatment.
Figure 2:
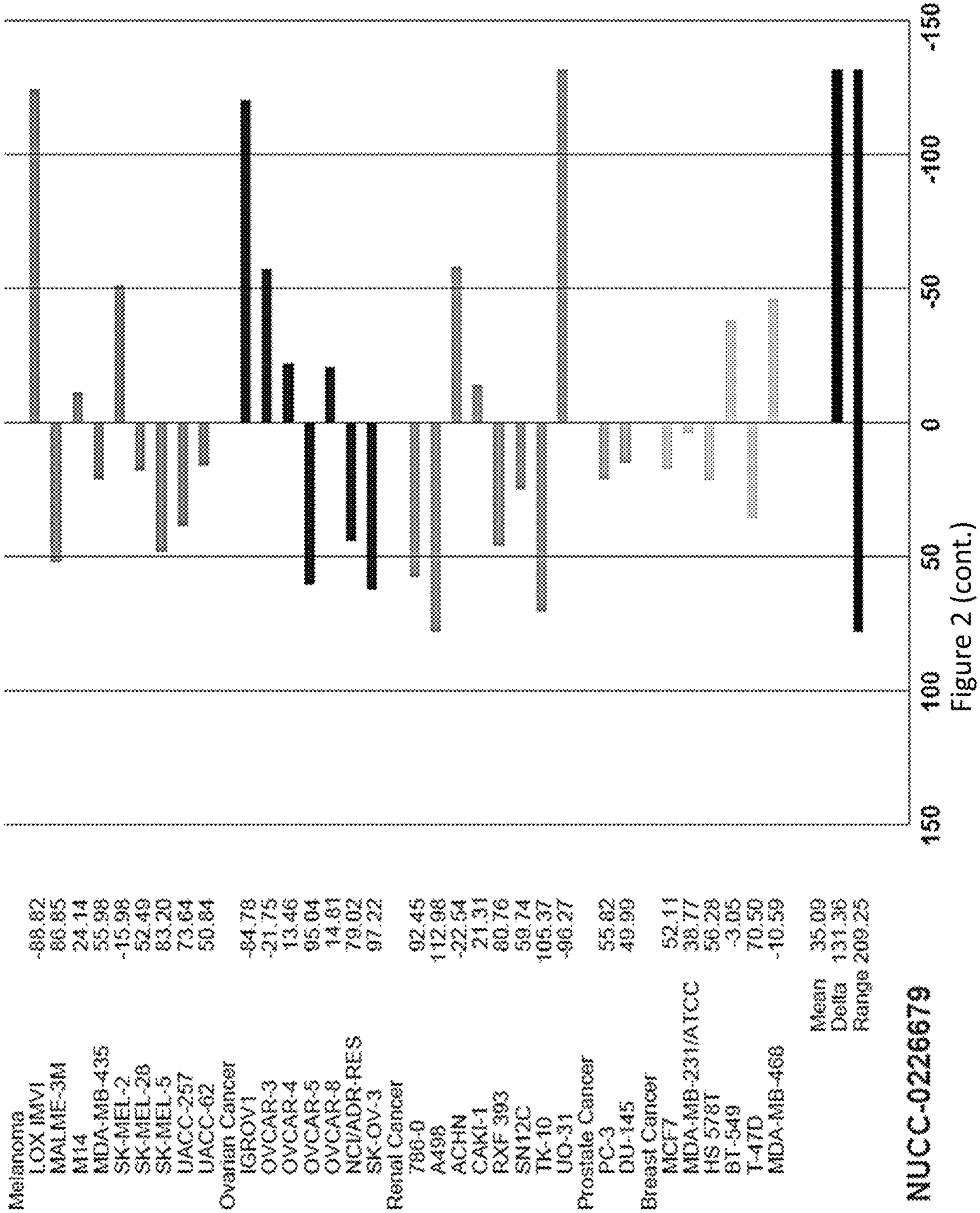
Figure 3:
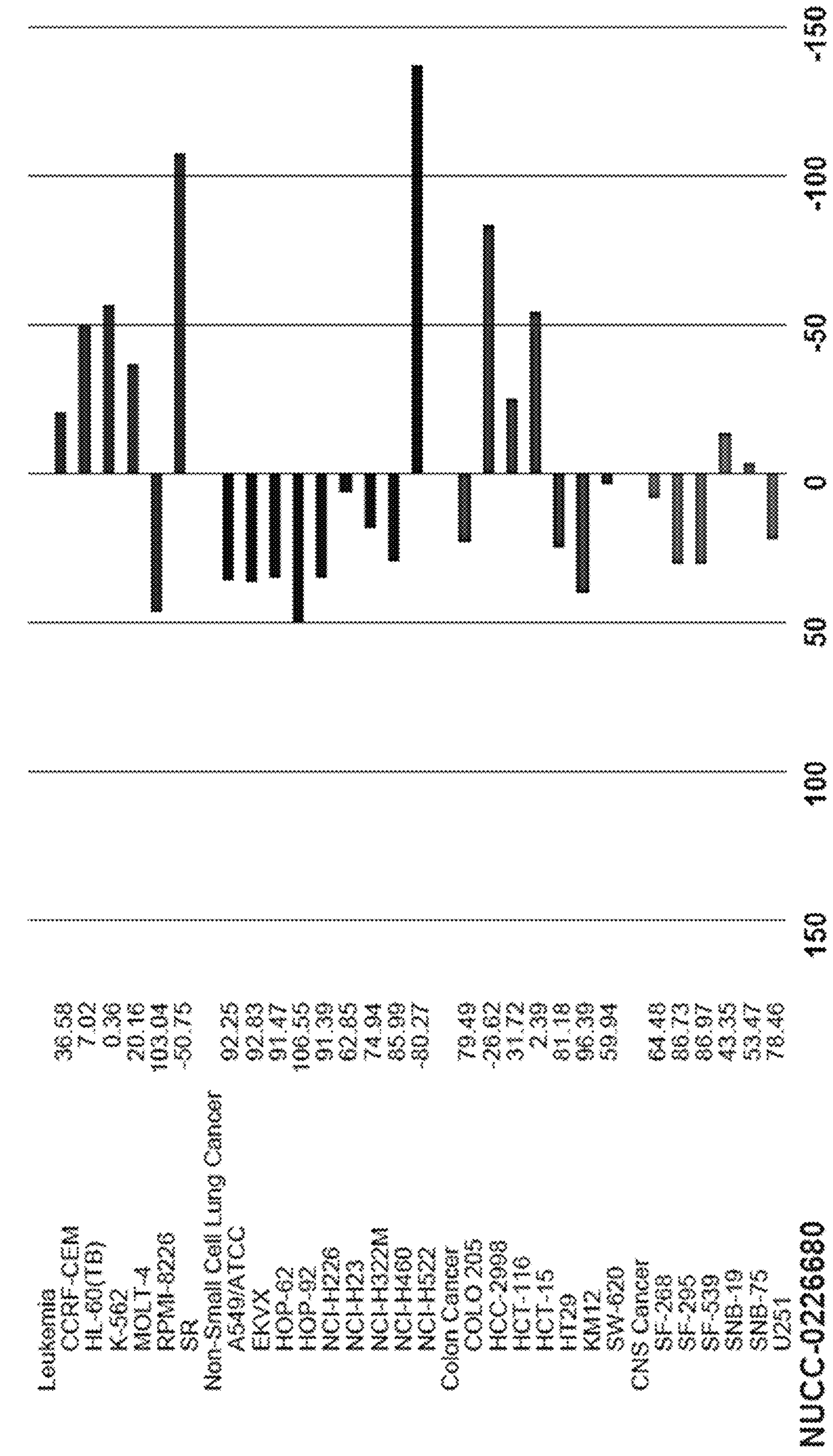
FIG. 3 demonstrates single dose data demonstrating the effect of the compound NUCC-0226680 on various cancer cell lines. Negative growth percent indicates the amount of cancer cells in a specific cancer cell line being killed by the compound NUCC-0226680, compared to the amount of cancer cells present at the start of the treatment.
Figure 3:
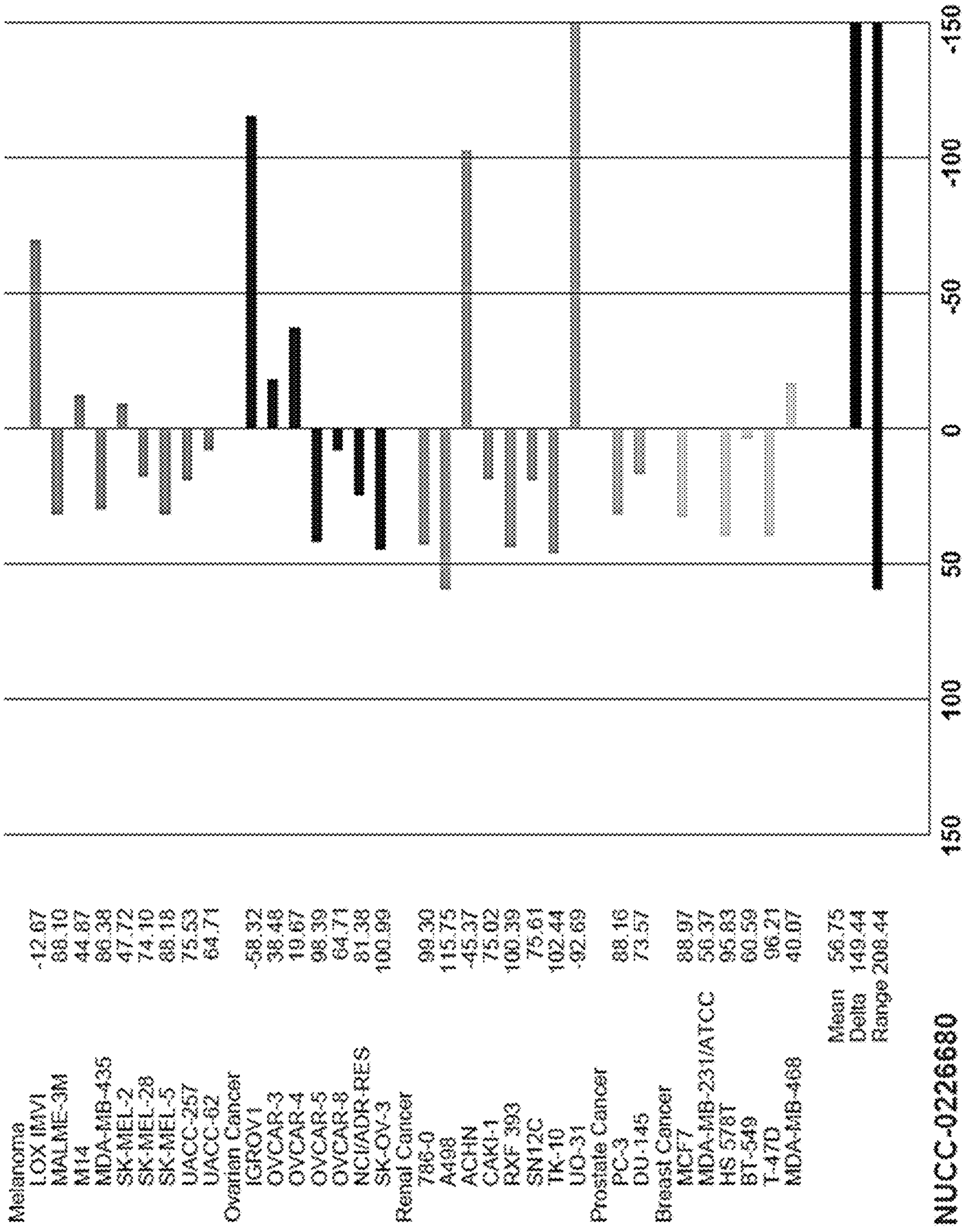
Figure 4:
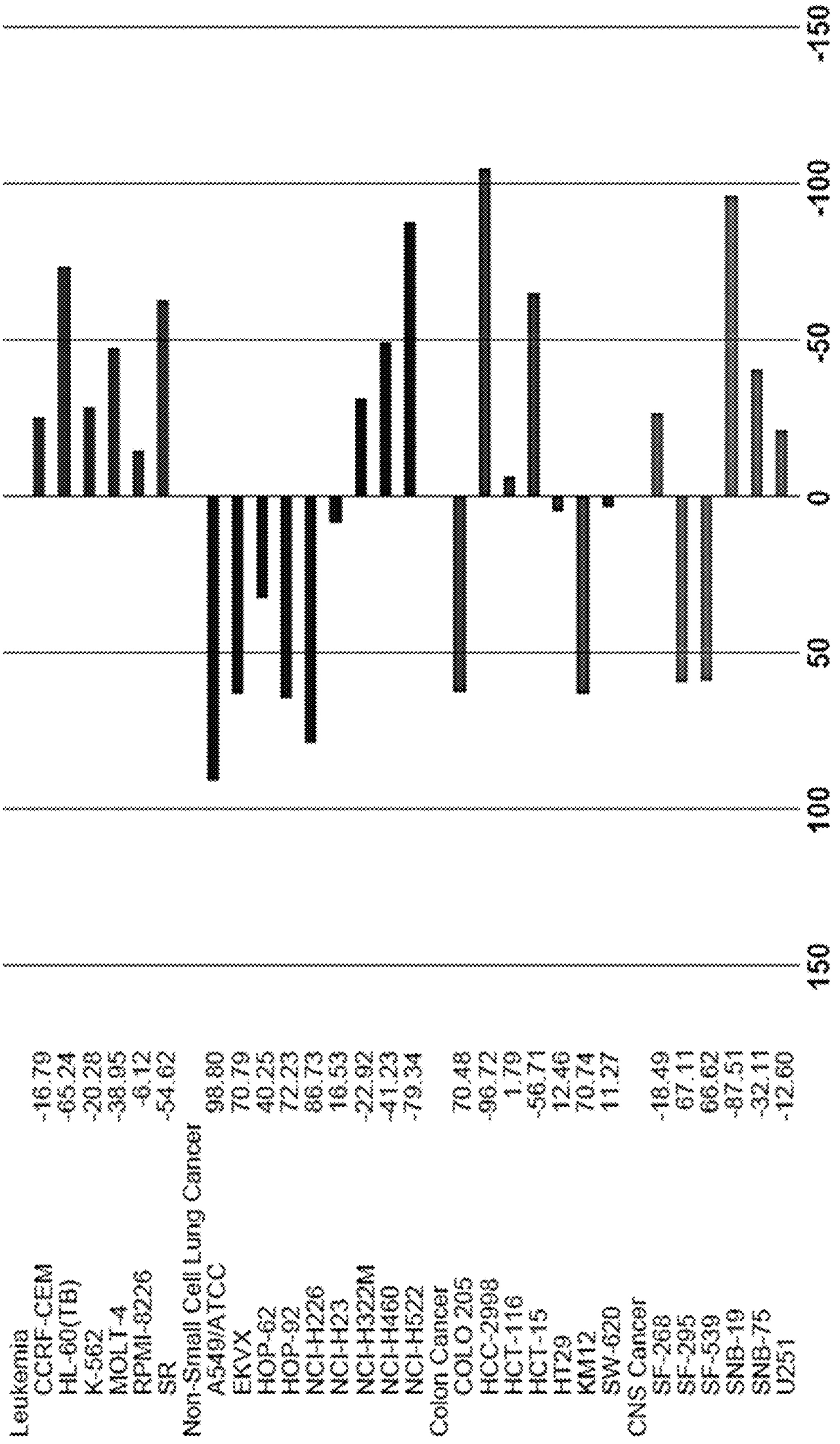
FIG. 4 demonstrates single dose data demonstrating the effect of the compound NUCC-0226683 on various cancer cell lines. Negative growth percent indicates the amount of cancer cells in a specific cancer cell line being killed by the compound NUCC-0226683, compared to the amount of cancer cells present at the start of the treatment.
Figure 4:
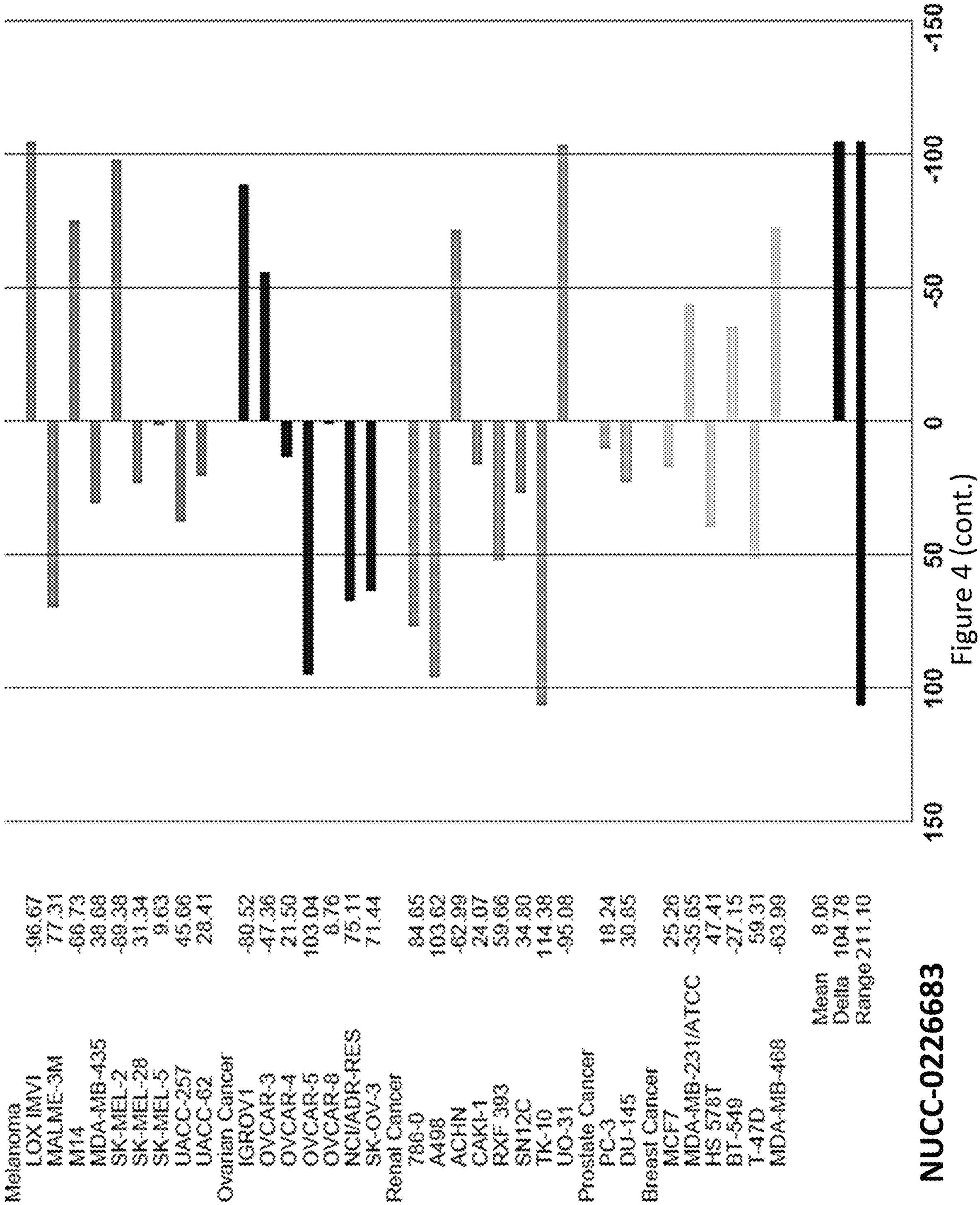
Figure 5:
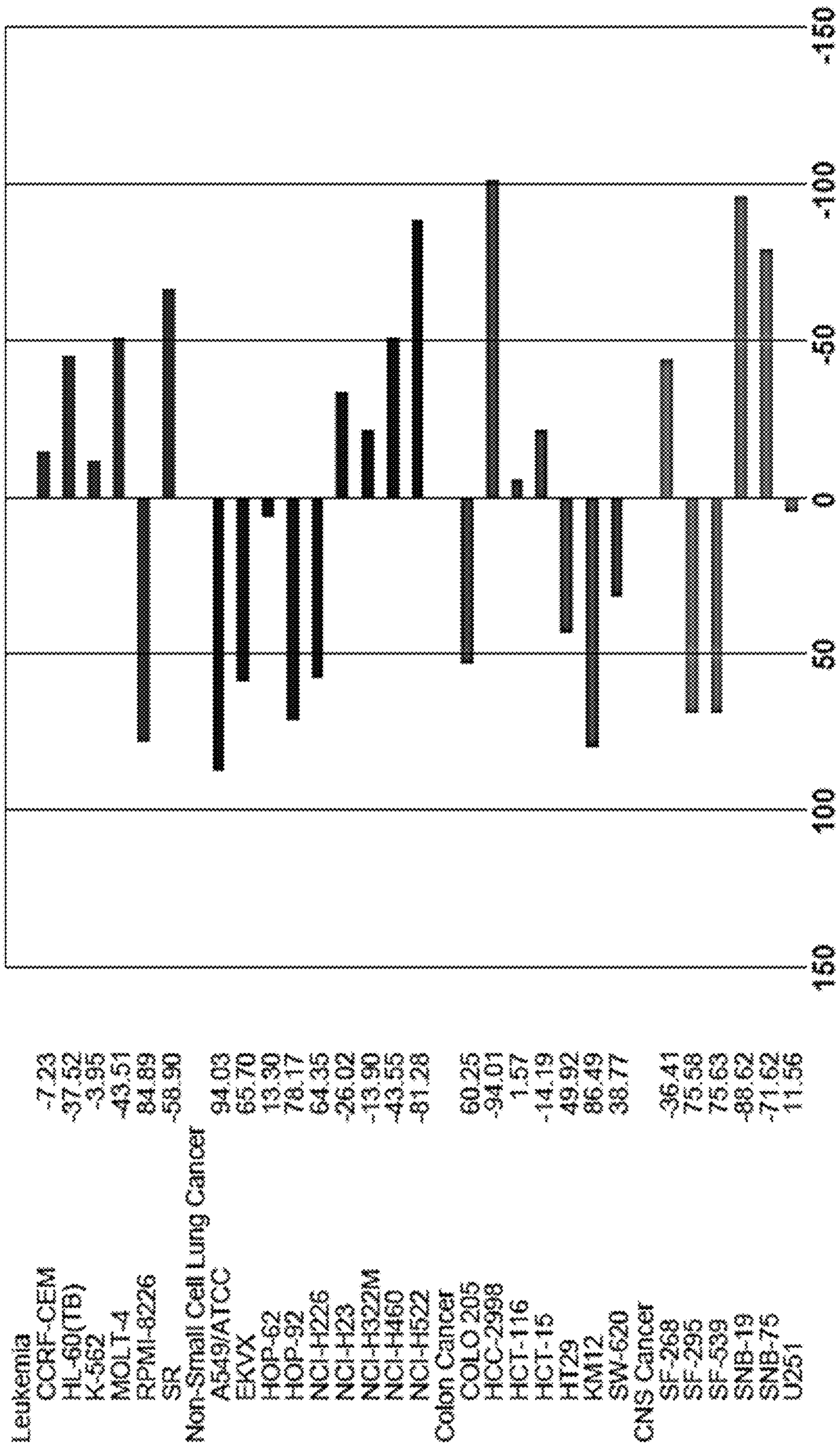
FIG. 5 illustrates single dose data demonstrating the effect of the compound NUCC-0226689 on various cancer cell lines. Negative growth percent indicates the amount of cancer cells in a specific cancer cell line being killed by the compound NUCC-0226689, compared to the amount of cancer cells present at the start of the treatment.
Figure 5:
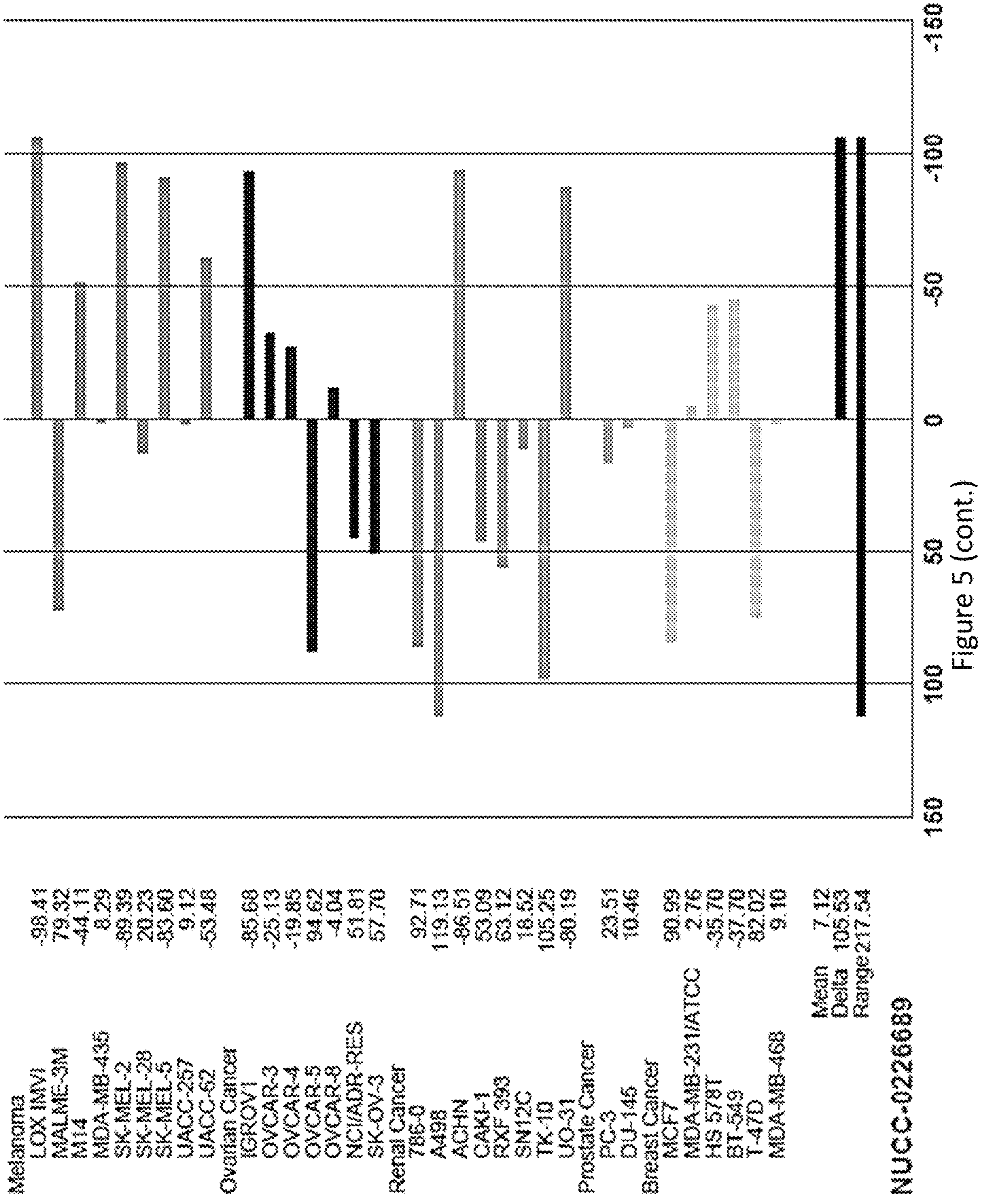
Figure 6:
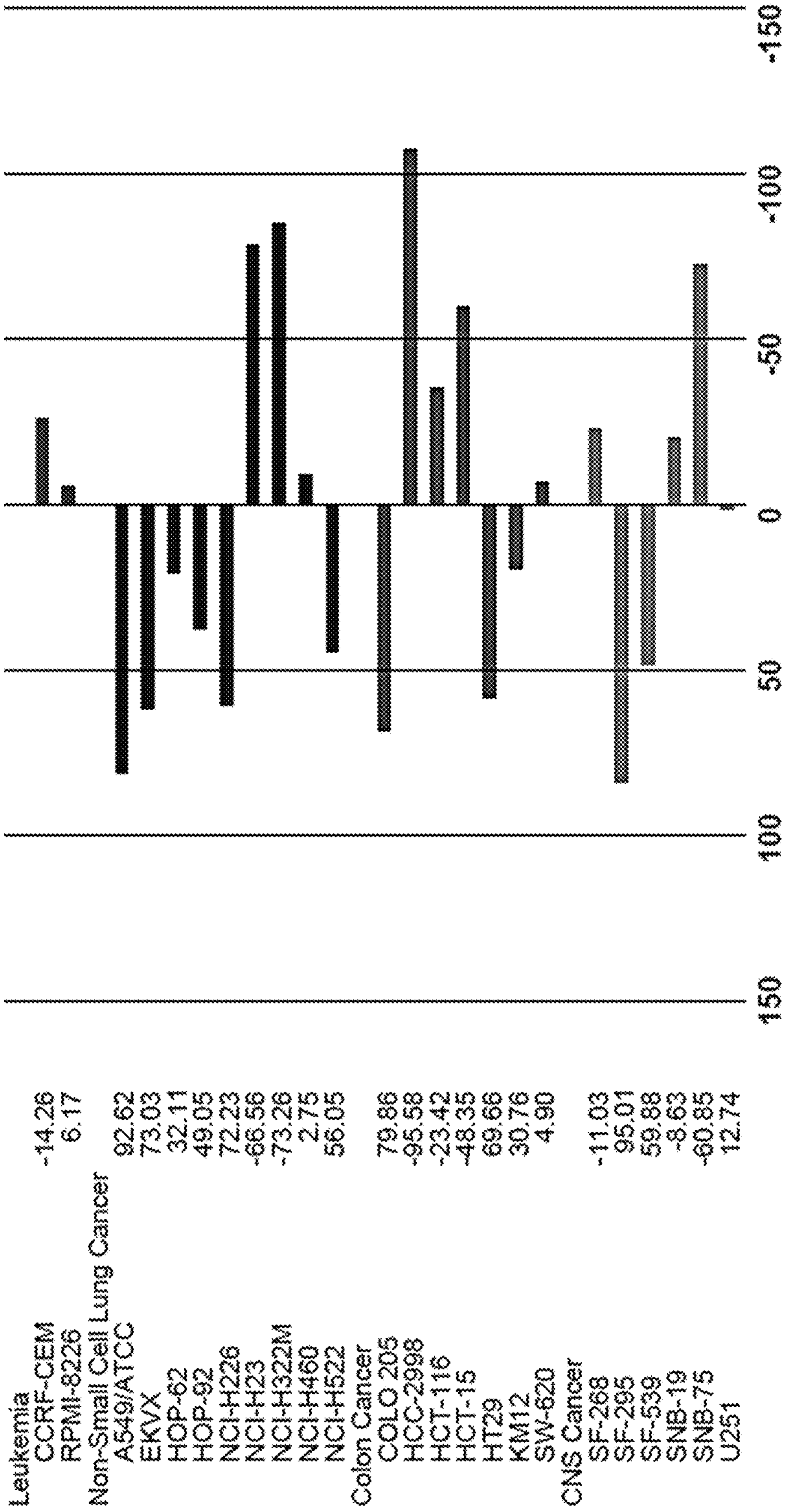
FIG. 6 illustrates single dose data demonstrating the effect of the compound NUCC-0226694 on various cancer cell lines. Negative growth percent indicates the amount of cancer cells in a specific cancer cell line being killed by the compound NUCC-0226694, compared to the amount of cancer cells present at the start of the treatment.
Figure 6:
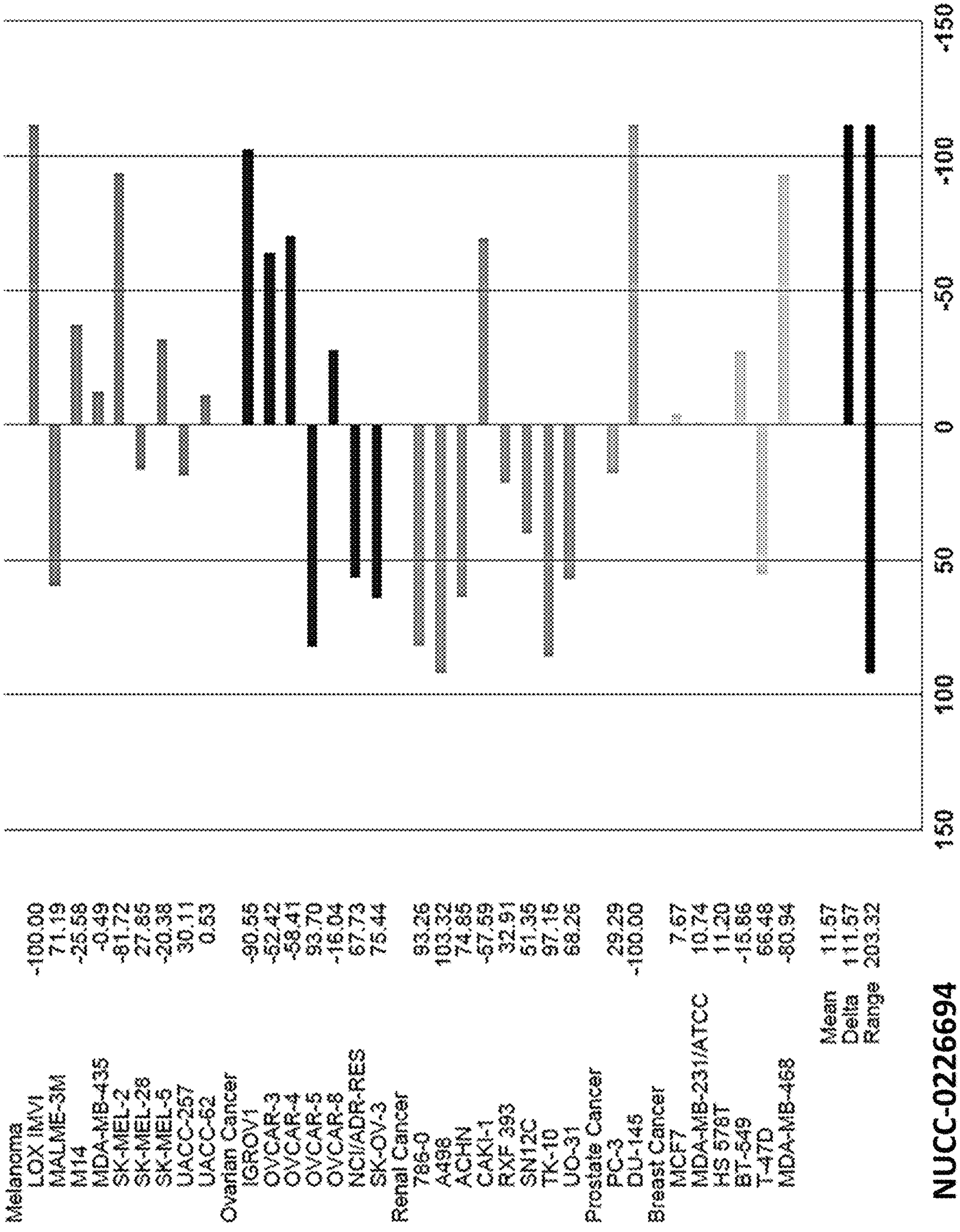
Figure 7:
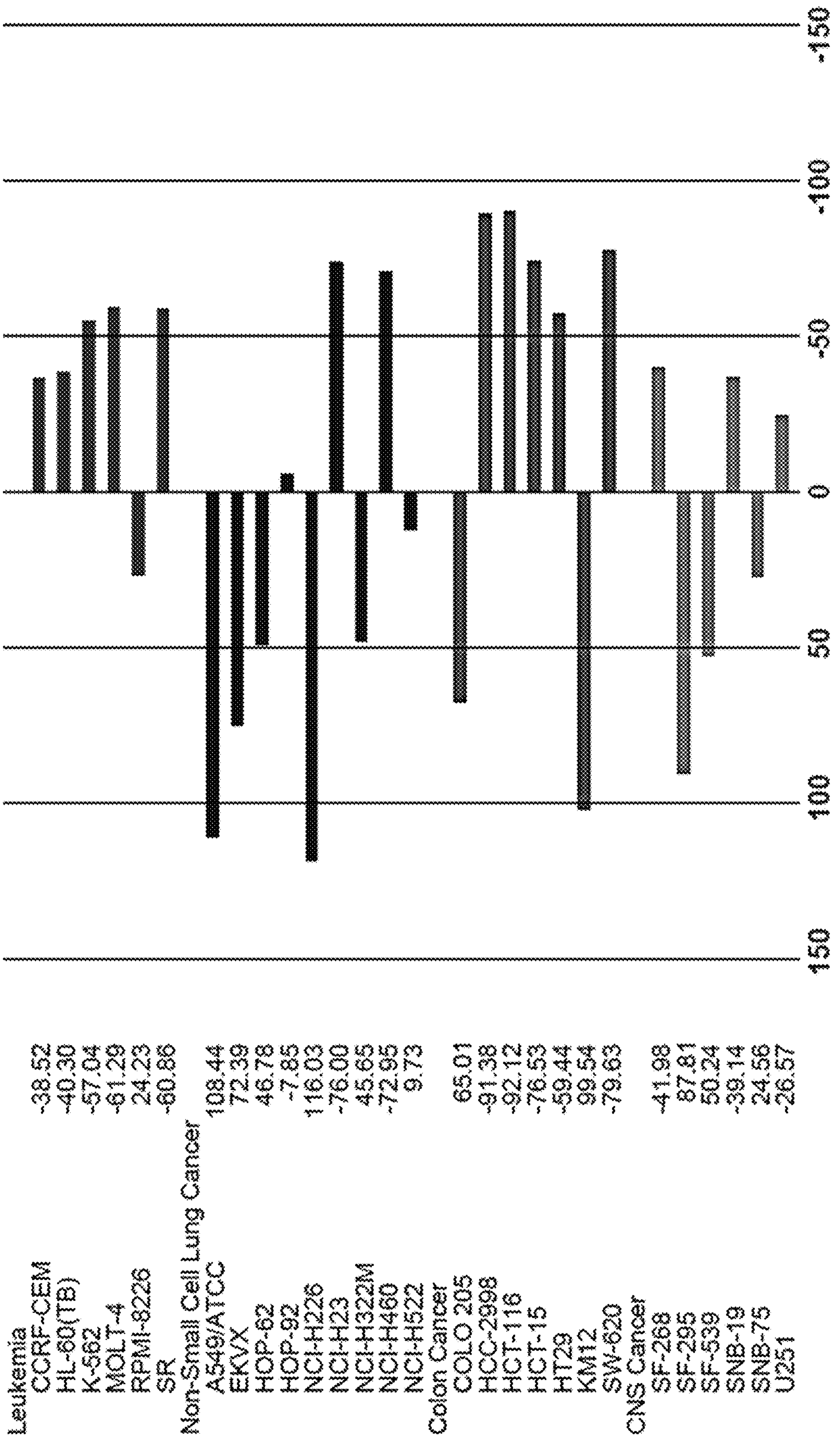
FIG. 7 shows single dose data demonstrating the effect of the compound NUCC-0226695 on various cancer cell lines. Negative growth percent indicates the amount of cancer cells in a specific cancer cell line being killed by the compound NUCC-0226695, compared to the amount of cancer cells present at the start of the treatment.
Figure 7:
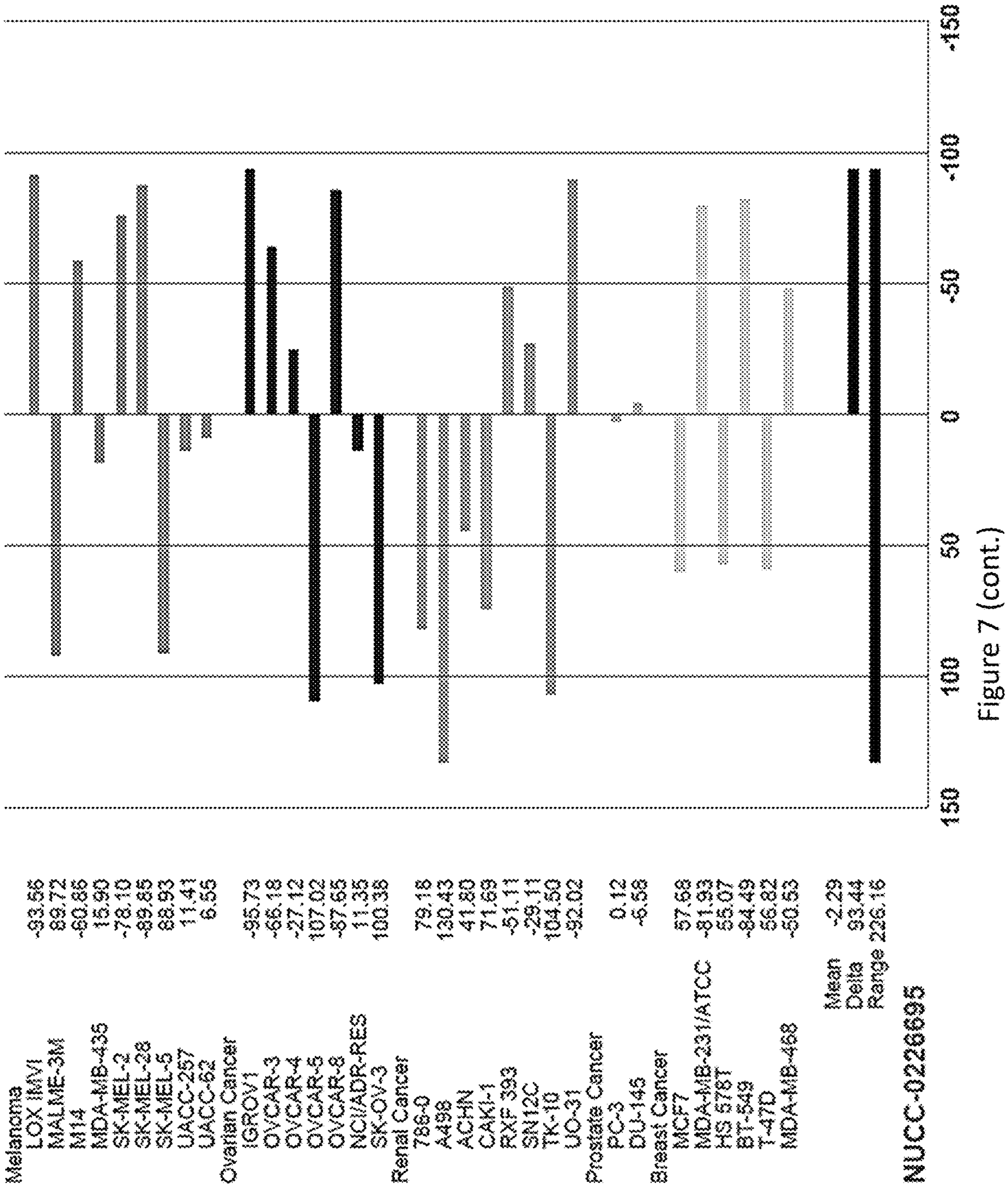
Figure 8:
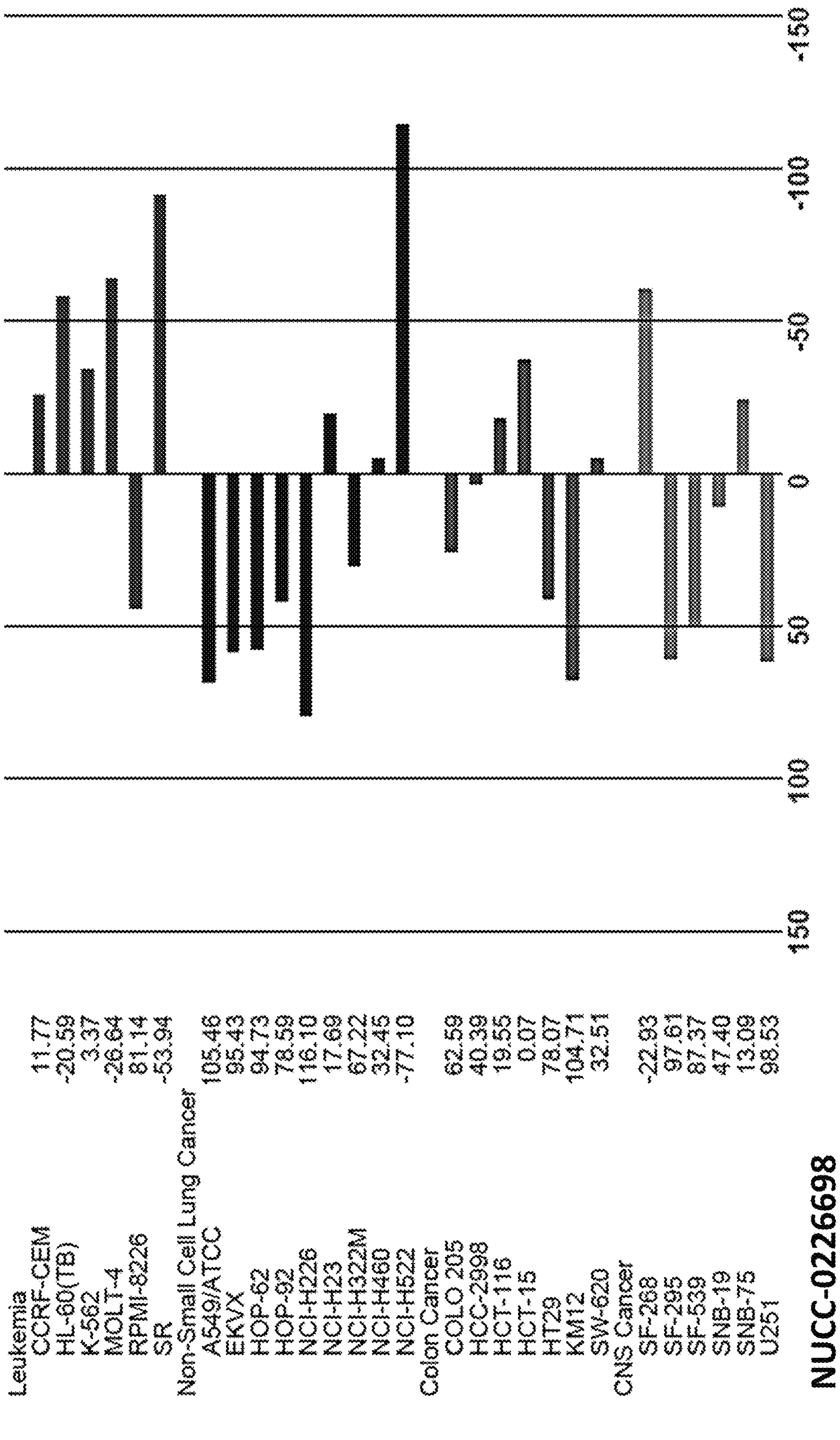
FIG. 8 shows single dose data demonstrating the effect of the compound NUCC-0226698 on various cancer cell lines. Negative growth percent indicates the amount of cancer cells in a specific cancer cell line being killed by the compound NUCC-0226698, compared to the amount of cancer cells present at the start of the treatment.
Figure 8:
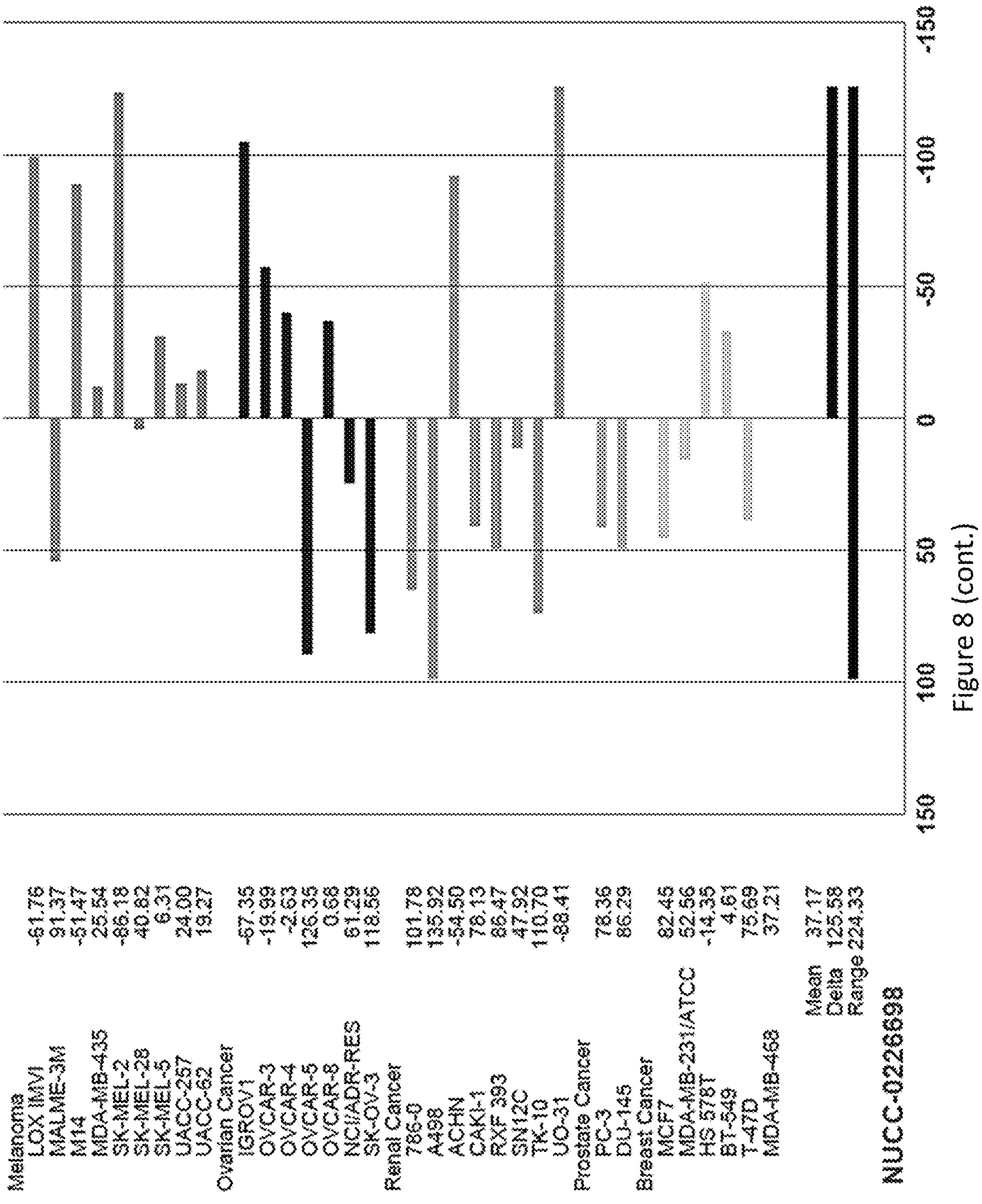

Compounds were submitted to the NCI 60 Cell screen and tested at a single high dose ($10^{-5}$ M) in the full NCI 60 cell panel (see the following reference for details of using NCI 60 human tumor cell lines for screening anticancer drugs: Shoemaker R H. The NCI60 human tumor cell line anticancer drug screen. Nature Rev Cancer 2006; 6: 813-23). The One-dose data is reported as a mean graph of the percent growth of treated cells. The number reported for the One-dose assay is growth relative to the no-drug control, and relative to the time zero number of cells. This allows detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead. FIGS. 1-8 show the mean graph of percent growth against the NCI-60 cell panel for NUCC-0226674, NUCC-0226679, NUCC-0226680, NUCC-0226683, NUCC-0226689, NUCC-0226694, NUCC-0226695, and NUCC-0226698.

The compounds NUCC-0226674, NUCC-0226679, NUCC-0226680, NUCC-0226683, NUCC-0226689, NUCC-0226694, NUCC-0226695, and NUCC-0226698, which exhibit significant growth inhibition in the One-Dose Screen, are then evaluated against the 60 cell panel at five concentration levels.

NCI 60 Cell Five-Dose Screening Results for Selected Compounds

NUCC-0226674

| | NUCC-0226674 all data in units of −log[M] | | | |
|---|---|---|---|---|
| Cell Line | GI50 | IC50 | LC50 | TGI |
| CCRF-CEM | 5.85 | 5.6 | 4 | 5.34 |
| HL-60(TB) | 5.65 | 5.38 | 4.35 | 5.3 |
| K-562 | 5.55 | 5.44 | 4 | 5.06 |
| MOLT-4 | 5.63 | 5.37 | 4 | 5.26 |
| RPMI-8226 | 4.84 | 4.59 | 4 | 4.38 |

-continued

| Cell Line | NUCC-0226674 all data in units of −log[M] | | | |
|---|---|---|---|---|
| | GI50 | IC50 | LC50 | TGI |
| SR | 5.69 | 5.43 | 4 | 5.27 |
| A549/ATCC | 4.66 | 4.46 | 4 | 4.25 |
| EKVX | 4.9 | 4.59 | 4.19 | 4.55 |
| HOP-62 | 4.77 | 4.48 | 4.14 | 4.45 |
| HOP-92 | 4.86 | 4.46 | 4.12 | 4.49 |
| NCI-H226 | 4.86 | 4.52 | 4.23 | 4.54 |
| NCI-H23 | 5.59 | 5.31 | 4.46 | 5 |
| NCI-H322M | 5.5 | 5.08 | 4.45 | 4.9 |
| NCI-H460 | 5.62 | 5.45 | 4.65 | 5.25 |
| NCI-H522 | 5.77 | 5.47 | 5.09 | 5.43 |
| COLO 205 | 4.79 | 4.52 | 4.07 | 4.43 |
| HCC-2998 | 5.79 | 5.53 | 5.25 | 5.52 |
| HCT-116 | 5.63 | 5.49 | 4.54 | 5.19 |
| HCT-15 | 5.53 | 5.42 | 4.38 | 4.96 |
| HT29 | 4.86 | 4.67 | 4 | 4.35 |
| KM12 | 4.79 | 4.55 | 4.15 | 4.47 |
| SW-620 | 4.92 | 4.76 | 4.17 | 4.55 |
| SF-268 | 5.61 | 5.34 | 4.35 | 5.14 |
| SF-295 | 4.86 | 4.6 | 4.25 | 4.56 |
| SF-539 | 4.86 | 4.61 | 4.25 | 4.56 |
| SNB-19 | 5.28 | 4.91 | 4.36 | 4.74 |
| SNB-75 | 5.51 | 4.81 | 4.4 | 4.82 |
| U251 | 5.68 | 5.49 | 4.55 | 5.25 |
| LOX IMVI | 5.79 | 5.54 | 5.26 | 5.52 |
| MALME-3M | 4.82 | 4.53 | 4.25 | 4.53 |
| M14 | 5.43 | 5.2 | 4.3 | 4.79 |
| MDA-MB-435 | 5.3 | 5.09 | 4.31 | 4.74 |
| SK-MEL-2 | 4.88 | 4.53 | 4.22 | 4.55 |
| SK-MEL-28 | 5.58 | 5.34 | 4.67 | 5.22 |
| SK-MEL-5 | 5.55 | 5.36 | 4.52 | 5.03 |
| UACC-257 | 5.45 | 5.03 | 4.28 | 4.81 |
| UACC-62 | 5.37 | 5.09 | 4.39 | 4.8 |
| IGROV1 | 5.75 | 5.5 | 5.17 | 5.46 |
| OVCAR-3 | 4.91 | 4.63 | 4.21 | 4.56 |
| OVCAR-4 | 4.73 | 4.42 | 4 | 4.3 |
| OVCAR-5 | 4.62 | 4.34 | 4 | 4.09 |
| OVCAR-8 | 5.61 | 5.44 | 4.2 | 5.13 |
| NCI/ADR-RES | 4.77 | 4.51 | 4.14 | 4.45 |
| SK-OV-3 | 4.76 | 4.48 | 4.19 | 4.48 |
| 786-0 | 4.79 | 4.55 | 4.19 | 4.49 |
| A498 | 4.79 | 4.51 | 4.26 | 4.52 |
| ACHN | 4.96 | 4.73 | 4.21 | 4.58 |
| CAKI-1 | 4.84 | 4.57 | 4.2 | 4.52 |
| RXF 393 | 5.06 | 4.62 | 4.29 | 4.66 |
| SN12C | 5.18 | 4.9 | 4.33 | 4.7 |
| TK-10 | 4.76 | 4.44 | 4.11 | 4.44 |
| UO-31 | 5.75 | 5.47 | 5.1 | 5.42 |
| PC-3 | 5.53 | 5.37 | 4.34 | 4.95 |
| DU-145 | 5.36 | 5.14 | 4.4 | 4.82 |
| MCF7 | 4.94 | 4.72 | 4 | 4.44 |
| MDA-MB-231/ATCC | 5.41 | 5.09 | 4.36 | 4.85 |
| HS 578T | 4.92 | 4.15 | 4 | 4.34 |
| BT-549 | 4.99 | 4.63 | 4.3 | 4.65 |
| T-47D | 4.69 | 4.32 | 4 | 4.22 |
| MDA-MB-468 | 5.78 | 5.42 | 5.14 | 5.46 |

NUCC-0226679

| Cell Line | NUCC-0226679 all data in units of −log[M] | | | |
|---|---|---|---|---|
| | GI50 | IC50 | LC50 | TGI |
| CCRF-CEM | 4.96 | 4.13 | 4 | 4 |
| HL-60(TB) | 5.68 | 5.36 | 4 | 5.13 |
| K-562 | 5.54 | 5.44 | 4 | 4 |
| MOLT-4 | 4.98 | 4.6 | 4 | 4.26 |
| RPMI-8226 | 4.5 | 4.34 | 4 | 4 |
| SR | 5.48 | 5.21 | 4 | 4.58 |
| A549/ATCC | 4.1 | 4 | 4 | 4 |
| EKVX | 4.79 | 4.29 | 4 | 4.07 |
| HOP-62 | 4.42 | 4 | 4 | 4 |
| HOP-92 | 4.71 | 4.2 | 4 | 4.27 |
| NCI-H226 | 4.22 | 4 | 4 | 4 |
| NCI-H23 | 4.86 | 4.55 | 4 | 4.41 |
| NCI-H322M | 4.81 | 4.44 | 4 | 4.36 |
| NCI-H460 | 4.74 | 4.58 | 4 | 4.3 |
| NCI-H522 | 5.77 | 5.49 | 0 | 5.46 |
| COLO 205 | 4.28 | 4 | 4 | 4 |
| HCC-2998 | 5.39 | 5.08 | 4.39 | 4.84 |
| HCT-116 | 5.31 | 5.22 | 4.17 | 4.69 |
| HCT-15 | 5.5 | 5.38 | 4.26 | 4.89 |
| HT29 | 4.68 | 4.53 | 4 | 4.09 |
| KM12 | 4.53 | 4.38 | 4 | 4 |
| SW-620 | 4.95 | 4.8 | 4.13 | 4.54 |
| SF-268 | 4.79 | 4.51 | 4.03 | 4.41 |
| SF-295 | 4.65 | 4.39 | 4 | 4.06 |
| SF-539 | 4.77 | 4.5 | 4.12 | 4.44 |
| SNB-19 | 4.82 | 4.55 | 4.19 | 4.51 |
| SNB-75 | 4.98 | 4.64 | 4.32 | 4.65 |
| U251 | 4.85 | 4.64 | 4.06 | 4.46 |
| LOX IMVI | 5.77 | 5.53 | 5.24 | 5.51 |
| MALME-3M | 4.72 | 4.2 | 4 | 4.26 |
| M14 | 4.89 | 4.65 | 4.06 | 4.48 |
| MDA-MB-435 | 4.88 | 4.66 | 4.17 | 4.52 |
| SK-MEL-2 | 4.78 | 4.47 | 4.18 | 4.48 |
| SK-MEL-28 | 4.8 | 4.52 | 4.05 | 4.42 |
| SK-MEL-5 | 4.83 | 4.58 | 4.19 | 4.51 |
| UACC-257 | 4.93 | 4.6 | 4.11 | 4.52 |
| UACC-62 | 4.92 | 4.65 | 4.12 | 4.52 |
| IGROV1 | 5.53 | 5.36 | 4.42 | 4.99 |
| OVCAR-3 | 4.75 | 4.48 | 4.14 | 4.45 |
| OVCAR-4 | 4.55 | 4.15 | 4 | 4 |
| OVCAR-5 | 4 | 4 | 4 | 4 |
| OVCAR-8 | 4.9 | 4.69 | 4.06 | 4.48 |
| NCI/ADR-RES | 4.62 | 4.37 | 4 | 4.19 |
| SK-OV-3 | 4.28 | 4 | 4 | 4 |
| 786-0 | 4.4 | 4.18 | 4 | 4 |
| A498 | 4 | 4 | 4 | 4 |
| ACHN | 5.19 | 4.77 | 4 | 4 |
| CAKI-1 | 4.6 | 4.32 | 4 | 4 |
| RXF 393 | 4.81 | 4.34 | 4 | 4.39 |
| SN12C | 4.71 | 4.46 | 4 | 4 |
| TK-10 | 4 | 4 | 4 | 4 |
| UO-31 | 5.76 | 5.48 | 5.13 | 5.45 |
| PC-3 | 4.82 | 4.59 | 4 | 4.32 |
| DU-145 | 4.52 | 4.3 | 4 | 4 |
| MCF7 | 4.71 | 4.52 | 4 | 4.12 |
| MDA-MB-231/ATCC | 5.26 | 4.84 | 4.3 | 4.71 |
| HS 578T | 4.78 | 4 | 4 | 4.22 |
| BT-549 | 4.82 | 4.52 | 4.23 | 4.53 |
| T-47D | 4.66 | 4.15 | 4 | 4 |
| MDA-MB-468 | 5.52 | 4.74 | 4.41 | 5.03 |

NUCC-0226680

| Cell Line | NUCC-0226680 all data in units of −log[M] | | | |
|---|---|---|---|---|
| | GI50 | IC50 | LC50 | TGI |
| CCRF-CEM | 4.78 | 4.45 | 4 | 4 |
| HL-60(TB) | 5.68 | 5.41 | 4.18 | 5.22 |
| K-562 | 5.52 | 5.43 | 4 | 4.73 |
| MOLT-4 | 5.24 | 4.97 | 4 | 4.54 |
| RPMI-8226 | 4.5 | 4.33 | 4 | 4 |
| SR | 5.54 | 5.36 | 4 | 4.9 |
| A549/ATCC | 4 | 4 | 4 | 4 |
| EKVX | 4.77 | 4.3 | 4 | 4.02 |
| HOP-62 | 4.41 | 4 | 4 | 4 |
| HOP-92 | 4.72 | 4.1 | 4 | 4.22 |
| NCI-H226 | 4 | 4 | 4 | 4 |
| NCI-H23 | 4.75 | 4.43 | 4 | 4.13 |
| NCI-H322M | 4.8 | 4.38 | 4 | 4.27 |

-continued

| Cell Line | NUCC-0226680 all data in units of −log[M] | | | |
|---|---|---|---|---|
| | GI50 | IC50 | LC50 | TGI |
| NCI-H460 | 4.63 | 4.55 | 4 | 4 |
| NCI-H522 | 5.83 | 5.53 | 0 | 5.48 |
| COLO 205 | 4.58 | 4.23 | 4 | 4 |
| HCC-2998 | 5.65 | 5.39 | 4.8 | 5.29 |
| HCT-116 | 5.33 | 5.25 | 4 | 4 |
| HCT-15 | 5.48 | 5.37 | 4 | 4.75 |
| HT29 | 4.56 | 4.44 | 4 | 4 |
| KM12 | 4.45 | 4.29 | 4 | 4 |
| SW-620 | 4.98 | 4.84 | 4 | 4.25 |
| SF-268 | 4.83 | 4.55 | 4.11 | 4.47 |
| SF-295 | 4.61 | 4.34 | 4 | 4 |
| SF-539 | 4.74 | 4.47 | 4.01 | 4.37 |
| SNB-19 | 4.81 | 4.54 | 4.15 | 4.48 |
| SNB-75 | 4.99 | 4.63 | 4.31 | 4.65 |
| U251 | 4.83 | 4.62 | 4 | 4.41 |
| LOX IMVI | 5.76 | 5.52 | 5.18 | 5.47 |
| MALME-3M | 4.66 | 4.06 | 4 | 4.17 |
| M14 | 4.94 | 4.69 | 4 | 4.44 |
| MDA-MB-435 | 4.88 | 4.65 | 4.19 | 4.53 |
| SK-MEL-2 | 4.76 | 4.47 | 4.19 | 4.48 |
| SK-MEL-28 | 4.87 | 4.6 | 4.1 | 4.48 |
| SK-MEL-5 | 4.89 | 4.64 | 4.17 | 4.53 |
| UACC-257 | 4.98 | 4.63 | 4.06 | 4.52 |
| UACC-62 | 4.97 | 4.68 | 4.01 | 4.49 |
| IGROV1 | 5.6 | 5.4 | 4.45 | 5.12 |
| OVCAR-3 | 4.71 | 4.43 | 4.01 | 4.36 |
| OVCAR-4 | 4.48 | 4 | 4 | 4 |
| OVCAR-5 | 4 | 4 | 4 | 4 |
| OVCAR-8 | 5.07 | 4.86 | 4.03 | 4.53 |
| NCI/ADR-RES | 4.52 | 4.24 | 4 | 4 |
| SK-OV-3 | 4 | 4 | 4 | 4 |
| 786-0 | 4.43 | 4.21 | 4 | 4 |
| A498 | 4 | 4 | 4 | 4 |
| ACHN | 5.12 | 4.81 | 4 | 4 |
| CAKI-1 | 4.56 | 4.25 | 4 | 4 |
| RXF 393 | 4.83 | 4.37 | 4 | 4.39 |
| SN12C | 4.71 | 4.41 | 4 | 4 |
| TK-10 | 4 | 4 | 4 | 4 |
| UO-31 | 5.6 | 5.27 | 4.43 | 5.05 |
| PC-3 | 4.95 | 4.72 | 4 | 4.44 |
| DU-145 | 4.54 | 4.3 | 4 | 4 |
| MCF7 | 4.6 | 4.45 | 4 | 4 |
| MDA-MB-231/ATCC | 5.36 | 4.94 | 4.27 | 4.74 |
| HS 578T | 4.78 | 4 | 4 | 4.23 |
| BT-549 | 4.87 | 4.55 | 4.23 | 4.55 |
| T-47D | 4.41 | 4 | 4 | 4 |
| MDA-MB-468 | 5.56 | 4.8 | 4.37 | 4.98 |

NUCC-0226683

| Cell Line | NUCC-0226683 all data in units of −log[M] | | | |
|---|---|---|---|---|
| | GI50 | IC50 | LC50 | TGI |
| CCRF-CEM | 5.36 | 5.13 | 4 | 4 |
| HL-60(TB) | 5.56 | 5.24 | 4 | 5.09 |
| K-562 | 5.55 | 5.46 | 4 | 4 |
| MOLT-4 | 5.62 | 5.38 | 4 | 5.04 |
| RPMI-8226 | 4.63 | 4.4 | 4 | 4.11 |
| SR | 5.67 | 5.45 | 4 | |
| A549/ATCC | 4.28 | 4.05 | 4 | 4 |
| EKVX | 4.93 | 4.54 | 4 | 4.39 |
| HOP-62 | 4.86 | 4.54 | 4.12 | 4.49 |
| HOP-92 | 4.89 | 4.49 | 4.18 | 4.53 |
| NCI-H226 | 4.76 | 4 | 4 | 4.14 |
| NCI-H23 | 5.23 | 4.83 | 4 | 4.57 |
| NCI-H322M | 5.26 | 4.8 | 4.35 | 4.72 |
| NCI-H460 | 5.57 | 5.44 | 4.51 | 5.17 |
| NCI-HS22 | 5.77 | 5.49 | 5.14 | 5.45 |
| COLO 205 | 4.73 | 4.47 | 4 | 4.34 |
| HCC-2998 | 5.74 | 5.49 | 5.23 | 5.48 |

-continued

| Cell Line | NUCC-0226683 all data in units of −log[M] | | | |
|---|---|---|---|---|
| | GI50 | IC50 | LC50 | TGI |
| HCT-116 | 5.5 | 5.43 | 4.19 | 4.88 |
| HCT-15 | 5.59 | 5.45 | 4.3 | 5.13 |
| HT29 | 5.26 | 5.13 | 4 | 4.44 |
| KM12 | 4.75 | 4.52 | 4.05 | 4.4 |
| SW-620 | 5.31 | 5.21 | 4.2 | 4.71 |
| SF-268 | 5.28 | 4.94 | 4.15 | 4.67 |
| SF-295 | 4.99 | 4.75 | 4.19 | 4.59 |
| SF-539 | 4.9 | 4.64 | 4.18 | 4.54 |
| SNB-19 | 4.88 | 4.62 | 4.27 | 4.57 |
| SNB-75 | 5.51 | 4.83 | 4.41 | 4.85 |
| U251 | 5.62 | 5.44 | 4.62 | 5.19 |
| LOX IMVI | 5.78 | 5.53 | 5.24 | 5.51 |
| MALME-3M | 4.84 | 4.47 | 4.15 | 4.49 |
| M14 | 5.21 | 4.91 | 4.17 | 4.64 |
| MDA-MB-435 | 5.26 | 5.04 | 4.29 | 4.71 |
| SK-MEL-2 | 4.8 | 4.5 | 4.22 | 4.51 |
| SK-MEL-28 | 5.09 | 4.78 | 4 | 4.43 |
| SK-MEL-5 | 5.43 | 5.21 | 4.43 | 4.86 |
| UACC-257 | 5.39 | 4.96 | 4.24 | 4.77 |
| UACC-62 | 5.33 | 5 | 4.32 | 4.74 |
| IGROV1 | 5.75 | 5.5 | 5.15 | 5.45 |
| OVCAR-3 | 4.84 | 4.54 | 4.08 | 4.46 |
| OVCAR-4 | 4.57 | 4.05 | 4 | 4 |
| OVCAR-5 | 4 | 4 | 4 | 4 |
| OVCAR-8 | 5.49 | 5.35 | 4.39 | 4.93 |
| NCI/ADR-RES | 4.72 | 4.45 | 4 | 4.33 |
| SK-OV-3 | 4.79 | 4.41 | 4 | 4.36 |
| 786-0 | 4.65 | 4.43 | 4 | 4.22 |
| A498 | 4.67 | 4 | 4 | 4.24 |
| ACHN | 4.91 | 4.65 | 4 | 4 |
| CAKI-1 | 4.87 | 4.59 | 4.16 | 4.51 |
| RXF 393 | 4.96 | 4.51 | 4.14 | 4.55 |
| SN12C | 5.11 | 4.86 | 4.22 | 4.64 |
| TK-10 | 4.45 | 4 | 4 | 4 |
| UO-31 | 5.79 | 5.52 | 5.18 | 5.49 |
| PC-3 | 5.45 | 5.3 | 4.24 | 4.92 |
| DU-145 | 4.9 | 4.65 | 4.06 | 4.48 |
| MCF7 | 5 | 4.8 | 4 | 4.37 |
| MDA-MB-231/ATCC | 5.75 | 5.47 | 4.94 | 5.37 |
| HS 578T | 4.85 | 4 | 4 | 4.22 |
| BT-549 | 4.89 | 4.57 | 4.26 | 4.57 |
| T-47D | 4.76 | 4.31 | 4 | 4.2 |
| MDA-MB-468 | 5.66 | 5.22 | 4.85 | 5.31 |

NUCC-0226689

| Cell Line | NUCC-0226689 all data in units of −log[M] | | | |
|---|---|---|---|---|
| | GI50 | IC50 | LC50 | TGI |
| CCRF-CEM | 5.25 | 5.03 | 4 | 4 |
| HL-60(TB) | 5.58 | 5.3 | 4 | 5.05 |
| K-562 | 5.54 | 5.45 | 4 | 4 |
| MOLT-4 | 5.56 | 5.35 | 4 | 5.09 |
| RPMI-8226 | 4.47 | 4.23 | 4 | 4 |
| SR | 5.67 | 5.45 | 4 | 5.17 |
| A549/ATCC | 4.51 | 4.36 | 4 | 4 |
| EKVX | 4.89 | 4.53 | 4 | 4.41 |
| HOP-62 | 4.7 | 4.37 | 4 | 4.24 |
| HOP-92 | 4.69 | 4.13 | 4 | 4.19 |
| NCI-H226 | 4.63 | 4 | 4 | 4.1 |
| NCI-H23 | 5.51 | 5.26 | 4.34 | 4.94 |
| NCI-H322M | 5.42 | 4.99 | 4.42 | 4.87 |
| NCI-H460 | 5.32 | 5.26 | 4.27 | 4.78 |
| NCI-H522 | 5.81 | 5.51 | 5.09 | 5.45 |
| COLO 205 | 4.61 | 4.34 | 4 | 4 |
| HCC-2998 | 5.75 | 5.49 | 5.21 | 5.48 |
| HCT-116 | 5.45 | 5.38 | 4.14 | 4.8 |
| HCT-15 | 5.43 | 5.32 | 4 | 4.7 |
| HT29 | 4.81 | 4.66 | 4 | 4 |
| KM12 | 4.58 | 4.43 | 4 | 4.03 |

-continued

| Cell Line | NUCC-0226689 all data in units of −log[M] | | | |
|---|---|---|---|---|
| | GI50 | IC50 | LC50 | TGI |
| SW-620 | 4.91 | 4.77 | 4 | 4.41 |
| SF-268 | 5.6 | 5.35 | 4.43 | 5.16 |
| SF-295 | 4.64 | 4.41 | 4 | 4.08 |
| SF-539 | 4.75 | 4.49 | 4.07 | 4.41 |
| SNB-19 | 4.87 | 4.62 | 4.27 | 4.57 |
| SNB-75 | 4.97 | 4.63 | 4.31 | 4.64 |
| U251 | 5.49 | 5.37 | 4.35 | 4.89 |
| LOX IMVI | 5.77 | 5.52 | 5.24 | 5.5 |
| MALME-3M | 4.75 | 4.07 | 4 | 4.19 |
| M14 | 5.31 | 5.06 | 4 | 4.57 |
| MDA-MB-435 | 4.92 | 4.7 | 4.26 | 4.59 |
| SK-MEL-2 | 4.88 | 4.54 | 4.23 | 4.55 |
| SK-MEL-28 | 5.03 | 4.72 | 4 | 4.51 |
| SK-MEL-5 | 5.32 | 5.08 | 4.37 | 4.78 |
| UACC-257 | 5.47 | 5.11 | 4.25 | 4.85 |
| UACC-62 | 5.27 | 4.94 | 4.29 | 4.71 |
| IGROV1 | 5.71 | 5.46 | 5.07 | 5.39 |
| OVCAR-3 | 5.09 | 4.72 | 4.01 | 4.54 |
| OVCAR-4 | 4.75 | 4.43 | 4 | 4.33 |
| OVCAR-5 | 4 | 4 | 4 | 4 |
| OVCAR-8 | 5.64 | 5.44 | 4.51 | 5.27 |
| NCI/ADR-RES | 4.58 | 4.36 | 4 | 4 |
| SK-OV-3 | 4.65 | 4.17 | 4 | 4 |
| 786-0 | 4.49 | 4.31 | 4 | 4 |
| A498 | 4 | 4 | 4 | 4 |
| ACHN | 5.06 | 4.81 | 4 | 4.3 |
| CAKI-1 | 4.78 | 4.48 | 4 | 4.28 |
| RXF 393 | 4.9 | 4.43 | 4.01 | 4.46 |
| SN12C | 5.27 | 5 | 4.27 | 4.7 |
| TK-10 | 4 | 4 | 4 | 4 |
| UO-31 | 4.82 | 4.41 | 4 | 4.18 |
| PC-3 | 5.05 | 4.81 | 4 | 4.44 |
| DU-145 | 5.1 | 4.86 | 4.33 | 4.69 |
| MCF7 | 4.43 | 4.28 | 4 | 4 |
| MDA-MB-231/ATCC | 5.35 | 4.96 | 4.16 | 4.7 |
| HS 578T | 4.86 | 4.03 | 4 | 4.27 |
| BT-549 | 4.88 | 4.55 | 4.23 | 4.55 |
| T-47D | 4.58 | 4.04 | 4 | 4 |
| MDA-MB-468 | 5.67 | 5.15 | 4.65 | 5.25 |

NUCC-0226694

| Cell Line | NUCC-0226694 all data in units of −log[M] | | | |
|---|---|---|---|---|
| | GI50 | IC50 | LC50 | TGI |
| CCRF-CEM | 5.5 | 5.27 | 4 | 4.73 |
| HL-60(TB) | 5.67 | 5.47 | 4 | 5.14 |
| K-562 | 5.63 | 5.57 | 4 | 4 |
| MOLT-4 | 5.48 | 5.34 | 4 | 4 |
| RPMI-8226 | 4.81 | 4.58 | 4 | 4.1 |
| SR | 5.44 | 5.32 | 4 | 4 |
| A549/ATCC | 4.78 | 4.56 | 4.05 | 4.42 |
| EKVX | 5.1 | 4.77 | 4.2 | 4.62 |
| HOP-62 | 4.84 | 4.56 | 4.21 | 4.53 |
| HOP-92 | 4.97 | 4.47 | 4.07 | 4.52 |
| NCI-H226 | 4.81 | 4.48 | 4.17 | 4.49 |
| NCI-H23 | 5.66 | 5.4 | 4.87 | 5.31 |
| NCI-H322M | 5.77 | 5.5 | 5.2 | 5.48 |
| NCI-H460 | 5.57 | 5.48 | 4.46 | 5.09 |
| NCI-H522 | 5.48 | 4.96 | 4.3 | 4.82 |
| COLO 205 | 4.82 | 4.58 | 4 | 4.33 |
| HCC-2998 | 5.75 | 5.5 | 5.22 | 5.49 |
| HCT-116 | 5.76 | 5.58 | 4.82 | 5.37 |
| HCT-15 | 5.51 | 5.42 | 4.27 | 5 |
| HT29 | 4.85 | 4.66 | 4 | 4.38 |
| KM12 | 4.87 | 4.64 | 4.16 | 4.52 |
| SW-620 | 5.41 | 5.31 | 4.31 | 4.78 |
| SF-268 | 5.61 | 5.34 | 4.38 | 5.03 |
| SF-295 | 4.78 | 4.52 | 4.2 | 4.49 |
| SF-539 | 4.86 | 4.61 | 4.29 | 4.57 |

-continued

| Cell Line | NUCC-0226694 all data in units of −log[M] | | | |
|---|---|---|---|---|
| | GI50 | IC50 | LC50 | TGI |
| SNB-19 | 4.93 | 4.67 | 4.31 | 4.62 |
| SNB-75 | 5.75 | 5.18 | 4.56 | 5.14 |
| U251 | 4.82 | 4.57 | 4.25 | 4.54 |
| LOX IMVI | 5.78 | 5.54 | 5.22 | 5.5 |
| MALME-3M | 4.9 | 4.59 | 4.29 | 4.59 |
| M14 | 5.82 | 5.57 | 4.78 | 5.38 |
| MDA-MB-435 | 5.49 | 5.32 | 4.3 | 4.84 |
| SK-MEL-2 | 5 | 4.66 | 4.29 | 4.65 |
| SK-MEL-28 | 5.34 | 5 | 4.39 | 4.79 |
| SK-MEL-5 | 5.41 | 5.16 | 4.42 | 4.85 |
| UACC-257 | 5.07 | 4.71 | 4.31 | 4.66 |
| UACC-62 | 5.09 | 4.8 | 4.34 | 4.69 |
| IGROV1 | 5.75 | 5.5 | 5.13 | 5.44 |
| OVCAR-3 | 5.63 | 5.39 | 4.51 | 5.15 |
| OVCAR-4 | 4.92 | 4.64 | 4.23 | 4.57 |
| OVCAR-5 | 4.8 | 4.53 | 4.18 | 4.49 |
| OVCAR-8 | 4.94 | 4.72 | 4.21 | 4.58 |
| NCI/ADR-RES | 4.82 | 4.56 | 4.13 | 4.47 |
| SK-OV-3 | 4.77 | 4.49 | 4.21 | 4.49 |
| 786-0 | 4.97 | 4.77 | 4.2 | 4.59 |
| A498 | 4.8 | 4.48 | 4.23 | 4.51 |
| ACHN | 4.84 | 4.6 | 4.24 | 4.54 |
| CAKI-1 | 5.14 | 4.86 | 4.33 | 4.69 |
| RXF 393 | 5.1 | 4.61 | 4.26 | 4.65 |
| SN12C | 5.04 | 4.81 | 4.33 | 4.67 |
| TK-10 | 4.72 | 4.34 | 4 | 4.33 |
| UO-31 | 5.06 | 4.74 | 4.21 | 4.62 |
| PC-3 | 5.26 | 5.02 | 4.23 | 4.68 |
| DU-145 | 5.75 | 5.51 | 5.23 | 5.49 |
| MCF7 | 5.29 | 5.14 | 4.21 | 4.7 |
| MDA-MB-231/ATCC | 5.48 | 5.1 | 4.37 | 4.9 |
| HS 578T | 5.5 | 4.61 | 4 | 4.78 |
| BT-549 | 5.79 | 5.49 | 5.22 | 5.5 |
| T-47D | 4.87 | 4.42 | 4 | 4.21 |
| MDA-MB-468 | 5.75 | 5.4 | 5.1 | 5.42 |

NUCC-0226695

| Cell Line | NUCC-0226695 all data in units of −log[M] | | | |
|---|---|---|---|---|
| | GI50 | IC50 | LC50 | TGI |
| CCRF-CEM | 4.98 | 4.38 | 4 | 4 |
| HL-60(TB) | 5.65 | 5.41 | 4 | 5.2 |
| K-562 | 5.63 | 5.51 | 4 | 5.15 |
| MOLT-4 | 5.51 | 5.34 | 4 | 5.05 |
| RPMI-8226 | 4.63 | 4.43 | 4 | 4.19 |
| SR | 5.67 | 5.47 | 4 | 5.16 |
| A549/ATCC | 4.76 | 4.53 | 4.13 | 4.45 |
| EKVX | 5.18 | 4.78 | 4.33 | 4.7 |
| HOP-62 | 4.77 | 4.49 | 4.18 | 4.47 |
| HOP-92 | 4.96 | 4.57 | 4.23 | 4.59 |
| NCI-H226 | 4.85 | 4.47 | 4.16 | 4.51 |
| NCI-H23 | 5.58 | 5.31 | 4.51 | 5.08 |
| NCI-H322M | 4.97 | 4.69 | 4.32 | 4.64 |
| NCI-H460 | 5.4 | 5.33 | 4.35 | 4.84 |
| NCI-H522 | 5.74 | 5.46 | 5.06 | 5.4 |
| COLO 205 | 4.82 | 4.57 | 4.15 | 4.49 |
| HCC-2998 | 5.71 | 5.46 | 5.21 | 5.46 |
| HCT-116 | 5.72 | 5.5 | 5.1 | 5.41 |
| HCT-15 | 5.75 | 5.51 | 5.15 | 5.45 |
| HT29 | 5.46 | 5.37 | 4.01 | 4.79 |
| KM12 | 4.79 | 4.55 | 4.22 | 4.51 |
| SW-620 | 5.72 | 5.5 | 5.11 | 5.42 |
| SF-268 | 5.5 | 5.25 | 4.32 | 4.95 |
| SF-295 | 4.94 | 4.7 | 4.28 | 4.61 |
| SF-539 | 4.86 | 4.61 | 4.23 | 4.55 |
| SNB-19 | 4.82 | 4.56 | 4.26 | 4.54 |
| SNB-75 | 4.92 | 4.6 | 4.29 | 4.61 |
| U251 | 5.72 | 5.49 | 5.11 | 5.42 |
| LOX IMVI | 5.79 | 5.55 | 5.26 | 5.52 |

-continued

| | NUCC-0226695 all data in units of −log[M] | | | |
|---|---|---|---|---|
| Cell Line | GI50 | IC50 | LC50 | TGI |
| MALME-3M | 4.9 | 4.59 | 4.3 | 4.6 |
| M14 | 5.53 | 5.36 | 4.34 | 4.97 |
| MDA-MB-435 | 5.31 | 5.12 | 4.35 | 4.75 |
| SK-MEL-2 | 4.8 | 4.5 | 4.21 | 4.51 |
| SK-MEL-28 | 5.68 | 5.44 | 4.78 | 5.31 |
| SK-MEL-5 | 4.96 | 4.74 | 4.32 | 4.64 |
| UACC-257 | 5.51 | 5.19 | 4.37 | 4.92 |
| UACC-62 | 5.5 | 5.25 | 4.44 | 4.89 |
| IGROV1 | 5.73 | 5.49 | 5.17 | 5.45 |
| OVCAR-3 | 5.59 | 5.31 | 4.64 | 5.19 |
| OVCAR-4 | 4.89 | 4.61 | 4.25 | 4.57 |
| OVCAR-5 | 4.75 | 4.49 | 4.11 | 4.43 |
| OVCAR-8 | 5.67 | 5.46 | 4.72 | 5.3 |
| NCI/ADR-RES | 4.99 | 4.74 | 4.16 | 4.58 |
| SK-OV-3 | 4.84 | 4.54 | 4.22 | 4.53 |
| 786-0 | 4.83 | 4.58 | 4.24 | 4.54 |
| A498 | 4.63 | 4 | 4 | 4.13 |
| ACHN | 4.89 | 4.66 | 4.23 | 4.56 |
| CAKI-1 | 4.93 | 4.69 | 4.3 | 4.62 |
| RXF 393 | 5.68 | 5.27 | 4.81 | 5.3 |
| SN12C | 5.71 | 5.48 | 4.79 | 5.3 |
| TK-10 | 4.72 | 4.37 | 4 | 4.29 |
| UO-31 | 5.57 | 5.24 | 4.48 | 4.97 |
| PC-3 | 5.51 | 5.37 | 4.23 | 4.96 |
| DU-145 | 4.9 | 4.66 | 4.28 | 4.59 |
| MCF7 | 5.09 | 4.89 | 4.22 | 4.63 |
| MDA-MB-231/ATCC | 5.79 | 5.53 | 5.23 | 5.51 |
| HS 578T | 5.15 | 4.11 | 4 | 4.38 |
| BT-549 | 4.97 | 4.63 | 4.31 | 4.64 |
| T-47D | 4.86 | 4.36 | 4 | 4.17 |
| MDA-MB-468 | 5.79 | 5.47 | 5.2 | 5.49 |

NUCC-0226698

| | NUCC-0226698 all data in units of −log[M] | | | |
|---|---|---|---|---|
| Cell Line | GI50 | IC50 | LC50 | TGI |
| CCRF-CEM | 5.36 | 5.18 | 4 | 4 |
| HL-60(TB) | 5.68 | 5.44 | 4 | 5.22 |
| K-562 | 5.55 | 5.47 | 4 | 4 |
| MOLT-4 | 5.49 | 5.32 | 4 | 4.77 |
| RPMI-8226 | 4.64 | 4.42 | 4 | 4 |
| SR | 5.56 | 5.41 | 4 | 4.93 |
| A549/ATCC | 4.19 | 4 | 4 | 4 |
| EKVX | 4.85 | 4.51 | 4.04 | 4.44 |
| HOP-62 | 4.33 | 4 | 4 | 4 |
| HOP-92 | 4.64 | 4 | 4 | 4 |
| NCI-H226 | 4.5 | 4 | 4 | 4 |
| NCI-H23 | 5.4 | 5.06 | 4.14 | 4.73 |
| NCI-H322M | 4.85 | 4.49 | 4 | 4.4 |
| NCI-H460 | 4.92 | 4.78 | 4 | 4.44 |
| NCI-H522 | 5.69 | 5.4 | 4 | 5.31 |
| COLO 205 | 4.06 | 4 | 4 | 4 |
| HCC-2998 | 5.54 | 5.28 | 4.46 | 5 |
| HCT-116 | 5.45 | 5.38 | 4 | 4.53 |
| HCT-15 | 5.53 | 5.42 | 4 | 4.83 |
| HT29 | 4.54 | 4.42 | 4 | 4 |
| KM12 | 4.75 | 4.52 | 4.04 | 4.4 |
| SW-620 | 5.26 | 5.15 | 4 | 4.58 |
| SF-268 | 4.97 | 4.68 | 4.1 | 4.54 |
| SF-295 | 4.55 | 4.3 | 4 | 4 |
| SF-539 | 4.76 | 4.49 | 4.02 | 4.39 |
| SNB-19 | 4.68 | 4.4 | 4 | 4.23 |
| SNB-75 | 4.97 | 4.62 | 4.3 | 4.63 |
| U251 | 4.65 | 4.48 | 4 | 4.16 |
| LOX IMVI | 5.78 | 5.54 | 5.23 | 5.51 |
| MALME-3M | 4.8 | 4.44 | 4.11 | 4.46 |
| M14 | 5.39 | 5.16 | 4 | 4.66 |
| MDA-MB-435 | 5.33 | 5.14 | 4.13 | 4.69 |
| SK-MEL-2 | 4.77 | 4.48 | 4.2 | 4.49 |

-continued

| | NUCC-0226698 all data in units of −log[M] | | | |
|---|---|---|---|---|
| Cell Line | GI50 | IC50 | LC50 | TGI |
| SK-MEL-28 | 5.41 | 5.12 | 4.18 | 4.73 |
| SK-MEL-5 | 5.39 | 5.15 | 4.41 | 4.82 |
| UACC-257 | 5.5 | 5.19 | 4.12 | 4.89 |
| UACC-62 | 5.26 | 4.96 | 4.27 | 4.7 |
| IGROV1 | 5.64 | 5.43 | 4.58 | 5.22 |
| OVCAR-3 | 4.83 | 4.54 | 4.14 | 4.48 |
| OVCAR-4 | 4.75 | 4.44 | 4 | 4.35 |
| OVCAR-5 | 4.21 | 4 | 4 | 4 |
| OVCAR-8 | 5.45 | 5.32 | 4 | 4.76 |
| NCI/ADR-RES | 4.85 | 4.56 | 4 | 4.4 |
| SK-OV-3 | 4.35 | 4 | 4 | 4 |
| 786-0 | 4.36 | 4.14 | 4 | 4 |
| A498 | 4 | 4 | 4 | 4 |
| ACHN | 4.65 | 4.47 | 4 | 4 |
| CAKI-1 | 4.63 | 4.37 | 4 | 4 |
| RXF 393 | 4.95 | 4.45 | 4.04 | 4.49 |
| SN12C | 5.19 | 4.93 | 4.16 | 4.63 |
| TK-10 | 4 | 4 | 4 | 4 |
| UO-31 | 5.3 | 4.85 | 4.32 | 4.72 |
| PC-3 | 4.77 | 4.55 | 4 | 4.25 |
| DU-145 | 4.41 | 4.21 | 4 | 4 |
| MCF7 | 4.68 | 4.49 | 4 | 4.17 |
| MDA-MB-231/ATCC | 5.33 | 5 | 4.24 | 4.74 |
| HS 578T | 5.06 | 4 | 4 | 4.3 |
| BT-549 | 4.85 | 4.53 | 4.23 | 4.54 |
| T-47D | 4.52 | 4.1 | 4 | 4 |
| MDA-MB-468 | 5.68 | 5.09 | 4.6 | 5.24 |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

The invention claimed is:

1. A compound, or a pharmaceutically salt thereof, the compound having a formula of

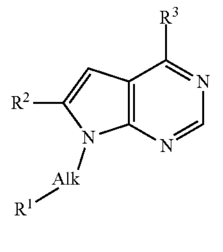

wherein:

Alk is (—$CH_2$—)$_n$, wherein n is 1-6;

$R^1$ is selected from hydrogen, hydroxyl, hydroxyalkyl, amino, alkylamino, dialkylamino, alkoxy, hydroxyalkoxy, or $R^1$ is a 3-, 4-, 5-, or 6-membered ring comprising carbon atoms and optionally comprising one or more heteroatoms selected from N, O, and S, wherein the ring is unsaturated or saturated at one or more positions and the ring optionally is substituted at one or more positions with a substituent selected from oxo, dioxo, alkoxycarbonyl, amidinyl, alkyl, alkoxy, haloalkyl, alkylcarbonyl, aminocarbonyl, halogen, hydroxyl, hydroxyalkyl, and aryl optionally substituted with halo;

$R^2$ is methyl substituted with halo;

$R^3$ is selected from halo, hydrogen, methyl, and hydroxyl; and with the proviso that if $R^2$ is trifluoromethyl, $R^3$ is chloro, and n is 1, then $R^1$ is not piperdine-4-yl or tert-butyl piperidine-1-carboxylate.

2. The compound of claim 1, wherein $R^1$ is selected from pyrrolidine, thiane, azetidine, oxane, piperidine, morpholino, piperazine, pyrazole, phenyl, cyclohexane, and pyridinyl, wherein the pyrrolidine, thiane, azetidine, oxane, piperidine, morpholino, piperazine, pyrazole, phenyl, cyclohexane, or pyridinyl is optionally substituted at one or more positions with a substituent selected from oxo, dioxo, alkoxycarbonyl, amidinyl, alkyl, alkoxy, haloalkyl, alkylcarbonyl, aminocarbonyl, halogen, hydroxyl, hydroxyalkyl, and aryl optionally substituted with halo.

3. The compound of claim 1, wherein $R^2$ is trifluoromethyl.

4. The compound of claim 1, wherein $R^3$ is chloro.

5. The compound of claim 1, wherein n is 1 or 2.

6. The compound of claim 1, wherein $R^2$ is trifluoromethyl, $R^3$ is chloro, and n is 1.

7. The compound of claim 1, wherein $R^2$ is trifluoromethyl, $R^3$ is chloro, and n is 2.

8. The compound of claim 1, wherein if $R^2$ is trifluoromethyl, $R^3$ is chloro, and n is any one of 2-6, then $R^1$ is not an optionally substituted piperidine.

9. The compound of claim 1, wherein if $R^2$ is trifluoromethyl, $R^3$ is chloro, and n is any one of 2-6, then $R^1$ is not piperdine-4-yl.

10. The compound of claim 1, wherein if $R^2$ is trifluoromethyl, $R^3$ is chloro, and n is any one of 2-6, then $R^1$ is not tert-butyl piperidine-1-carboxylate.

11. The compound of claim 1, wherein the compound is selected from

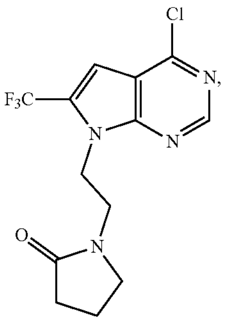

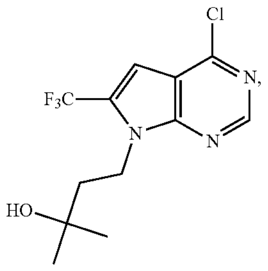

-continued

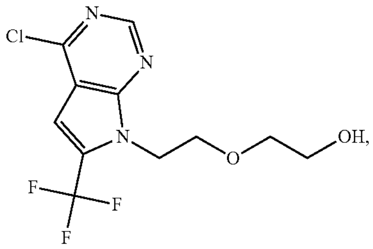

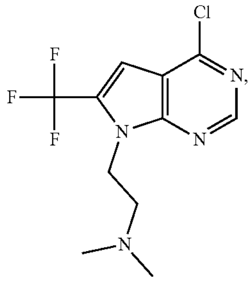

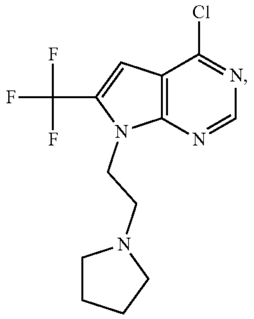

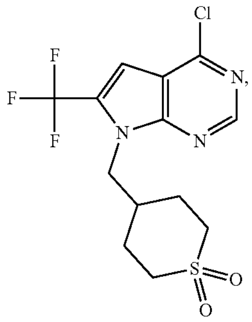

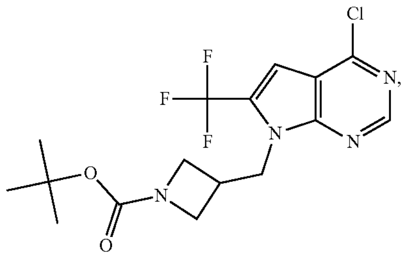

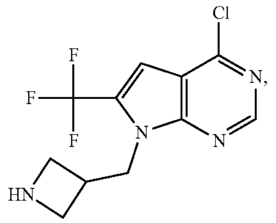

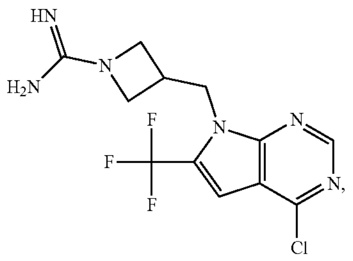

-continued
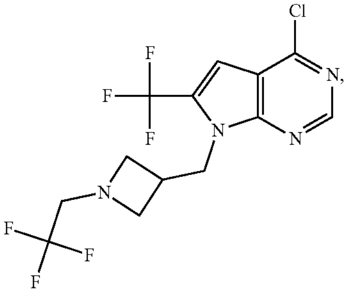
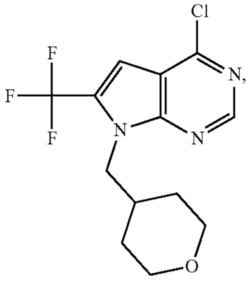
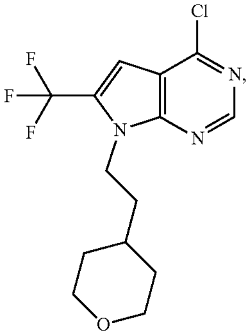
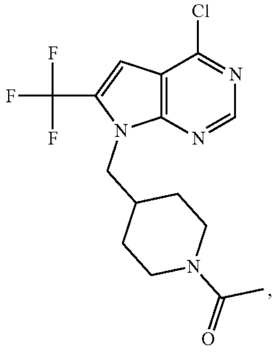
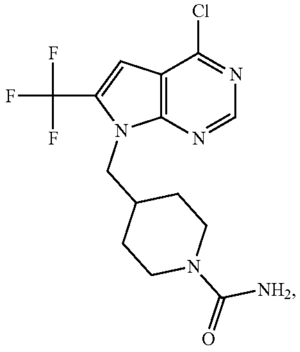
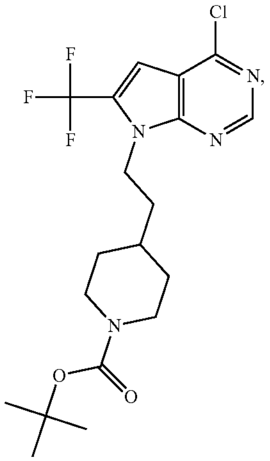
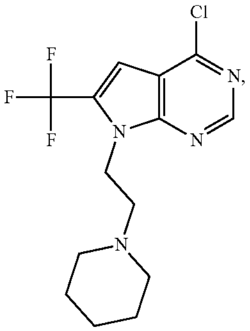
-continued
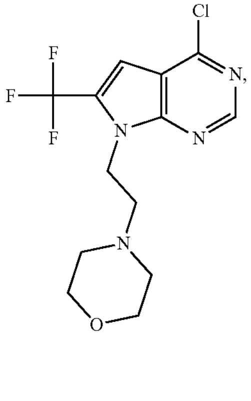
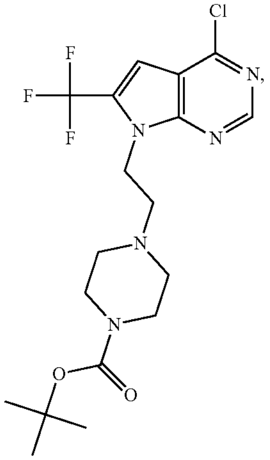
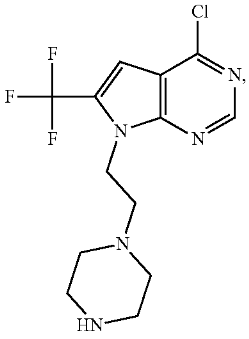
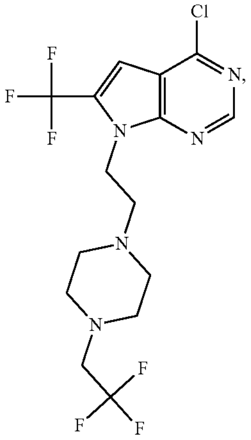
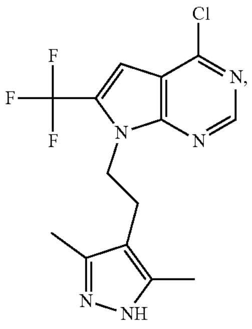
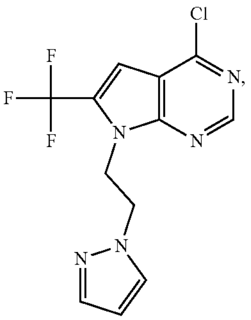
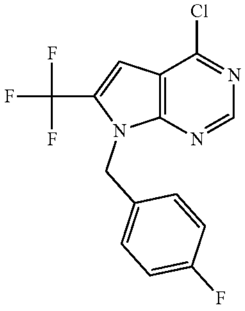
,
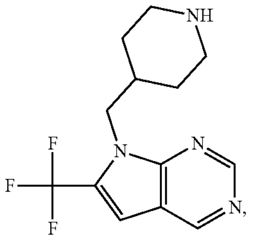

-continued
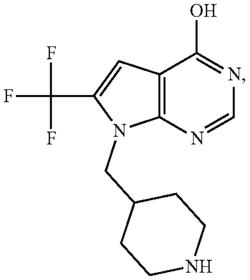
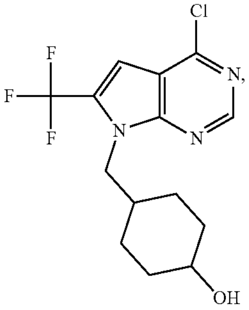
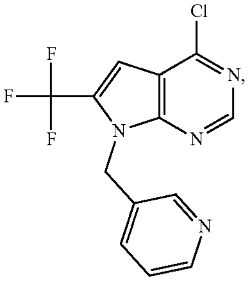
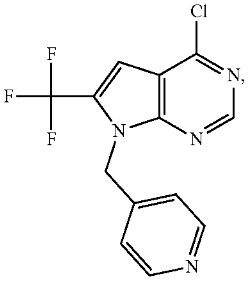
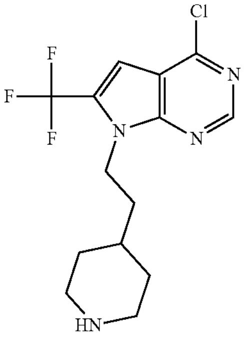
,
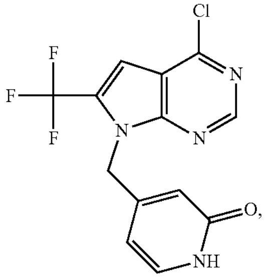
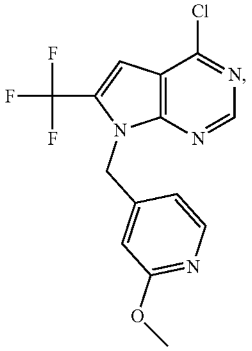
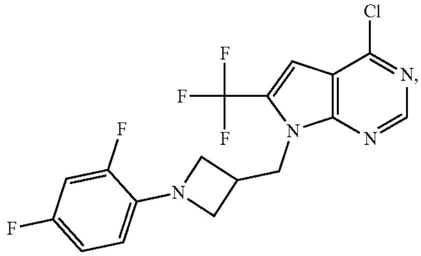
-continued
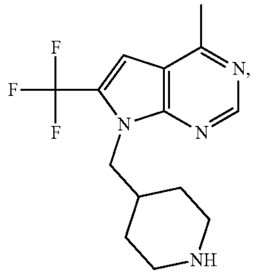
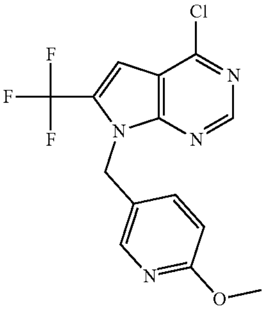
,
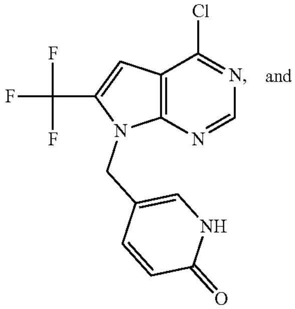
and
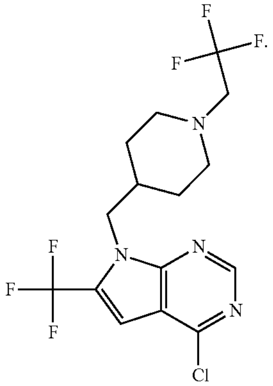
12. The compound of claim 1, wherein the compound is selected from
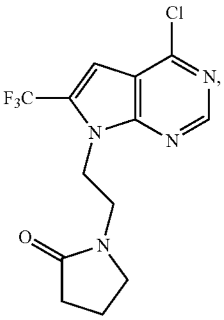
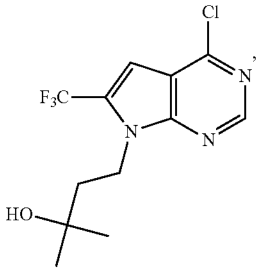
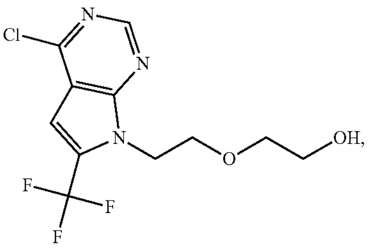

-continued
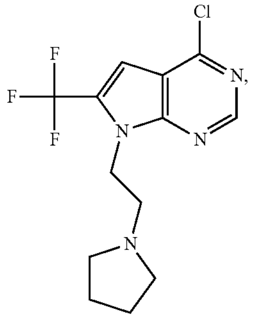
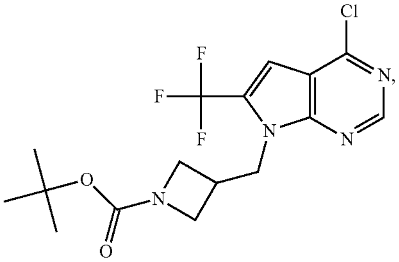
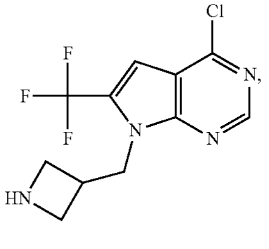
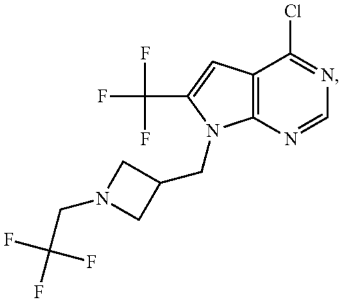
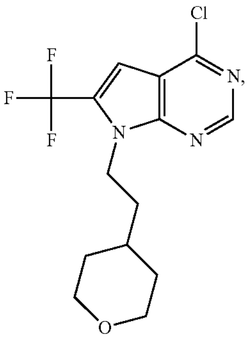
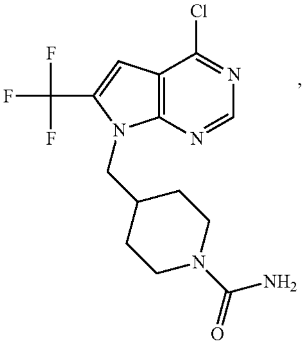
,
-continued
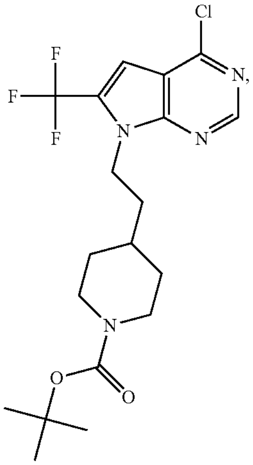
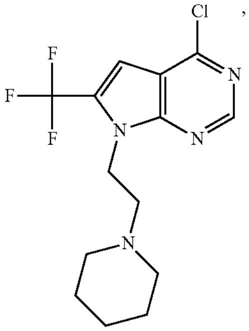
,
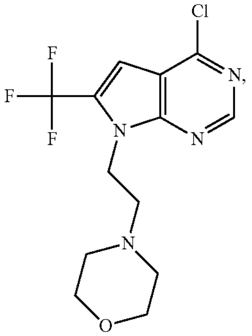
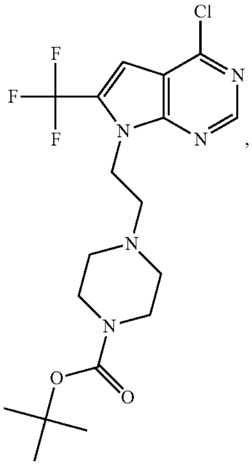
,
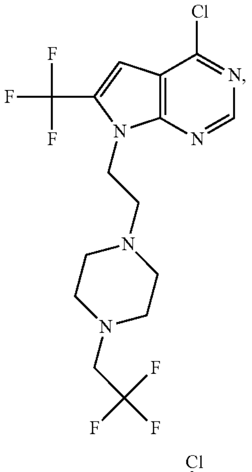
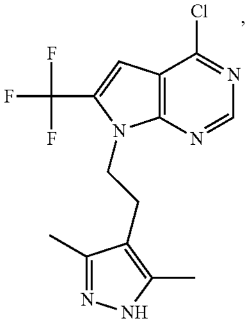
,
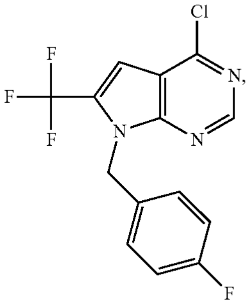
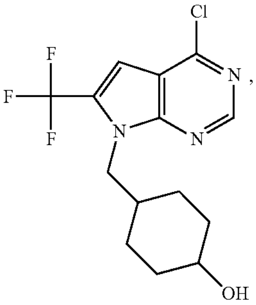

-continued
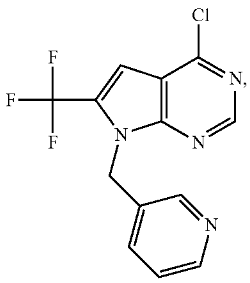
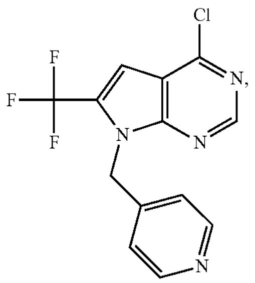
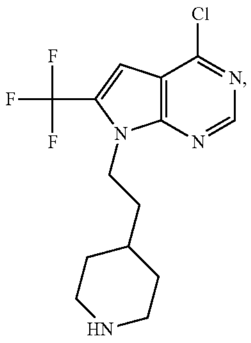
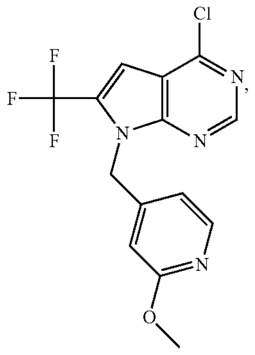
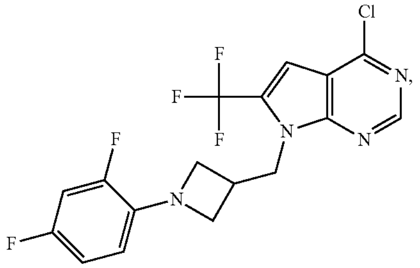
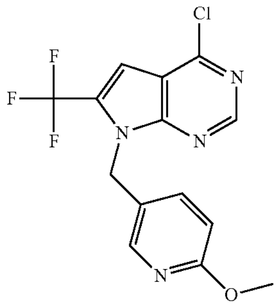
,
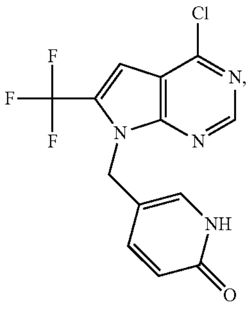
and
-continued
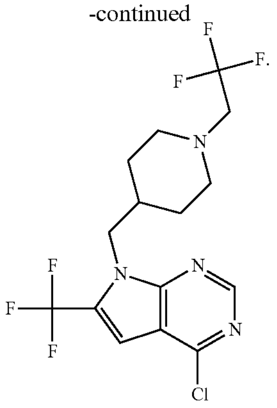
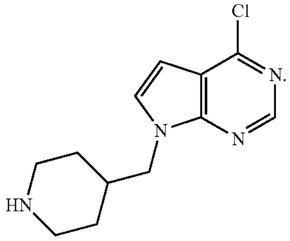 [SMILES: Clc1ncnc2c1ccn2CC1CCNCC1]
13. The compound of claim 1, wherein the compound is selected from
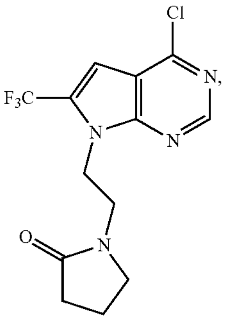
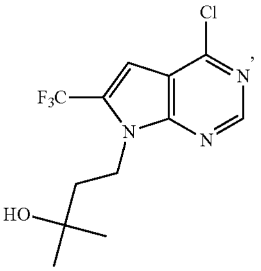
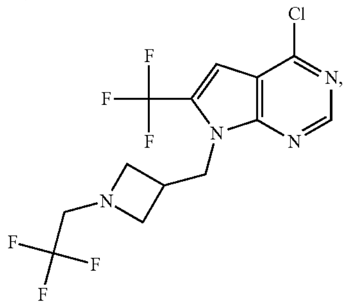
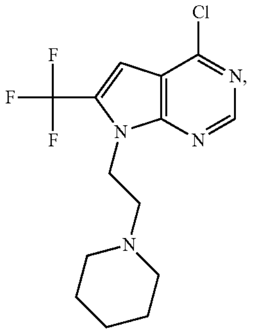
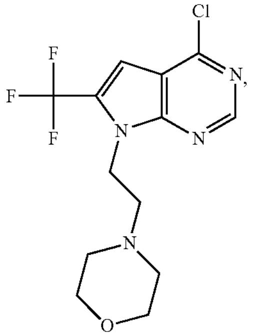

-continued

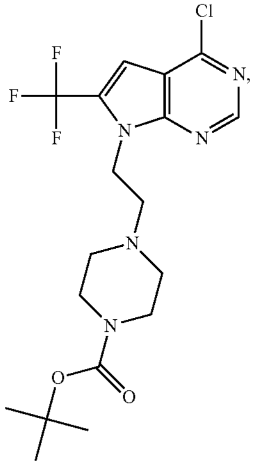

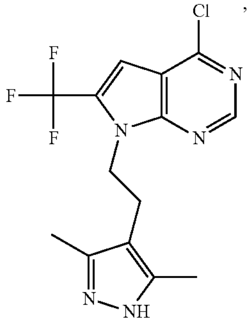

,

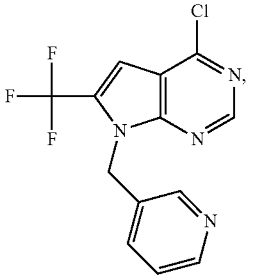

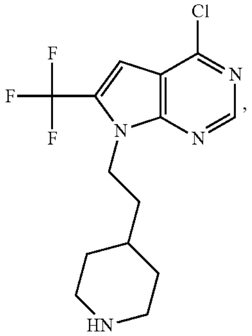

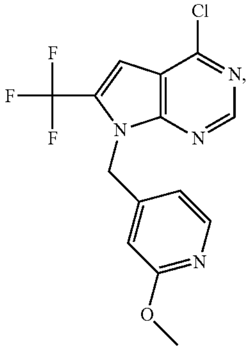

-continued

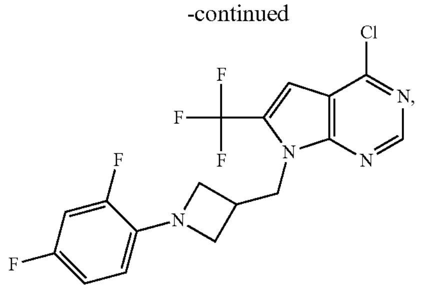

and

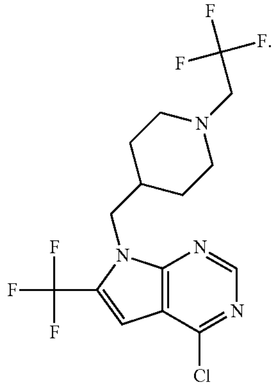

14. A pharmaceutical composition comprising an effective amount of compound according to claim 1 or a pharmaceutically salt thereof, and a suitable pharmaceutical carrier, excipient, or diluent.

15. A method of treating cancer in a subject in need thereof, the method comprising administering the composition of claim 14 to the subject.

16. The method of claim 15, wherein the cancer is a leukemia.

17. The method of claim 15, wherein the cancer is acute myeloid leukemia.

18. A method of inhibiting cell proliferation, the method comprising contacting cells with the compound according to claim 1 or a pharmaceutically salt thereof.

19. The method of claim 18, wherein in the cells are leukemia cells.

20. The method of claim 18, wherein the cells are acute myeloid leukemia cells.

* * * * *